US011535880B2

(12) United States Patent
Minor et al.

(10) Patent No.: US 11,535,880 B2
(45) Date of Patent: Dec. 27, 2022

(54) ARTIFICIAL ORGANELLES FOR ENZYMATIC COFACTOR REDUCTION

(71) Applicant: ENSOVI, INC., Scituate, MA (US)

(72) Inventors: Kyle A. Minor, Sea Bright, NJ (US); Carlo D. Montemagno, Sutton, MA (US); David W. Wendell, Cincinnati, OH (US)

(73) Assignee: ENSOVI, INC., Scituate, MA (US)

( * ) Notice: Subject to any disclaimer, the term of this patent is extended or adjusted under 35 U.S.C. 154(b) by 0 days.

(21) Appl. No.: 17/143,755

(22) Filed: Jan. 7, 2021

(65) Prior Publication Data

US 2021/0214762 A1 Jul. 15, 2021

Related U.S. Application Data

(60) Provisional application No. 62/959,001, filed on Jan. 9, 2020.

(51) Int. Cl.
| | | |
|---|---|---|
| *C07K 14/195* | (2006.01) | |
| *C12P 21/00* | (2006.01) | |
| *C12N 9/02* | (2006.01) | |
| *C07K 14/00* | (2006.01) | |
| *C12N 11/18* | (2006.01) | |
| *C12P 19/36* | (2006.01) | |
| *C07K 14/245* | (2006.01) | |

(52) U.S. Cl.
CPC ............. *C12P 21/00* (2013.01); *C07K 14/00* (2013.01); *C07K 14/195* (2013.01); *C07K 14/245* (2013.01); *C12N 9/0036* (2013.01); *C12N 11/18* (2013.01); *C12P 19/36* (2013.01); *C12Y 106/05003* (2013.01)

(58) Field of Classification Search
CPC ................. C12N 9/0036; C12N 11/18; C12Y 106/05003; C12P 19/36; C07K 14/245
See application file for complete search history.

(56) References Cited

U.S. PATENT DOCUMENTS

2016/0281244 A1 9/2016 Sato et al.
2017/0113193 A1 4/2017 Grzelakowski

FOREIGN PATENT DOCUMENTS

WO 2008152490 A2 12/2008
WO 2011084540 A1 7/2011

OTHER PUBLICATIONS

Masaki Ihara, Yusuke Kawano, Miho Urano, Ayako Okabe, Light Driven CO2 Fixation by Using Cyanobacterial Photosystem I and NADPH-Dependent Formate Dehydrogenase, 2013, PLoS ONE, vol. 8, Issue 8, e71581, pp. 1-8 (Year: 2013).*

(Continued)

*Primary Examiner* — David W Berke-Schlessel
*Assistant Examiner* — Trent R Clarke
(74) *Attorney, Agent, or Firm* — Michael Best & Friedrich LLP

(57) ABSTRACT

Described herein are engineered organelles comprising multi-component proteins from different species incorporated into a membrane structure with interior and exterior aspects. In one embodiment the artificial organelle incorporates one or more protein complexes that absorb optical energy and catalyze electron transfer in biochemical reactions that can be used to reduce $NAD^+$ to NADH or analogues thereof.

26 Claims, 21 Drawing Sheets

Specification includes a Sequence Listing.

(56) References Cited

OTHER PUBLICATIONS

Ferdinand Alte, Anna Stengel, J. Philipp Benz, Eike Petersen, Jürgen Soll, Michael Groll, and Bettina Bölter, Ferredoxin:NADPH oxidoreductase is recruited to thylakoids by binding to a polyproline type II helix in a pH-dependent manner, 2010, PNAS, vol. 107, No. 45, pp. 19260-19265 (Year: 2010).*
Armstrong et al., "Reversibility and efficiency in electrocatalytic energy conversion and lessons from enzymes", Proc. Nat. Acad. Sci. USA, vol. 108, No. 34, 2011, pp. 14049-14054.
Belevich et al., "Activation of respiratory Complex I from *Escherichia coli* studied by fluorescent probes," Heliyon, vol. 3, No. 1, 2017, p28 pages.
Bezborodov et al. "Enzymatic Biocatalysis in Chemical Synthesis of Pharmaceuticals (Review)", Applied Biochemistry and Microbiology, vol. 52, No. 3, 2016 pp. 237-249.
Bridges et al., "Structure of inhibitor-bound mammalian complex I," Nature Comm., vol. 11, No. 5261, 2020, 11 pages.
Casadio, "Measurements of Transmembrane pH Differences of Low Extents in Bacterial Chromatophores—a Study with the Fluorescent-Probe 9-Amino, 6-Chloro, 2-Methoxyacridine," Eur. Biophys. J., vol. 19, No. 4, 1991, pp. 189-201.
D'Alessandro et al., "Quantitative evaluation of the intrinsic uncoupling modulated by ADP and Pi in the reconstituted ATP synthase of *Escherichia coli*," Biochimica Biophysica Acta Bioenerg., vol. 1807, No. 1, 2011, pp. 130-143.
Friedrich et al., "2 Binding-Sites for Naturally-Occurring Inhibitors in Mitochondrial and Bacterial Nadh-Ubiquinone Oxidoreductase (Complex-I)," Biochem Soc. Transact., vol. 22, No. 1, 1994, pp. 226-230.
Guo et al., "Architecture of Human Mitochondrial Respiratory Megacomplex I2III2IV2," Cell, vol. 170, No. 6, 2017, pp. 1247-1257.
Hazard et al., "Improved purification for thermophilic F1F0 ATP synthase using n-dodecyl beta-D-maltoside," Arch, Biochem Biophys., vol. 407, No. 1, 2002, pp. 117-124.
Hua et al., "Self-Directed Reconstitution of Proteorhodopsin with Amphiphilic Block Copolymers Induces the Formation of Hierarchically Ordered Proteopolymer Membrane Arrays", J Am Chem Soc, vol. 133, No. 8, 2011, pp. 2354-2357.
Kampjut et al., "The coupling mechanism of mammalian respiratory complex I," Science, vol. 370, No. 547, 2020, 13 pages.
Liang et al., "The directed cooperative assembly of proteorhodopsin into 2D and 3D polarized arrays", P Natl Acad Sci USA, vol. 104, No. 20, 2007, pp. 8212-8217.
Liang et al., "Inherently tunable electrostatic assembly of membrane proteins," Nano Let. vol. 8, No. 1, 2008, pp. 333-339.
Loll et al., "Towards complete cofactor arrangement in the 3.0 Å resolution structure of photosystem II," Nature, vol. 438, 2005, pp. 1040-1044.
Ohnishi et al., "Possible roles of two quinone molecules in direct and indirect proton pumps of bovine heart NADH-quinone oxidoreductase (complex I)," Biochimica Biophysica Acta Bioenerg., vol. 1797, No. 12, 2010, pp. 1891-1893.
Okuda et al., "Synthesis of Poly(Ethylene Glycol)-Bound NADP by Selective Modification at the 6-Amino Group of NADP", Eur. J. Biochem., vol. 151, 1985 pp. 33-38.
Parey et al., "High-resolution cryo-EM structures of respiratory complex I: Mechanism, assembly, and disease," Science Advances, vol. 5, No. 12, 2009, 10 pages.
Pryde et al. "Superoxide Is Produced by the Reduced Flavin in Mitochondrial Complex I a Single Unified Mechanism that Applies During Both Forward and Reverse Electron Transfer", Journal of Biological Chemistry, vol. 286, 2011, pp. 18056-18065.
Quinto et al., "Recent Trends in Biomimetic NADH Regeneration," Top. Catal., vol. 57, 2014, pp. 321-331.
Rigaud et al., "Reconstitution of membrane proteins into liposomes", Liposomes, Pt B 2003, vol. 372, pp. 65-86.

Sazanov et al., "Structure of the hydrophilic domain of respiratory complex I from Thermus thermophilus," Science, vol. 311, No. 5766, 2006, pp. 1430-1466.
Seigneuret et al., "Analysis of Passive and Light-Driven Ion Movements in Large Bacteriorhodopsin Liposomes Reconstituted by Reverse-Phase Evaporation. 2. Influence of Passive Permeability and Back-Pressure Effects Upon Light-Induced Proton Uptake," Biochemistry, vol. 25, No. 21, 1986, pp. 6723-6730.
Shen et al., "Biomimetic membranes: A review," J. Memb. Sci., vol. 454, pp. 359-381, 2014.
Sheng et al., "Structural insight into light harvesting for photosystem II in green algae," Nature Plants, vol. 5, 2019, pp. 1320-1330.
Steffen et al., "Cation transport by the respiratory NADH: quinone oxidoreductase (complex I): facts and hypotheses", Biochem. Soc. Trans., vol. 41, 2013, pp. 1280-128.
Steuber et al., "Structure of the V. cholerae Na+-pumping NADH:quinone oxidoreductase," Nature vol. 516, 2014, pp. 62-67.
Su et al., "Structure and assembly mechanism of plant C2S2M2-type PSII-LHCII supercomplex," Science, vol. 357, No. 6353, 2017, pp. 815-820.
Umena et al., "Crystal structure of oxygen-evolving photosystem II at a resolution of 1.9 Å," Nature, vol. 473, 2011, pp. 55-60.
Van Bezouwen et al., "Subunit and chlorophyll organization of the plant photosystem II supercomplex," Nature Plants, vol. 3, 2017, 16 pages.
Vavilin, "Methods for the Isolation of Functional Photosystem II Core Particles from the *Cyanobacterium synechocystis* sp. PCC 6803", in Photosynthesis Research Protocols, Second Edition, Ed. by Carpentier, Ed., 2011, vol. 684, pp. 29-40.
Verkhovskaya, "Energy -converting respiratory Complex I: On the way to the molecular mechanism of the proton pump", Int. J. Biochem. & Cell Biol., vol. 45, 2013, pp. 491-511.
Vinogradov et al., "Oxidation of NADH and ROS production by respiratory complex I," Biochimica Biophysica Acta Bioenerg., vol. 1857, No. 7, 2016, pp. 863-887.
Wei et al., "Structure of spinach photosystem II-LHCII supercomplex at 3.2 Å resolution," Nature, vol. 534, 2016, pp. 69-74.
Zhu et al., "Structure of mammalian respiratory complex I," Nature, vol. 536, 2016, pp. 354-358.
Zu et al., "Reversible, Electrochemical Interconversion of NADH and NAD+ by the Catalytic (Iλ) Subcomplex of Mitochondrial NADH:Ubiquinone Oxidoreductase (Complex I)," J. Am. Chem. Soc., vol. 125, No. 20, 2003, pp. 6020-6021.
Baradaran et al., "Crystal structure of the entire respiratory complex I", Nature, vol. 494, 2013, pp. 443-450.
Barber, "Photosystem II: a multisubunit membrane protein that oxidises water", Current Opinion in Structural Biology, vol. 12, 2002, pp. 523-530.
Brandt, "Energy Converting NADH: Quinone Oxidoreductase (Complex I)", Annu. Rev. Biochem, vol. 75, 2006, pp. 69-92.
Bricker et al., "Isolation of a highly active Photosystem II preparation from Synechocystis 6803 using a histidine-tagged mutant of CP 47", Biochimica et Biophysica Acta, vol. 1409, 1998, pp. 50-57.
Brudvig, "Water oxidation chemistry of photosystem II", Phil. Trans. R. Soc. B, vol. 363, 2008, pp. 1211-1219.
Efremov et al., "The architecture of respiratory complex I", Nature, vol. 465, 2010, pp. 441-447.
Friedrich et al., "Assembly of the *Escherichia coli* NADH: ubiquinone oxidoreductase (respiratory complext I)", Biochimica et Biophysica Acta, vol. 1857, 2016, pp. 214-223.
Glockner et al., "Structural Changes of the Oxygen-evolving Complex in Photosystem II during the Catalytic Cycle", The Journal of Biological Chemistry, vol. 288, No. 31, 2013, pp. 22607-22620.
Hsu et al., "The Two Binding Sites for DCMU in Photosystem II", Biochemical and Biophysical Research Communications, vol. 141, No. 2, 1986, pp. 682-688.
Kato et al., "Protein film photoelectrochemistry of the water oxidation enzyme photosystem II", Chem Soc Rev, vol. 43, 2014, pp. 6485-6497.
Kotlyar et al., "NADH oxidation and NAD+ reduction catalysed by tightly coupled inside-out vesicles from Paracoccus denitrificans", Eur. J. Biochem., vol. 269, 2002, pp. 4020-4024.

(56) References Cited

OTHER PUBLICATIONS

Kriegel et al., "Biomimetic Environment to Study *E. coli* Complex I through Surface-Enhanced IR Absorption Spectroscopy", Biochemistry, 2014, 8 pages.
Lee et al., "Coupling Photocatalysis and Redox Biocatalysis Toward Biocatalyzed Artificial Photosynthesis", ChemPubSoc Europe, vol. 19, 2013, pp. 4392-4406.
Liu et al., "Cofactor regeneration for sustainable enzymatic biosynthesis", Biotechnology Advances, vol. 25, 2007, pp. 369-384.
Mavelli et al., "The binding of quinone to the photosynthetic reaction centers: kinetics and thermodynamics of reactions occurring at the Qb-site in zwitterionic and anionic liposomes", Eur Biophys J., vol. 43, 2014, pp. 301-315.
Meyer et al., "The use of enzymes in organic synthesis and the life sciences: perspectives from the Swiss Industrial Biocatalysis Consortium", Catalysis Science and Technology, vol. 3, 2013, pp. 29-40.
Morina et al., "Engineering the Respiratory Complex I to Energy-converting NADPH: Ubiquinone Oxidoreductase", The Journal of Biological Chemistry, 2011, vol. 286, No. 40, pp. 34627-34634.
Muh et al., "Light-induced quinone reduction in photosytem II", Biochimica et Biophysica Acta, vol. 1817, 2012, pp. 44-65.
Nore, "Delta-pH Driven Energy-Linked NAD+ Reduction in Rhodospirillum rubrum Chromatophores", Archives of Biochemistry and Biophysics vol. 274, No. 1, 1989, pp. 285-289.
Ohnishi et al., "A new hypothesis on the simultaneous direct and indirect proton pump mechanisms in NADH-quinone oxidoreductase (complex I)", FEBS Letters, vol. 584, 2010, pp. 4131-4137.
Ohnishi et al., "Functional role of Coenzyme Q in the energy coupling of NADH-CoQ oxidoreductase (Complex I): Stabilization of the semiquinone state with the application of insidepositive membrane potential to proteoliposomes", BioFactors, vol. 32, 2008, pp. 13-22.
Pohl et al., "Lambda Red-Mediated Mutagenesis and Efficient Large Scale Affinity Purification of the *Escherichia coli* NADH: Ubiquinone Oxidoreductase (Complex I)", Biochemistry, vol. 46, 2007, pp. 10694-10702.
Qunito et al., "Recent Trends in Biomimetic NADH Regeneration", Top Catal, vol. 57, 2014, pp. 321-331.
Ramesh et al., "Isolation and characterization of an oxygen evolving photosystem 2 core complex from the thermophilic cyanobacterium Mastigocladus laminosus", Photosynthetic, vol. 40, No. 3, 2002, pp. 355-361.
Saito et al., "Mechanism of proton-coupled quinone reduction in Photosystem II", PNAS, vol. 110, No. 3, 2013, pp. 954-959.
Samec et al., "Theoretical Analysis of Electrochemical Reactions Involving Two Successive One-electron Transfers with Dimerization of Intermediate-Application to NAD+/NADH Redox Couple", J. Electroanal. Chem., vol. 133, 1982, 23 pages.
Selivanov et al., "Reactive Oxygen Species Production by Forward and Reverse Electron Fluxes in the Mitochondrial Respiratory Chain", PLoS Computational Biology, vol. 7, Issue 3, 2011, 17 pages.
Song et al., "Construction of Enzyme-Cofactor/Mediator Conjugates for Enhanced in Vitro Bioelectricty Generation", Bioconjugate Chemistry, 2018, vol. 29, No. 12, pp. 3993-3998.
Steffan et al., "Cation transport by the respiratory NADH: quinone oxidoreductase (complex I): facts and hypotheses", Biochemical Society Transactions, vol. 41, Part 5, 2013, pp. 1280-1287.
Trebst, "Inhibitors in the functional dissection of the photosynthetic edlectron transport system", Photosynth Res., vol. 92, 2007, pp. 217-224.
Uppada et al., "Cofactor Regeneration—an important aspect of biocatalysis", Current Science, vol. 106, No. 7, 2014, pp. 946-957.
Vinogradov, "Catalytic properties of the mitochondrial NADH-ubiquinone oxidoreductase (Complex I) and the pseduo-reversible active/inactive enxyme transition", Biochimica et Biophysica Acta, vol. 1364, 1998, pp. 169-185.
Wang et al., "Fast Isolation of Highly Active Photosystem II Core Complexes from Spinanch", J. of Integrative Plant Biology, vol. 52, No. 9, 2010, pp. 793-800.
Wu et al., "Methods for the regeneration of nicotinamide coenzymes", Green Chemistry Critical Review, vol. 15, 2013, pp. 1773-1789.
International Preliminary Report on Patentability for Application No. PCT/US2021/012475 dated Jul. 12, 2022 (6 pages).
International Search Report and Written Opinion for Application No. PCT/US21/12475 dated Mar. 31, 2021 (14 pages).
Nace, "The Photosynthesis Equation Made Easy", Forbes Science, <https//www.forbes.com/sites/trevornace/2019/08/26/the-photosynthesis-equation-made-easy/?sh=117f2a8b200e>, Aug. 2019, 3 pages.
Ren et al., "Cell-free Artificial Photosynthesis System", Transducers, 2017, pp. 1859-1862.

* cited by examiner

Photosystem II Reaction $$O_2 + 4 H^+_{in} + 2 QH_2 \longleftarrow 2 H_2O + 4 H^+ + 2 Q$$

Complex I Reaction $$NAD^+ + H^+ + 4 H^+_{in} + QH_2 \longleftarrow NADH + 4 H^+_{out} + Q$$

Enlargement of "A" of FIG. 1B

SEQUENCE LISTING

<160> NUMBER OF SEQ ID NOS: 34

<210> SEQ ID NO 1
<211> LENGTH: 507
<212> TYPE: PRT
<213> ORGANISM: Synechocystis PCC6803

<400> SEQUENCE: 1

```
Met Gly Leu Pro Trp Tyr Arg Val His Thr Val Val Leu Asn Asp Pro
1               5                   10                  15

Gly Arg Leu Ile Ser Val His Leu Met His Thr Ala Leu Val Ala Gly
            20                  25                  30

Trp Ala Gly Ser Met Ala Leu Tyr Glu Leu Ala Ile Phe Asp Ser Ser
        35                  40                  45

Asp Ala Val Leu Asn Pro Met Trp Arg Gln Gly Met Phe Val Leu Pro
    50                  55                  60

Phe Met Ala Arg Leu Gly Val Thr Ser Ser Trp Asn Gly Trp Ser Val
65                  70                  75                  80

Thr Gly Glu Thr Gly Leu Asp Pro Gly Phe Trp Ser Phe Glu Gly Val
                85                  90                  95

Ala Ala Ala His Ile Val Leu Ser Gly Leu Leu Phe Leu Ala Ala Val
            100                 105                 110

Trp His Trp Val Phe Trp Asp Leu Glu Leu Phe Val Asp Pro Arg Thr
        115                 120                 125

Gly Glu Ser Ala Leu Asp Leu Pro Lys Met Phe Gly Ile His Leu Phe
    130                 135                 140

Leu Ser Gly Leu Leu Cys Phe Gly Phe Gly Ala Phe His Leu Thr Gly
145                 150                 155                 160

Val Trp Gly Pro Gly Met Trp Val Ser Asp Pro Tyr Gly Leu Thr Gly
                165                 170                 175

His Val Gln Pro Val Ala Pro Glu Trp Gly Pro Ala Gly Phe Asn Pro
            180                 185                 190

Phe Asn Pro Gly Gly Val Val Ala His His Ile Ala Ala Gly Ile Val
        195                 200                 205

Gly Ile Ile Ala Gly Leu Phe His Leu Thr Val Arg Pro Pro Glu Arg
    210                 215                 220

Leu Tyr Lys Ala Leu Arg Met Gly Asn Ile Glu Thr Val Leu Ser Ser
225                 230                 235                 240

Ser Ile Ala Ala Val Phe Phe Ala Ala Phe Val Val Ala Gly Thr Met
                245                 250                 255

Trp Tyr Gly Asn Ala Thr Thr Pro Ile Glu Leu Phe Gly Pro Thr Arg
            260                 265                 270

Tyr Gln Trp Asp Lys Gly Tyr Phe Gln Glu Glu Ile Gln Arg Arg Val
        275                 280                 285

Asp Ser Gln Leu Ala Glu Gly Ala Ser Leu Ser Glu Ala Trp Ser Thr
    290                 295                 300

Ile Pro Glu Lys Leu Ala Phe Tyr Asp Tyr Val Gly Asn Ser Pro Ala
305                 310                 315                 320

Lys Gly Gly Leu Phe Arg Thr Gly Ala Met Asn Ser Gly Asp Gly Ile
```

```
                    325                 330                 335
Ala Gln Glu Trp Ile Gly His Pro Ile Phe Lys Asp Lys Glu Gly Arg
                340                 345                 350
Glu Leu Glu Val Arg Arg Met Pro Asn Phe Phe Glu Thr Phe Pro Val
                355                 360                 365
Ile Met Thr Asp Ala Asp Gly Val Val Arg Ala Asp Ile Pro Phe Arg
                370                 375                 380
Arg Ser Glu Ser Lys Phe Ser Val Glu Gln Thr Gly Val Thr Val Ser
385                 390                 395                 400
Phe Tyr Gly Gly Ala Leu Asp Gly Gln Thr Phe Ser Asn Pro Ser Asp
                405                 410                 415
Val Lys Lys Phe Ala Arg Lys Ala Gln Leu Gly Glu Gly Phe Asp Phe
                420                 425                 430
Asp Thr Glu Thr Phe Asn Ser Asp Gly Val Phe Arg Thr Ser Pro Arg
                435                 440                 445
Gly Trp Phe Thr Phe Gly His Ala Val Phe Ala Leu Leu Phe Phe Phe
                450                 455                 460
Gly His Ile Trp His Gly Ser Arg Thr Leu Phe Arg Asp Val Phe Ala
465                 470                 475                 480
Gly Val Asp Pro Gly Leu Glu Glu Gln Val Glu Phe Gly Val Phe Ala
                485                 490                 495
Lys Val Gly Asp Leu Ser Thr Arg Lys Glu Ala
                500                 505

<210> SEQ ID NO 2
<211> LENGTH: 460
<212> TYPE: PRT
<213> ORGANISM: Synechocystis PCC6803

<400> SEQUENCE: 2

Met Val Thr Leu Ser Asn Thr Ser Met Val Gly Gly Arg Asp Leu Pro
1               5                   10                  15
Ser Thr Gly Phe Ala Trp Trp Ser Gly Asn Ala Arg Leu Ile Asn Leu
                20                  25                  30
Ser Gly Lys Leu Leu Gly Ala His Val Ala His Ala Gly Leu Ile Val
            35                  40                  45
Phe Trp Ala Gly Ala Met Thr Leu Phe Glu Val Ala His Phe Ile Pro
    50                  55                  60
Glu Lys Pro Met Tyr Glu Gln Gly Leu Ile Leu Leu Pro His Ile Ala
65                  70                  75                  80
Thr Leu Gly Trp Gly Val Gly Pro Ala Gly Glu Val Thr Asp Ile Phe
                85                  90                  95
Pro Phe Phe Val Val Gly Val Leu His Leu Ile Ser Ser Ala Val Leu
                100                 105                 110
Gly Leu Gly Gly Ile Tyr His Ala Leu Arg Gly Pro Glu Val Leu Glu
            115                 120                 125
Glu Tyr Ser Ser Phe Phe Gly Tyr Asp Trp Lys Asp Lys Asn Gln Met
    130                 135                 140
Thr Asn Ile Ile Gly Tyr His Leu Ile Leu Leu Gly Cys Gly Ala Leu
145                 150                 155                 160
Leu Leu Val Phe Lys Ala Met Phe Phe Gly Gly Val Tyr Asp Thr Trp
                165                 170                 175
Ala Pro Gly Gly Gly Asp Val Arg Val Ile Thr Asn Pro Thr Leu Asn
                180                 185                 190
```

Pro Ala Ile Ile Phe Gly Tyr Leu Leu Lys Ala Pro Phe Gly Gly Glu
            195                 200                 205

Gly Trp Ile Ile Ser Val Asn Asn Met Glu Asp Ile Ile Gly Gly His
        210                 215                 220

Ile Trp Ile Gly Leu Ile Cys Ile Ser Gly Ile Trp His Ile Leu
225                 230                 235                 240

Thr Lys Pro Phe Gly Trp Ala Arg Arg Ala Leu Ile Trp Ser Gly Glu
                245                 250                 255

Ala Tyr Leu Ser Tyr Ser Leu Gly Ala Leu Ser Leu Met Gly Phe Ile
            260                 265                 270

Ala Ser Val Phe Val Trp Phe Asn Asn Thr Ala Tyr Pro Ser Glu Phe
        275                 280                 285

Tyr Gly Pro Thr Gly Met Glu Ala Ser Gln Ser Gln Ala Phe Thr Phe
    290                 295                 300

Leu Val Arg Asp Gln Arg Leu Gly Ala Asn Ile Ala Ser Ala Gln Gly
305                 310                 315                 320

Pro Thr Gly Leu Gly Lys Tyr Leu Met Arg Ser Pro Ser Gly Glu Ile
                325                 330                 335

Ile Phe Gly Gly Glu Thr Met Arg Phe Trp Asp Phe Arg Gly Pro Trp
            340                 345                 350

Leu Glu Pro Leu Arg Gly Pro Asn Gly Leu Asp Leu Asp Lys Leu Arg
        355                 360                 365

Asn Asp Ile Gln Pro Trp Gln Val Arg Arg Ala Ala Glu Tyr Met Thr
    370                 375                 380

His Ala Pro Leu Gly Ser Leu Asn Ser Val Gly Gly Val Ile Thr Asp
385                 390                 395                 400

Val Asn Ser Phe Asn Tyr Val Ser Pro Arg Ala Trp Leu Ala Thr Ser
                405                 410                 415

His Phe Val Leu Gly Phe Phe Phe Leu Val Gly His Leu Trp His Ala
            420                 425                 430

Gly Arg Ala Arg Ala Ala Ala Gly Phe Glu Lys Gly Ile Asp Arg
        435                 440                 445

Glu Thr Glu Pro Thr Leu Phe Met Pro Asp Leu Asp
    450                 455                 460

<210> SEQ ID NO 3
<211> LENGTH: 64
<212> TYPE: PRT
<213> ORGANISM: Synechocystis PCC6803

<400> SEQUENCE: 3

Met Ala Gln Arg Thr Arg Leu Gly Asp Ile Leu Arg Pro Leu Asn Ser
1               5                   10                  15

Glu Tyr Gly Lys Val Val Pro Gly Trp Gly Thr Thr Pro Val Met Gly
            20                  25                  30

Val Phe Met Ala Leu Phe Leu Val Phe Leu Leu Ile Ile Leu Gln Ile
        35                  40                  45

Tyr Asn Ser Ser Leu Ile Leu Glu Gly Phe Ser Val Asp Trp Ala Gly
    50                  55                  60

<210> SEQ ID NO 4
<211> LENGTH: 38
<212> TYPE: PRT
<213> ORGANISM: Synechocystis PCC6803

<400> SEQUENCE: 4

```
Met Leu Thr Leu Lys Ile Ala Val Tyr Ile Val Gly Leu Phe Ile
1               5                  10                  15

Ser Leu Phe Ile Phe Gly Phe Leu Ser Ser Asp Pro Thr Arg Asn Pro
                20                  25                  30

Gly Arg Lys Asp Phe Glu
            35

<210> SEQ ID NO 5
<211> LENGTH: 39
<212> TYPE: PRT
<213> ORGANISM: Synechocystis PCC6803

<400> SEQUENCE: 5

Met Phe Ala Glu Gly Arg Ile Pro Leu Trp Val Val Gly Val Val Ala
1               5                  10                  15

Gly Ile Gly Ala Ile Gly Val Leu Gly Leu Phe Phe Tyr Gly Ala Tyr
                20                  25                  30

Ala Gly Leu Gly Ser Ser Met
            35

<210> SEQ ID NO 6
<211> LENGTH: 45
<212> TYPE: PRT
<213> ORGANISM: Synechocystis PCC6803

<400> SEQUENCE: 6

Met Glu Thr Ile Tyr Leu Leu Ala Lys Leu Pro Glu Ala Tyr Gln Ile
1               5                  10                  15

Phe Asp Pro Leu Val Asp Val Leu Pro Val Ile Pro Leu Phe Phe Leu
                20                  25                  30

Ala Leu Ala Phe Val Trp Gln Ala Ala Val Gly Phe Lys
            35                  40                  45

<210> SEQ ID NO 7
<211> LENGTH: 39
<212> TYPE: PRT
<213> ORGANISM: Synechocystis PCC6803

<400> SEQUENCE: 7

Met Asp Arg Asn Ser Asn Pro Asn Arg Gln Pro Val Glu Leu Asn Arg
1               5                  10                  15

Thr Ser Leu Tyr Leu Gly Leu Leu Leu Val Ala Val Leu Gly Ile Leu
                20                  25                  30

Phe Ser Ser Tyr Phe Phe Asn
            35

<210> SEQ ID NO 8
<211> LENGTH: 35
<212> TYPE: PRT
<213> ORGANISM: Synechocystis PCC6803

<400> SEQUENCE: 8

Met Gln Val Asn Asn Leu Gly Phe Ile Ala Ser Ile Leu Phe Val Leu
1               5                  10                  15

Val Pro Thr Val Phe Leu Leu Ile Leu Phe Ile Gln Thr Gly Lys Gln
                20                  25                  30

Ser Glu Ser
        35

<210> SEQ ID NO 9
```

```
<211> LENGTH: 31
<212> TYPE: PRT
<213> ORGANISM: Synechocystis PCC6803

<400> SEQUENCE: 9

Met Glu Ser Val Ala Tyr Ile Leu Val Leu Thr Met Ala Leu Ala Val
1               5                   10                  15

Leu Phe Phe Ala Ile Ala Phe Arg Glu Pro Pro Arg Ile Glu Lys
            20                  25                  30

<210> SEQ ID NO 10
<211> LENGTH: 39
<212> TYPE: PRT
<213> ORGANISM: Synechocystis PCC6803

<400> SEQUENCE: 10

Met Thr Pro Ser Leu Ala Asn Phe Leu Trp Ser Leu Val Leu Gly Ala
1               5                   10                  15

Ala Ile Val Leu Ile Pro Ala Thr Val Gly Leu Ile Phe Ile Ser Gln
            20                  25                  30

Lys Asp Lys Ile Thr Arg Ser
        35

<210> SEQ ID NO 11
<211> LENGTH: 39
<212> TYPE: PRT
<213> ORGANISM: Synechocystis PCC6803

<400> SEQUENCE: 11

Met Asp Trp Arg Val Ile Val Val Val Ser Pro Leu Leu Ile Ala Ala
1               5                   10                  15

Thr Trp Ala Ala Ile Asn Ile Gly Ala Ala Ile Arg Gln Leu Gln
            20                  25                  30

Asp Val Leu Gly Arg Glu Ala
        35

<210> SEQ ID NO 12
<211> LENGTH: 39
<212> TYPE: PRT
<213> ORGANISM: Synechocystis PCC6803

<400> SEQUENCE: 12

Met Glu Leu Leu Ala Ala Leu Asn Leu Glu Pro Ile Phe Gln Leu Thr
1               5                   10                  15

Phe Leu Gly Leu Ile Val Leu Ala Gly Pro Ala Val Val Phe Val Leu
            20                  25                  30

Ala Phe Arg Gly Gly Asp Leu
        35

<210> SEQ ID NO 13
<211> LENGTH: 62
<212> TYPE: PRT
<213> ORGANISM: Synechocystis PCC6803

<400> SEQUENCE: 13

Met Ser Ile Val Phe Gln Ile Ala Leu Ala Ala Leu Val Leu Phe Ser
1               5                   10                  15

Phe Val Met Val Val Gly Val Pro Val Ala Tyr Ala Ser Pro Gln Asn
            20                  25                  30

Trp Asp Arg Ser Lys Pro Leu Leu Tyr Leu Gly Ser Gly Ile Trp Ala
        35                  40                  45
```

```
Ile Leu Val Ile Val Val Ala Leu Leu Asn Phe Leu Val Val
        50                  55                  60

<210> SEQ ID NO 14
<211> LENGTH: 112
<212> TYPE: PRT
<213> ORGANISM: Synechocystis PCC6803

<400> SEQUENCE: 14

Met Ala Glu Ile Gln Phe Ser Lys Gly Val Ala Glu Thr Val Val Pro
 1               5                  10                  15

Glu Val Arg Leu Ser Lys Ser Lys Asn Gly Gln Ser Gly Met Ala Lys
            20                  25                  30

Phe Tyr Phe Leu Glu Pro Thr Ile Leu Ala Lys Glu Ser Thr Asp Asp
        35                  40                  45

Ile Thr Gly Met Tyr Leu Ile Asp Asp Glu Gly Glu Ile Ile Thr Arg
    50                  55                  60

Glu Val Lys Gly Lys Phe Ile Asn Gly Arg Pro Thr Ala Ile Glu Ala
65                  70                  75                  80

Thr Val Ile Leu Asn Ser Gln Pro Glu Trp Asp Arg Phe Met Arg Phe
                85                  90                  95

Met Glu Arg Tyr Gly Ala Glu Asn Gly Leu Gly Phe Ser Lys Ser Glu
            100                 105                 110

<210> SEQ ID NO 15
<211> LENGTH: 360
<212> TYPE: PRT
<213> ORGANISM: Synechocystis PCC6803

<400> SEQUENCE: 15

Met Thr Thr Thr Gln Leu Gly Leu Gln Glu Gln Ser Leu Trp Ser Arg
 1               5                  10                  15

Phe Cys Cys Trp Ile Thr Ser Thr Ser Asn Arg Leu Tyr Ile Gly Trp
            20                  25                  30

Phe Gly Val Leu Met Ile Pro Thr Leu Leu Thr Ala Thr Thr Cys Phe
        35                  40                  45

Ile Ile Ala Phe Ile Ala Ala Pro Val Asp Ile Asp Gly Ile Arg
    50                  55                  60

Glu Pro Ile Ala Gly Ser Leu Leu Tyr Gly Asn Asn Ile Ile Thr Ala
65                  70                  75                  80

Ala Val Val Pro Ser Ser Asn Ala Ile Gly Leu His Phe Tyr Pro Ile
                85                  90                  95

Trp Glu Ala His Ser Leu Asp Glu Trp Leu Tyr Asn Gly Gly Pro Tyr
            100                 105                 110

Gln Leu Ile Val Phe His Phe Leu Ile Gly Ile Phe Cys Tyr Leu Gly
        115                 120                 125

Arg Gln Trp Glu Leu Ser Tyr Arg Leu Gly Met Arg Pro Trp Ile Cys
    130                 135                 140

Val Ala Tyr Ser Ala Pro Val Ala Ala Thr Ala Thr Leu Leu Ile
145                 150                 155                 160

Tyr Ser Ile Gly Gln Gly Ser Phe Ser Asp Gly Leu Pro Leu Gly Ile
                165                 170                 175

Ser Gly Thr Phe Asn Phe Met Leu Val Leu Gln Ala Glu His Asn Val
            180                 185                 190

Leu Met His Pro Phe His Met Leu Gly Val Ala Gly Val Phe Gly Gly
        195                 200                 205
```

```
Ala Leu Phe Ala Ala Met His Gly Ser Leu Val Thr Ser Ser Leu Ile
    210                 215                 220

Arg Glu Thr Thr Glu Val Glu Ser Gln Asn Gln Gly Tyr Lys Phe Gly
225                 230                 235                 240

Gln Glu Glu Glu Thr Tyr Asn Ile Val Ala Ala His Gly Tyr Phe Gly
                245                 250                 255

Arg Leu Ile Phe Gln Tyr Ala Ser Phe Asn Asn Ser Arg Ala Leu His
            260                 265                 270

Phe Phe Leu Gly Ala Trp Pro Val Gly Ile Trp Phe Ala Ala Leu
        275                 280                 285

Ala Val Cys Cys Phe Ala Phe Asn Leu Asn Gly Phe Asn Phe Asn Gln
    290                 295                 300

Ser Ile Leu Asp Ala Gln Gly Arg Pro Val Ser Thr Trp Ala Asp Val
305                 310                 315                 320

Ile Asn Arg Ala Asn Ile Gly Phe Glu Val Met His Glu Arg Asn Val
                325                 330                 335

His Asn Phe Pro Leu Asp Leu Ala Ser Gly Asp Ala Gln Met Val Ala
            340                 345                 350

Leu Asn Ala Pro Ala Ile Glu Gly
        355                 360

<210> SEQ ID NO 16
<211> LENGTH: 360
<212> TYPE: PRT
<213> ORGANISM: Synechocystis PCC6803

<400> SEQUENCE: 16

Met Thr Thr Thr Leu Gln Gln Arg Glu Ser Ala Ser Leu Trp Glu Gln
1               5                   10                  15

Phe Cys Gln Trp Val Thr Ser Thr Asn Asn Arg Ile Tyr Val Gly Trp
            20                  25                  30

Phe Gly Thr Leu Met Ile Pro Thr Leu Leu Thr Ala Thr Thr Cys Phe
        35                  40                  45

Ile Ile Ala Phe Ile Ala Ala Pro Val Asp Ile Asp Gly Ile Arg
50                  55                  60

Glu Pro Val Ala Gly Ser Leu Leu Tyr Gly Asn Asn Ile Ile Ser Gly
65                  70                  75                  80

Ala Val Val Pro Ser Ser Asn Ala Ile Gly Leu His Phe Tyr Pro Ile
                85                  90                  95

Trp Glu Ala Ala Ser Leu Asp Glu Trp Leu Tyr Asn Gly Gly Pro Tyr
            100                 105                 110

Gln Leu Val Val Phe His Phe Leu Ile Gly Ile Phe Cys Tyr Met Gly
        115                 120                 125

Arg Gln Trp Glu Leu Ser Tyr Arg Leu Gly Met Arg Pro Trp Ile Cys
130                 135                 140

Val Ala Tyr Ser Ala Pro Val Ser Ala Ala Thr Ala Val Phe Leu Ile
145                 150                 155                 160

Tyr Pro Ile Gly Gln Gly Ser Phe Ser Asp Gly Met Pro Leu Gly Ile
                165                 170                 175

Ser Gly Thr Phe Asn Phe Met Ile Val Phe Gln Ala Glu His Asn Ile
            180                 185                 190

Leu Met His Pro Phe His Met Leu Gly Val Ala Gly Val Phe Gly Gly
        195                 200                 205

Ser Leu Phe Ser Ala Met His Gly Ser Leu Val Thr Ser Ser Leu Val
```

```
              210                 215                 220
Arg Glu Thr Thr Glu Val Glu Ser Gln Asn Tyr Gly Tyr Lys Phe Gly
225                 230                 235                 240

Gln Glu Glu Glu Thr Tyr Asn Ile Val Ala Ala His Gly Tyr Phe Gly
                245                 250                 255

Arg Leu Ile Phe Gln Tyr Ala Ser Phe Asn Asn Ser Arg Ser Leu His
                260                 265                 270

Phe Phe Leu Gly Ala Trp Pro Val Ile Gly Ile Trp Phe Thr Ala Met
            275                 280                 285

Gly Val Ser Thr Met Ala Phe Asn Leu Asn Gly Phe Asn Phe Asn Gln
            290                 295                 300

Ser Ile Leu Asp Ser Gln Gly Arg Val Ile Gly Thr Trp Ala Asp Val
305                 310                 315                 320

Leu Asn Arg Ala Asn Ile Gly Phe Glu Val Met His Glu Arg Asn Ala
                325                 330                 335

His Asn Phe Pro Leu Asp Leu Ala Ser Gly Glu Gln Ala Pro Val Ala
                340                 345                 350

Leu Thr Ala Pro Ala Val Asn Gly
            355                 360

<210> SEQ ID NO 17
<211> LENGTH: 352
<212> TYPE: PRT
<213> ORGANISM: Synechocystis PCC6803

<400> SEQUENCE: 17

Met Thr Ile Ala Val Gly Arg Ala Pro Val Glu Arg Gly Trp Phe Asp
1               5                   10                  15

Val Leu Asp Asp Trp Leu Lys Arg Asp Arg Phe Val Phe Ile Gly Trp
                20                  25                  30

Ser Gly Leu Leu Leu Phe Pro Cys Ala Phe Met Ala Leu Gly Gly Trp
                35                  40                  45

Leu Thr Gly Thr Thr Phe Val Thr Ser Trp Tyr Thr His Gly Leu Ala
        50                  55                  60

Ser Ser Tyr Leu Glu Gly Ala Asn Phe Leu Thr Val Ala Val Ser Ser
65                  70                  75                  80

Pro Ala Asp Ala Phe Gly His Ser Leu Leu Phe Leu Trp Gly Pro Glu
                85                  90                  95

Ala Gln Gly Asn Leu Thr Arg Trp Phe Gln Ile Gly Gly Leu Trp Pro
                100                 105                 110

Phe Val Ala Leu His Gly Ala Phe Gly Leu Ile Gly Phe Met Leu Arg
            115                 120                 125

Gln Phe Glu Ile Ser Arg Leu Val Gly Ile Arg Pro Tyr Asn Ala Ile
    130                 135                 140

Ala Phe Ser Gly Pro Ile Ala Val Phe Ser Val Phe Leu Met Tyr
145                 150                 155                 160

Pro Leu Gly Gln Ser Ser Trp Phe Phe Ala Pro Ser Phe Gly Val Ala
                165                 170                 175

Gly Ile Phe Arg Phe Ile Leu Phe Leu Gln Gly Phe His Asn Trp Thr
                180                 185                 190

Leu Asn Pro Phe His Met Met Gly Val Ala Gly Ile Leu Gly Gly Ala
            195                 200                 205

Leu Leu Cys Ala Ile His Gly Ala Thr Val Glu Asn Thr Leu Phe Glu
        210                 215                 220
```

Asp Gly Glu Asp Ser Asn Thr Phe Arg Ala Phe Glu Pro Thr Gln Ala
225                 230                 235                 240

Glu Glu Thr Tyr Ser Met Val Thr Ala Asn Arg Phe Trp Ser Gln Ile
                245                 250                 255

Phe Gly Ile Ala Phe Ser Asn Lys Arg Trp Leu His Phe Phe Met Leu
            260                 265                 270

Phe Val Pro Val Thr Gly Leu Trp Met Ser Ser Val Gly Ile Val Gly
        275                 280                 285

Leu Ala Leu Asn Leu Arg Ala Tyr Asp Phe Val Ser Gln Glu Leu Arg
    290                 295                 300

Ala Ala Glu Asp Pro Glu Phe Glu Thr Phe Tyr Thr Lys Asn Ile Leu
305                 310                 315                 320

Leu Asn Glu Gly Met Arg Ala Trp Met Ala Pro Gln Asp Gln Pro His
                325                 330                 335

Glu Asn Phe Ile Phe Pro Glu Val Leu Pro Arg Gly Asn Ala Leu
            340                 345                 350

<210> SEQ ID NO 18
<211> LENGTH: 274
<212> TYPE: PRT
<213> ORGANISM: Synechocystis PCC6803

<400> SEQUENCE: 18

Met Arg Phe Arg Pro Ser Ile Val Ala Leu Leu Ser Val Cys Phe Gly
1               5                   10                  15

Leu Leu Thr Phe Leu Tyr Ser Gly Ser Ala Phe Ala Val Asp Lys Ser
            20                  25                  30

Gln Leu Thr Tyr Asp Asp Ile Val Asn Thr Gly Leu Ala Asn Val Cys
        35                  40                  45

Pro Glu Ile Ser Ser Phe Thr Arg Gly Thr Ile Glu Val Glu Pro Asn
    50                  55                  60

Thr Lys Tyr Phe Val Ser Asp Phe Cys Met Glu Pro Gln Glu Tyr Phe
65                  70                  75                  80

Val Lys Glu Glu Pro Val Asn Lys Arg Gln Lys Ala Glu Tyr Val Lys
                85                  90                  95

Gly Lys Val Leu Thr Arg Gln Thr Thr Ser Leu Glu Gln Ile Arg Gly
            100                 105                 110

Ser Ile Ala Val Gly Ala Asp Gly Thr Leu Thr Phe Lys Glu Lys Asp
        115                 120                 125

Gly Ile Asp Phe Gln Pro Ile Thr Val Leu Leu Pro Gly Gly Glu Glu
    130                 135                 140

Val Pro Phe Phe Phe Thr Val Lys Asn Phe Thr Gly Thr Thr Glu Pro
145                 150                 155                 160

Gly Phe Thr Ser Ile Asn Ser Ser Thr Asp Phe Val Gly Asp Phe Asn
                165                 170                 175

Val Pro Ser Tyr Arg Gly Ala Gly Phe Leu Asp Pro Lys Ala Arg Gly
            180                 185                 190

Leu Tyr Thr Gly Tyr Asp Asn Ala Val Ala Leu Pro Ser Ala Ala Asp
        195                 200                 205

Lys Phe Arg Thr Asn Lys Lys Glu Thr Pro Leu Gly Lys Gly Thr Leu
    210                 215                 220

Ser Leu Gln Val Thr Gln Val Asp Gly Ser Thr Gly Glu Ile Ala Gly
225                 230                 235                 240

Ile Phe Glu Ser Glu Gln Pro Ser Asp Thr Asp Leu Gly Ala Lys Glu
                245                 250                 255

```
Pro Leu Asp Val Lys Val Arg Gly Ile Phe Tyr Gly Arg Val Asp Thr
            260                 265                 270

Asp Val

<210> SEQ ID NO 19
<211> LENGTH: 134
<212> TYPE: PRT
<213> ORGANISM: Synechocystis PCC6803

<400> SEQUENCE: 19

Met Ser Phe Leu Lys Asn Gln Leu Ser Arg Leu Leu Ala Leu Ile Leu
1               5                   10                  15

Val Val Ala Ile Gly Leu Thr Ala Cys Asp Ser Gly Thr Gly Leu Thr
            20                  25                  30

Gly Asn Tyr Ser Gln Asp Thr Leu Thr Val Ile Ala Thr Leu Arg Glu
        35                  40                  45

Ala Ile Asp Leu Pro Gln Asp Ala Pro Asn Arg Gln Glu Val Gln Asp
    50                  55                  60

Thr Ala Arg Gly Gln Ile Asn Asp Tyr Ile Ser Arg Tyr Arg Arg Lys
65                  70                  75                  80

Gly Asp Ala Gly Gly Leu Lys Ser Phe Thr Thr Met Gln Thr Ala Leu
                85                  90                  95

Asn Ser Leu Ala Gly Tyr Tyr Thr Ser Tyr Gly Ala Arg Pro Ile Pro
            100                 105                 110

Glu Lys Leu Lys Lys Arg Leu Gln Leu Glu Phe Thr Gln Ala Glu Arg
        115                 120                 125

Ser Ile Glu Arg Gly Val
    130

<210> SEQ ID NO 20
<211> LENGTH: 131
<212> TYPE: PRT
<213> ORGANISM: Synechocystis PCC6803

<400> SEQUENCE: 20

Met Lys Phe Ile Ser Arg Leu Leu Val Ala Cys Ser Leu Leu Ile Gly
1               5                   10                  15

Leu Met Gly Phe Leu Gly Ala Asp Leu Ala Gln Ala Leu Thr Pro Asn
            20                  25                  30

Pro Ile Leu Ala Glu Leu Asn Ala Val Asp Ala Lys Leu Thr Thr Asp
        35                  40                  45

Phe Gly Gln Lys Ile Asp Leu Asn Asn Ser Asp Ile Arg Asp Phe Arg
    50                  55                  60

Gly Leu Arg Gly Phe Tyr Pro Asn Leu Ala Ser Glu Ile Ile Lys Asn
65                  70                  75                  80

Ala Pro Tyr Asp Thr Val Glu Glu Val Leu Asp Ile Pro Gly Leu Ser
                85                  90                  95

Glu Thr Gln Lys Ser Arg Leu Glu Ala Asn Leu Gly Ser Phe Thr Val
            100                 105                 110

Thr Glu Pro Ser Ile Glu Leu Thr Ser Gly Asp Asp Arg Ile Asn Pro
        115                 120                 125

Gly Val Tyr
    130

<210> SEQ ID NO 21
<211> LENGTH: 262
```

<212> TYPE: PRT
<213> ORGANISM: Halobacterium salinarum

<400> SEQUENCE: 21

Met Leu Glu Leu Leu Pro Thr Ala Val Glu Gly Val Ser Gln Ala Gln
1               5                   10                  15

Ile Thr Gly Arg Pro Glu Trp Ile Trp Leu Ala Leu Gly Thr Ala Leu
            20                  25                  30

Met Gly Leu Gly Thr Leu Tyr Phe Leu Val Lys Gly Met Gly Val Ser
        35                  40                  45

Asp Pro Asp Ala Lys Lys Phe Tyr Ala Ile Thr Thr Leu Val Pro Ala
    50                  55                  60

Ile Ala Phe Thr Met Tyr Leu Ser Met Leu Leu Gly Tyr Gly Leu Thr
65                  70                  75                  80

Met Val Pro Phe Gly Gly Glu Gln Asn Pro Ile Tyr Trp Ala Arg Tyr
                85                  90                  95

Ala Asp Trp Leu Phe Thr Thr Pro Leu Leu Leu Leu Asp Leu Ala Leu
            100                 105                 110

Leu Val Asp Ala Asp Gln Gly Thr Ile Leu Ala Leu Val Gly Ala Asp
        115                 120                 125

Gly Ile Met Ile Gly Thr Gly Leu Val Gly Ala Leu Thr Lys Val Tyr
130                 135                 140

Ser Tyr Arg Phe Val Trp Trp Ala Ile Ser Thr Ala Ala Met Leu Tyr
145                 150                 155                 160

Ile Leu Tyr Val Leu Phe Phe Gly Phe Thr Ser Lys Ala Glu Ser Met
                165                 170                 175

Arg Pro Glu Val Ala Ser Thr Phe Lys Val Leu Arg Asn Val Thr Val
            180                 185                 190

Val Leu Trp Ser Ala Tyr Pro Val Val Trp Leu Ile Gly Ser Glu Gly
        195                 200                 205

Ala Gly Ile Val Pro Leu Asn Ile Glu Thr Leu Leu Phe Met Val Leu
210                 215                 220

Asp Val Ser Ala Lys Val Gly Phe Gly Leu Ile Leu Leu Arg Ser Arg
225                 230                 235                 240

Ala Ile Phe Gly Glu Ala Glu Ala Pro Glu Pro Ser Ala Gly Asp Gly
                245                 250                 255

Ala Ala Ala Thr Ser Asp
            260

<210> SEQ ID NO 22
<211> LENGTH: 147
<212> TYPE: PRT
<213> ORGANISM: Escherichia coli

<400> SEQUENCE: 22

Met Ser Met Ser Thr Ser Thr Glu Val Ile Ala His His Trp Ala Phe
1               5                   10                  15

Ala Ile Phe Leu Ile Val Ala Ile Gly Leu Cys Cys Leu Met Leu Val
            20                  25                  30

Gly Gly Trp Phe Leu Gly Gly Arg Ala Arg Ala Arg Ser Lys Asn Val
        35                  40                  45

Pro Phe Glu Ser Gly Ile Asp Ser Val Gly Ser Ala Arg Leu Arg Leu
    50                  55                  60

Ser Ala Lys Phe Tyr Leu Val Ala Met Phe Phe Val Ile Phe Asp Val
65                  70                  75                  80

```
Glu Ala Leu Tyr Leu Phe Ala Trp Ser Thr Ser Ile Arg Glu Ser Gly
                85                  90                  95

Trp Val Gly Phe Val Glu Ala Ala Ile Phe Ile Phe Val Leu Leu Ala
            100                 105                 110

Gly Leu Val Tyr Leu Val Arg Ile Gly Ala Leu Asp Trp Thr Pro Ala
            115                 120                 125

Arg Ser Arg Arg Glu Arg Met Asn Pro Glu Thr Asn Ser Ile Ala Asn
            130                 135                 140

Arg Gln Arg
145

<210> SEQ ID NO 23

<400> SEQUENCE: 23

000

<210> SEQ ID NO 24
<211> LENGTH: 596
<212> TYPE: PRT
<213> ORGANISM: Escherichia coli

<400> SEQUENCE: 24

Met Thr Asp Leu Thr Ala Gln Glu Pro Ala Trp Gln Thr Arg Asp His
1               5                   10                  15

Leu Asp Asp Pro Val Ile Gly Glu Leu Arg Asn Arg Phe Gly Pro Asp
                20                  25                  30

Ala Phe Thr Val Gln Ala Thr Arg Thr Gly Val Pro Val Val Trp Ile
            35                  40                  45

Lys Arg Glu Gln Leu Leu Glu Val Gly Asp Phe Leu Lys Lys Leu Pro
    50                  55                  60

Lys Pro Tyr Val Met Leu Phe Asp Leu His Gly Met Asp Glu Arg Leu
65                  70                  75                  80

Arg Thr His Arg Glu Gly Leu Pro Ala Ala Asp Phe Ser Val Phe Tyr
                85                  90                  95

His Leu Ile Ser Ile Asp Arg Asn Arg Asp Ile Met Leu Lys Val Ala
                100                 105                 110

Leu Ala Glu Asn Asp Leu His Val Pro Thr Phe Thr Lys Leu Phe Pro
            115                 120                 125

Asn Ala Asn Trp Tyr Glu Arg Glu Thr Trp Asp Leu Phe Gly Ile Thr
    130                 135                 140

Phe Asp Gly His Pro Asn Leu Arg Arg Ile Met Met Pro Gln Thr Trp
145                 150                 155                 160

Lys Gly His Pro Leu Arg Lys Asp Tyr Pro Ala Arg Ala Thr Glu Phe
                165                 170                 175

Ser Pro Phe Glu Leu Thr Lys Ala Lys Gln Asp Leu Glu Met Glu Ala
                180                 185                 190

Leu Thr Phe Lys Pro Glu Glu Trp Gly Met Lys Arg Gly Thr Glu Asn
            195                 200                 205

Glu Asp Phe Met Phe Leu Asn Leu Gly Pro Asn His Pro Ser Ala His
    210                 215                 220

Gly Ala Phe Arg Ile Val Leu Gln Leu Asp Gly Glu Glu Ile Val Asp
225                 230                 235                 240

Cys Val Pro Asp Ile Gly Tyr His His Arg Gly Ala Glu Lys Met Gly
                245                 250                 255

Glu Arg Gln Ser Trp His Ser Tyr Ile Pro Tyr Thr Asp Arg Ile Glu
```

```
            260                 265                 270
Tyr Leu Gly Gly Cys Val Asn Glu Met Pro Tyr Val Leu Ala Val Glu
        275                 280                 285

Lys Leu Ala Gly Ile Thr Val Pro Asp Arg Val Asn Val Ile Arg Val
290                 295                 300

Met Leu Ser Glu Leu Phe Arg Ile Asn Ser His Leu Leu Tyr Ile Ser
305                 310                 315                 320

Thr Phe Ile Gln Asp Val Gly Ala Met Thr Pro Val Phe Phe Ala Phe
                325                 330                 335

Thr Asp Arg Gln Lys Ile Tyr Asp Leu Val Glu Ala Ile Thr Gly Phe
            340                 345                 350

Arg Met His Pro Ala Trp Phe Arg Ile Gly Gly Val Ala His Asp Leu
        355                 360                 365

Pro Arg Gly Trp Asp Arg Leu Leu Arg Glu Phe Leu Asp Trp Met Pro
    370                 375                 380

Lys Arg Leu Ala Ser Tyr Glu Lys Ala Ala Leu Gln Asn Thr Ile Leu
385                 390                 395                 400

Lys Gly Arg Ser Gln Gly Val Ala Ala Tyr Gly Ala Lys Glu Ala Leu
                405                 410                 415

Glu Trp Gly Thr Thr Gly Ala Gly Leu Arg Ala Thr Gly Ile Asp Phe
            420                 425                 430

Asp Val Arg Lys Ala Arg Pro Tyr Ser Gly Tyr Glu Asn Phe Asp Phe
        435                 440                 445

Glu Ile Pro Val Gly Gly Val Ser Asp Cys Tyr Thr Arg Val Met
    450                 455                 460

Leu Lys Val Glu Glu Leu Arg Gln Ser Leu Arg Ile Leu Glu Gln Cys
465                 470                 475                 480

Leu Asn Asn Met Pro Glu Gly Pro Phe Lys Ala Asp His Pro Leu Thr
                485                 490                 495

Thr Pro Pro Lys Glu Arg Thr Leu Gln His Ile Glu Thr Leu Ile
            500                 505                 510

Thr His Phe Leu Gln Val Ser Trp Gly Pro Val Met Pro Ala Asn Glu
        515                 520                 525

Ser Phe Gln Met Ile Glu Ala Thr Lys Gly Ile Asn Ser Tyr Tyr Leu
    530                 535                 540

Thr Ser Asp Gly Ser Thr Met Ser Tyr Arg Thr Arg Val Arg Thr Pro
545                 550                 555                 560

Ser Phe Ala His Leu Gln Gln Ile Pro Ala Ala Ile Arg Gly Ser Leu
                565                 570                 575

Val Ser Asp Leu Ile Val Tyr Leu Gly Ser Ile Asp Phe Val Met Ser
            580                 585                 590

Asp Val Asp Arg
        595

<210> SEQ ID NO 25
<211> LENGTH: 166
<212> TYPE: PRT
<213> ORGANISM: Escherichia coli

<400> SEQUENCE: 25

Met His Glu Asn Gln Gln Pro Gln Thr Glu Ala Phe Glu Leu Ser Ala
1               5                   10                  15

Ala Glu Arg Glu Ala Ile Glu His Glu Met His His Tyr Glu Asp Pro
            20                  25                  30
```

-continued

```
Arg Ala Ala Ser Ile Glu Ala Leu Lys Ile Val Gln Lys Gln Arg Gly
         35                  40                  45

Trp Val Pro Asp Gly Ala Ile His Ala Ile Ala Asp Val Leu Gly Ile
 50                  55                  60

Pro Ala Ser Asp Val Glu Gly Val Ala Thr Phe Tyr Ser Gln Ile Phe
 65                  70                  75                  80

Arg Gln Pro Val Gly Arg His Val Ile Arg Tyr Cys Asp Ser Val Val
                 85                  90                  95

Cys His Ile Asn Gly Tyr Gln Gly Ile Gln Ala Ala Leu Glu Lys Lys
            100                 105                 110

Leu Asn Ile Lys Pro Gly Gln Thr Thr Phe Asp Gly Arg Phe Thr Leu
        115                 120                 125

Leu Pro Thr Cys Cys Leu Gly Asn Cys Asp Lys Gly Pro Asn Met Met
130                 135                 140

Ile Asp Glu Asp Thr His Ala His Leu Thr Pro Glu Ala Ile Pro Glu
145                 150                 155                 160

Leu Leu Glu Arg Tyr Lys
                165
```

<210> SEQ ID NO 26
<211> LENGTH: 445
<212> TYPE: PRT
<213> ORGANISM: Escherichia coli

<400> SEQUENCE: 26

```
Met Lys Asn Ile Ile Arg Thr Pro Glu Thr His Pro Leu Thr Trp Arg
 1               5                  10                  15

Leu Arg Asp Asp Lys Gln Pro Val Trp Leu Asp Glu Tyr Arg Ser Lys
             20                  25                  30

Asn Gly Tyr Glu Gly Ala Arg Lys Ala Leu Thr Gly Leu Ser Pro Asp
         35                  40                  45

Glu Ile Val Asn Gln Val Lys Asp Ala Gly Leu Lys Gly Arg Gly Gly
 50                  55                  60

Ala Gly Phe Ser Thr Gly Leu Lys Trp Ser Leu Met Pro Lys Asp Glu
 65                  70                  75                  80

Ser Met Asn Ile Arg Tyr Leu Leu Cys Asn Ala Asp Glu Met Glu Pro
                 85                  90                  95

Gly Thr Tyr Lys Asp Arg Leu Leu Met Glu Gln Leu Pro His Leu Leu
            100                 105                 110

Val Glu Gly Met Leu Ile Ser Ala Phe Ala Leu Lys Ala Tyr Arg Gly
        115                 120                 125

Tyr Ile Phe Leu Arg Gly Glu Tyr Ile Glu Ala Ala Val Asn Leu Arg
130                 135                 140

Arg Ala Ile Ala Glu Ala Thr Glu Ala Gly Leu Leu Gly Lys Asn Ile
145                 150                 155                 160

Met Gly Thr Gly Phe Asp Phe Glu Leu Phe Val His Thr Gly Ala Gly
                165                 170                 175

Arg Tyr Ile Cys Gly Glu Glu Thr Ala Leu Ile Asn Ser Leu Glu Gly
            180                 185                 190

Arg Arg Ala Asn Pro Arg Ser Lys Pro Pro Phe Pro Ala Thr Ser Gly
        195                 200                 205

Ala Trp Gly Lys Pro Thr Cys Val Asn Asn Val Glu Thr Leu Cys Asn
210                 215                 220

Val Pro Ala Ile Leu Ala Asn Gly Val Glu Trp Tyr Gln Asn Ile Ser
225                 230                 235                 240
```

-continued

```
Lys Ser Lys Asp Ala Gly Thr Lys Leu Met Gly Phe Ser Gly Arg Val
            245                 250                 255
Lys Asn Pro Gly Leu Trp Glu Leu Pro Phe Gly Thr Thr Ala Arg Glu
        260                 265                 270
Ile Leu Glu Asp Tyr Ala Gly Met Arg Asp Gly Leu Lys Phe Lys
            275                 280                 285
Ala Trp Gln Pro Gly Ala Gly Thr Asp Phe Leu Thr Glu Ala His
    290                 295                 300
Leu Asp Leu Pro Met Glu Phe Glu Ser Ile Gly Lys Ala Gly Ser Arg
305                 310                 315                 320
Leu Gly Thr Ala Leu Ala Met Ala Val Asp His Glu Ile Asn Met Val
                325                 330                 335
Ser Leu Val Arg Asn Leu Glu Glu Phe Phe Ala Arg Glu Ser Cys Gly
            340                 345                 350
Trp Cys Thr Pro Cys Arg Asp Gly Leu Pro Trp Ser Val Lys Ile Leu
        355                 360                 365
Arg Ala Leu Glu Arg Gly Glu Gly Gln Pro Gly Asp Ile Glu Thr Leu
    370                 375                 380
Glu Gln Leu Cys Arg Phe Leu Gly Pro Gly Lys Thr Phe Cys Ala His
385                 390                 395                 400
Ala Pro Gly Ala Val Glu Pro Leu Gln Ser Ala Ile Lys Tyr Phe Arg
                405                 410                 415
Glu Glu Phe Glu Ala Gly Ile Lys Gln Pro Phe Ser Asn Thr His Leu
            420                 425                 430
Ile Asn Gly Ile Gln Pro Asn Leu Leu Lys Glu Arg Trp
        435                 440                 445

<210> SEQ ID NO 27
<211> LENGTH: 908
<212> TYPE: PRT
<213> ORGANISM: Escherichia coli

<400> SEQUENCE: 27

Met Ala Thr Ile His Val Asp Gly Lys Glu Tyr Glu Val Asn Gly Ala
1               5                   10                  15
Asp Asn Leu Leu Glu Ala Cys Leu Ser Leu Gly Leu Asp Ile Pro Tyr
            20                  25                  30
Phe Cys Trp His Pro Ala Leu Gly Ser Val Gly Ala Cys Arg Gln Cys
        35                  40                  45
Ala Val Lys Gln Tyr Gln Asn Ala Glu Asp Thr Arg Gly Arg Leu Val
    50                  55                  60
Met Ser Cys Met Thr Pro Ala Ser Asp Gly Thr Phe Ile Ser Ile Asp
65                  70                  75                  80
Asp Glu Glu Ala Lys Gln Phe Arg Glu Ser Val Val Glu Trp Leu Met
                85                  90                  95
Thr Asn His Pro His Asp Cys Pro Val Cys Glu Glu Gly Gly Asn Cys
            100                 105                 110
His Leu Gln Asp Met Thr Val Met Thr Gly His Ser Phe Arg Arg Tyr
        115                 120                 125
Arg Phe Thr Lys Arg Thr His Arg Asn Gln Asp Leu Gly Pro Phe Ile
    130                 135                 140
Ser His Glu Met Asn Arg Cys Ile Ala Cys Tyr Arg Cys Val Arg Tyr
145                 150                 155                 160
Tyr Lys Asp Tyr Ala Asp Gly Thr Asp Leu Gly Val Tyr Gly Ala His
```

-continued

```
                165                 170                 175
Asp Asn Val Tyr Phe Gly Arg Pro Glu Asp Gly Thr Leu Glu Ser Glu
            180                 185                 190

Phe Ser Gly Asn Leu Val Glu Ile Cys Pro Thr Gly Val Phe Thr Asp
        195                 200                 205

Lys Thr His Ser Glu Arg Tyr Asn Arg Lys Trp Asp Met Gln Phe Ala
    210                 215                 220

Pro Ser Ile Cys Gln Gln Cys Ser Ile Gly Cys Asn Ile Ser Pro Gly
225                 230                 235                 240

Glu Arg Tyr Gly Glu Leu Arg Arg Ile Glu Asn Arg Tyr Asn Gly Thr
                245                 250                 255

Val Asn His Tyr Phe Leu Cys Asp Arg Gly Arg Phe Gly Tyr Gly Tyr
            260                 265                 270

Val Asn Leu Lys Asp Arg Pro Arg Gln Pro Val Gln Arg Arg Gly Asp
        275                 280                 285

Asp Phe Ile Thr Leu Asn Ala Glu Gln Ala Met Gln Gly Ala Ala Asp
    290                 295                 300

Ile Leu Arg Gln Ser Lys Lys Val Ile Gly Ile Gly Ser Pro Arg Ala
305                 310                 315                 320

Ser Val Glu Ser Asn Phe Ala Leu Arg Glu Leu Val Gly Glu Glu Asn
                325                 330                 335

Phe Tyr Thr Gly Ile Ala His Gly Glu Gln Glu Arg Leu Gln Leu Ala
            340                 345                 350

Leu Lys Val Leu Arg Glu Gly Gly Ile Tyr Thr Pro Ala Leu Arg Glu
        355                 360                 365

Ile Glu Ser Tyr Asp Ala Val Leu Val Leu Gly Glu Asp Val Thr Gln
    370                 375                 380

Thr Gly Ala Arg Val Ala Leu Ala Val Arg Gln Ala Val Lys Gly Lys
385                 390                 395                 400

Ala Arg Glu Met Ala Ala Gln Lys Val Ala Asp Trp Gln Ile Ala
                405                 410                 415

Ala Ile Leu Asn Ile Gly Gln Arg Ala Lys His Pro Leu Phe Val Thr
            420                 425                 430

Asn Val Asp Asp Thr Arg Leu Asp Asp Ile Ala Ala Trp Thr Tyr Arg
        435                 440                 445

Ala Pro Val Glu Asp Gln Ala Arg Leu Gly Phe Ala Ile Ala His Ala
    450                 455                 460

Leu Asp Asn Ser Ala Pro Ala Val Asp Gly Ile Glu Pro Glu Leu Gln
465                 470                 475                 480

Ser Lys Ile Asp Val Ile Val Gln Ala Leu Ala Gly Ala Lys Lys Pro
                485                 490                 495

Leu Ile Ile Ser Gly Thr Asn Ala Gly Ser Leu Glu Val Ile Gln Ala
            500                 505                 510

Ala Ala Asn Val Ala Lys Ala Leu Lys Gly Arg Gly Ala Asp Val Gly
        515                 520                 525

Ile Thr Met Ile Ala Arg Ser Val Asn Ser Met Gly Leu Gly Ile Met
    530                 535                 540

Gly Gly Gly Ser Leu Glu Glu Ala Leu Thr Glu Leu Glu Thr Gly Arg
545                 550                 555                 560

Ala Asp Ala Val Val Val Leu Glu Asn Asp Leu His Arg His Ala Ser
                565                 570                 575

Ala Ile Arg Val Asn Ala Ala Leu Ala Lys Ala Pro Leu Val Met Val
            580                 585                 590
```

```
Val Asp His Gln Arg Thr Ala Ile Met Glu Asn Ala His Leu Val Leu
        595                 600                 605

Ser Ala Ala Ser Phe Ala Glu Ser Asp Gly Thr Val Ile Asn Asn Glu
        610                 615                 620

Gly Arg Ala Gln Arg Phe Phe Gln Val Tyr Asp Pro Ala Tyr Tyr Asp
625                 630                 635                 640

Ser Lys Thr Val Met Leu Glu Ser Trp Arg Trp Leu His Ser Leu His
                645                 650                 655

Ser Thr Leu Leu Ser Arg Glu Val Asp Trp Thr Gln Leu Asp His Val
            660                 665                 670

Ile Asp Ala Val Ala Lys Ile Pro Glu Leu Ala Gly Ile Lys Asp
            675                 680                 685

Ala Ala Pro Asp Ala Thr Phe Arg Ile Arg Gly Gln Lys Leu Ala Arg
            690                 695                 700

Glu Pro His Arg Tyr Ser Gly Arg Thr Ala Met Arg Ala Asn Ile Ser
705                 710                 715                 720

Val His Glu Pro Arg Gln Pro Gln Asp Ile Asp Thr Met Phe Thr Phe
                725                 730                 735

Ser Met Glu Gly Asn Asn Gln Pro Thr Ala His Arg Ser Gln Val Pro
            740                 745                 750

Phe Ala Trp Ala Pro Gly Trp Asn Ser Pro Gln Ala Trp Asn Lys Phe
            755                 760                 765

Gln Asp Glu Val Gly Gly Lys Leu Arg Phe Gly Asp Pro Gly Val Arg
        770                 775                 780

Leu Phe Glu Thr Ser Glu Asn Gly Leu Asp Tyr Phe Thr Ser Val Pro
785                 790                 795                 800

Ala Arg Phe Gln Pro Gln Asp Gly Lys Trp Arg Ile Ala Pro Tyr Tyr
                805                 810                 815

His Leu Phe Gly Ser Asp Glu Leu Ser Gln Arg Ala Pro Val Phe Gln
            820                 825                 830

Ser Arg Met Pro Gln Pro Tyr Ile Lys Leu Asn Pro Ala Asp Ala Ala
        835                 840                 845

Lys Leu Gly Val Asn Ala Gly Thr Arg Val Ser Phe Ser Tyr Asp Gly
        850                 855                 860

Asn Thr Val Thr Leu Pro Val Glu Ile Ala Glu Gly Leu Thr Ala Gly
865                 870                 875                 880

Gln Val Gly Leu Pro Met Gly Met Ser Gly Ile Ala Pro Val Leu Ala
                885                 890                 895

Gly Ala His Leu Glu Asp Leu Lys Glu Ala Gln Gln
            900                 905

<210> SEQ ID NO 28
<211> LENGTH: 325
<212> TYPE: PRT
<213> ORGANISM: Escherichia coli

<400> SEQUENCE: 28

Met Ser Trp Ile Ser Pro Glu Leu Ile Glu Ile Leu Thr Ile Leu
1               5                   10                  15

Lys Ala Val Val Ile Leu Leu Val Val Val Thr Cys Gly Ala Phe Met
                20                  25                  30

Ser Phe Gly Glu Arg Arg Leu Leu Gly Leu Phe Gln Asn Arg Tyr Gly
            35                  40                  45

Pro Asn Arg Val Gly Trp Gly Gly Ser Leu Gln Leu Val Ala Asp Met
```

```
                50                  55                  60
Ile Lys Met Phe Phe Lys Glu Asp Trp Ile Pro Lys Phe Ser Asp Arg
 65                  70                  75                  80

Val Ile Phe Thr Leu Ala Pro Met Ile Ala Phe Thr Ser Leu Leu Leu
                 85                  90                  95

Ala Phe Ala Ile Val Pro Val Ser Pro Gly Trp Val Val Ala Asp Leu
            100                 105                 110

Asn Ile Gly Ile Leu Phe Leu Met Met Ala Gly Leu Ala Val Tyr
            115                 120                 125

Ala Val Leu Phe Ala Gly Trp Ser Ser Asn Lys Tyr Ser Leu Leu
130                 135                 140

Gly Ala Met Arg Ala Ser Ala Gln Thr Leu Ser Tyr Glu Val Phe Leu
145                 150                 155                 160

Gly Leu Ser Leu Met Gly Val Val Ala Gln Ala Gly Ser Phe Asn Met
                165                 170                 175

Thr Asp Ile Val Asn Ser Gln Ala His Val Trp Asn Val Ile Pro Gln
            180                 185                 190

Phe Phe Gly Phe Ile Thr Phe Ala Ile Ala Gly Val Ala Val Cys His
            195                 200                 205

Arg His Pro Phe Asp Gln Pro Glu Ala Glu Gln Leu Ala Asp Gly
210                 215                 220

Tyr His Ile Glu Tyr Ser Gly Met Lys Phe Gly Leu Phe Phe Val Gly
225                 230                 235                 240

Glu Tyr Ile Gly Ile Val Thr Ile Ser Ala Leu Met Val Thr Leu Phe
                245                 250                 255

Phe Gly Gly Trp Gln Gly Pro Leu Leu Pro Pro Phe Ile Trp Phe Ala
            260                 265                 270

Leu Lys Thr Ala Phe Phe Met Met Phe Ile Leu Ile Arg Ala Ser
            275                 280                 285

Leu Pro Arg Pro Arg Tyr Asp Gln Val Met Ser Phe Gly Trp Lys Ile
290                 295                 300

Cys Leu Pro Leu Thr Leu Ile Asn Leu Leu Val Thr Ala Ala Val Ile
305                 310                 315                 320

Leu Trp Gln Ala Gln
            325

<210> SEQ ID NO 29
<211> LENGTH: 180
<212> TYPE: PRT
<213> ORGANISM: Escherichia coli

<400> SEQUENCE: 29

Met Thr Leu Lys Glu Leu Leu Val Gly Phe Gly Thr Gln Val Arg Ser
 1               5                  10                  15

Ile Trp Met Ile Gly Leu His Ala Phe Ala Lys Arg Glu Thr Arg Met
                20                  25                  30

Tyr Pro Glu Glu Pro Val Tyr Leu Pro Pro Arg Tyr Gly Arg Ile
             35                  40                  45

Val Leu Thr Arg Asp Pro Asp Gly Glu Arg Cys Val Ala Cys Asn
 50                  55                  60

Leu Cys Ala Val Ala Cys Pro Val Gly Cys Ile Ser Leu Gln Lys Ala
 65                  70                  75                  80

Glu Thr Lys Asp Gly Arg Trp Tyr Pro Glu Phe Phe Arg Ile Asn Phe
                 85                  90                  95
```

-continued

Ser Arg Cys Ile Phe Cys Gly Leu Cys Glu Ala Cys Pro Thr Thr
            100                 105                 110

Ala Ile Gln Leu Thr Pro Asp Phe Glu Met Gly Glu Tyr Lys Arg Gln
        115                 120                 125

Asp Leu Val Tyr Glu Lys Glu Asp Leu Leu Ile Ser Gly Pro Gly Lys
    130                 135                 140

Tyr Pro Glu Tyr Asn Phe Tyr Arg Met Ala Gly Met Ala Ile Asp Gly
145                 150                 155                 160

Lys Asp Lys Gly Glu Ala Glu Asn Glu Ala Lys Pro Ile Asp Val Lys
                165                 170                 175

Ser Leu Leu Pro
            180

<210> SEQ ID NO 30
<211> LENGTH: 184
<212> TYPE: PRT
<213> ORGANISM: Escherichia coli

<400> SEQUENCE: 30

Met Glu Phe Ala Phe Tyr Ile Cys Gly Leu Ile Ala Ile Leu Ala Thr
1               5                   10                  15

Leu Arg Val Ile Thr His Thr Asn Pro Val His Ala Leu Leu Tyr Leu
            20                  25                  30

Ile Ile Ser Leu Leu Ala Ile Ser Gly Val Phe Phe Ser Leu Gly Ala
        35                  40                  45

Tyr Phe Ala Gly Ala Leu Glu Ile Ile Val Tyr Ala Gly Ala Ile Met
    50                  55                  60

Val Leu Phe Val Phe Val Met Met Leu Asn Leu Gly Gly Ser Glu
65                  70                  75                  80

Ile Glu Gln Glu Arg Gln Trp Leu Lys Pro Gln Val Trp Ile Gly Pro
                85                  90                  95

Ala Ile Leu Ser Ala Ile Met Leu Val Val Ile Val Tyr Ala Ile Leu
            100                 105                 110

Gly Val Asn Asp Gln Gly Ile Asp Gly Thr Pro Ile Ser Ala Lys Ala
        115                 120                 125

Val Gly Ile Thr Leu Phe Gly Pro Tyr Val Leu Ala Val Glu Leu Ala
    130                 135                 140

Ser Met Leu Leu Leu Ala Gly Leu Val Val Ala Phe His Val Gly Arg
145                 150                 155                 160

Glu Glu Arg Ala Gly Glu Val Leu Ser Asn Arg Lys Asp Asp Ser Ala
                165                 170                 175

Lys Arg Lys Thr Glu Glu His Ala
            180

<210> SEQ ID NO 31
<211> LENGTH: 100
<212> TYPE: PRT
<213> ORGANISM: Escherichia coli

<400> SEQUENCE: 31

Met Ile Pro Leu Gln His Gly Leu Ile Leu Ala Ala Ile Leu Phe Val
1               5                   10                  15

Leu Gly Leu Thr Gly Leu Val Ile Arg Arg Asn Leu Leu Phe Met Leu
            20                  25                  30

Ile Gly Leu Glu Ile Met Ile Asn Ala Ser Ala Leu Ala Phe Val Val
        35                  40                  45

Ala Gly Ser Tyr Trp Gly Gln Thr Asp Gly Gln Val Met Tyr Ile Leu
 50                  55                  60

Ala Ile Ser Leu Ala Ala Glu Ala Ser Ile Gly Leu Ala Leu Leu
 65                  70                  75                  80

Leu Gln Leu His Arg Arg Gln Asn Leu Asn Ile Asp Ser Val Ser
                 85                  90                  95

Glu Met Arg Gly
            100

<210> SEQ ID NO 32
<211> LENGTH: 613
<212> TYPE: PRT
<213> ORGANISM: Escherichia coli

<400> SEQUENCE: 32

Met Asn Met Leu Ala Leu Thr Ile Ile Leu Pro Leu Ile Gly Phe Val
 1               5                   10                  15

Leu Leu Ala Phe Ser Arg Gly Arg Trp Ser Glu Asn Val Ser Ala Ile
             20                  25                  30

Val Gly Val Gly Ser Val Gly Leu Ala Ala Leu Val Thr Ala Phe Ile
         35                  40                  45

Gly Val Asp Phe Phe Ala Asn Gly Glu Gln Thr Tyr Ser Gln Pro Leu
 50                  55                  60

Trp Thr Trp Met Ser Val Gly Asp Phe Asn Ile Gly Phe Asn Leu Val
 65                  70                  75                  80

Leu Asp Gly Leu Ser Leu Thr Met Leu Ser Val Val Thr Gly Val Gly
                 85                  90                  95

Phe Leu Ile His Met Tyr Ala Ser Trp Tyr Met Arg Gly Glu Glu Gly
            100                 105                 110

Tyr Ser Arg Phe Phe Ala Tyr Thr Asn Leu Phe Ile Ala Ser Met Val
        115                 120                 125

Val Leu Val Leu Ala Asp Asn Leu Leu Leu Met Tyr Leu Gly Trp Glu
130                 135                 140

Gly Val Gly Leu Cys Ser Tyr Leu Leu Ile Gly Phe Tyr Tyr Thr Asp
145                 150                 155                 160

Pro Lys Asn Gly Ala Ala Met Lys Ala Phe Val Val Thr Arg Val
                165                 170                 175

Gly Asp Val Phe Leu Ala Phe Ala Leu Phe Ile Leu Tyr Asn Glu Leu
            180                 185                 190

Gly Thr Leu Asn Phe Arg Glu Met Val Glu Leu Ala Pro Ala His Phe
        195                 200                 205

Ala Asp Gly Asn Asn Met Leu Met Trp Ala Thr Leu Met Leu Leu Gly
210                 215                 220

Gly Ala Val Gly Lys Ser Ala Gln Leu Pro Leu Gln Thr Trp Leu Ala
225                 230                 235                 240

Asp Ala Met Ala Gly Pro Thr Pro Val Ser Ala Leu Ile His Ala Ala
                245                 250                 255

Thr Met Val Thr Ala Gly Val Tyr Leu Ile Ala Arg Thr His Gly Leu
            260                 265                 270

Phe Leu Met Thr Pro Glu Val Leu His Leu Val Gly Ile Val Gly Ala
        275                 280                 285

Val Thr Leu Leu Leu Ala Gly Phe Ala Ala Leu Val Gln Thr Asp Ile
290                 295                 300

Lys Arg Val Leu Ala Tyr Ser Thr Met Ser Gln Ile Gly Tyr Met Phe
305                 310                 315                 320

```
Leu Ala Leu Gly Val Gln Ala Trp Asp Ala Ile Phe His Leu Met
                325                 330                 335

Thr His Ala Phe Phe Lys Ala Leu Leu Phe Leu Ala Ser Gly Ser Val
                340                 345                 350

Ile Leu Ala Cys His His Glu Gln Asn Ile Phe Lys Met Gly Gly Leu
                355                 360                 365

Arg Lys Ser Ile Pro Leu Val Tyr Leu Cys Phe Leu Val Gly Gly Ala
                370                 375                 380

Ala Leu Ser Ala Leu Pro Leu Val Thr Ala Gly Phe Phe Ser Lys Asp
385                 390                 395                 400

Glu Ile Leu Ala Gly Ala Met Ala Asn Gly His Ile Asn Leu Met Val
                405                 410                 415

Ala Gly Leu Val Gly Ala Phe Met Thr Ser Leu Tyr Thr Phe Arg Met
                420                 425                 430

Ile Phe Ile Val Phe His Gly Lys Glu Gln Ile His Ala His Ala Val
                435                 440                 445

Lys Gly Val Thr His Ser Leu Pro Leu Ile Val Leu Leu Ile Leu Ser
                450                 455                 460

Thr Phe Val Gly Ala Leu Ile Val Pro Pro Leu Gln Gly Val Leu Pro
465                 470                 475                 480

Gln Thr Thr Glu Leu Ala His Gly Ser Met Leu Thr Leu Glu Ile Thr
                485                 490                 495

Ser Gly Val Val Ala Val Gly Ile Leu Leu Ala Ala Trp Leu Trp
                500                 505                 510

Leu Gly Lys Arg Thr Leu Val Thr Ser Ile Ala Asn Ser Ala Pro Gly
                515                 520                 525

Arg Leu Leu Gly Thr Trp Trp Tyr Asn Ala Trp Gly Phe Asp Trp Leu
                530                 535                 540

Tyr Asp Lys Val Phe Val Lys Pro Phe Leu Gly Ile Ala Trp Leu Leu
545                 550                 555                 560

Lys Arg Asp Pro Leu Asn Ser Met Met Asn Ile Pro Ala Val Leu Ser
                565                 570                 575

Arg Phe Ala Gly Lys Gly Leu Leu Leu Ser Glu Asn Gly Tyr Leu Arg
                580                 585                 590

Trp Tyr Val Ala Ser Met Ser Ile Gly Ala Val Val Val Leu Ala Leu
                595                 600                 605

Leu Met Val Leu Arg
                610

<210> SEQ ID NO 33
<211> LENGTH: 509
<212> TYPE: PRT
<213> ORGANISM: Escherichia coli

<400> SEQUENCE: 33

Met Leu Leu Pro Trp Leu Ile Leu Ile Pro Phe Ile Gly Gly Phe Leu
1               5                   10                  15

Cys Trp Gln Thr Glu Arg Phe Gly Val Lys Val Pro Arg Trp Ile Ala
                20                  25                  30

Leu Ile Thr Met Gly Leu Thr Leu Ala Leu Ser Leu Gln Leu Trp Leu
                35                  40                  45

Gln Gly Gly Tyr Ser Leu Thr Gln Ser Ala Gly Ile Pro Gln Trp Gln
                50                  55                  60

Ser Glu Phe Asp Met Pro Trp Ile Pro Arg Phe Gly Ile Ser Ile His
```

```
                65                  70                  75                  80
        Leu Ala Ile Asp Gly Leu Ser Leu Leu Met Val Val Leu Thr Gly Leu
                            85                  90                  95
        Leu Gly Val Leu Ala Val Leu Cys Ser Trp Lys Glu Ile Glu Lys Tyr
                        100                 105                 110
        Gln Gly Phe Phe His Leu Asn Leu Met Trp Ile Leu Gly Gly Val Ile
                    115                 120                 125
        Gly Val Phe Leu Ala Ile Asp Met Phe Leu Phe Phe Phe Trp Glu
                130                 135                 140
        Met Met Leu Val Pro Met Tyr Phe Leu Ile Ala Leu Trp Gly His Lys
        145                 150                 155                 160
        Ala Ser Asp Gly Lys Thr Arg Ile Thr Ala Thr Lys Phe Phe Ile
                        165                 170                 175
        Tyr Thr Gln Ala Ser Gly Leu Val Met Leu Ile Ala Ile Leu Ala Leu
                    180                 185                 190
        Val Phe Val His Tyr Asn Ala Thr Gly Val Trp Thr Phe Asn Tyr Glu
                    195                 200                 205
        Glu Leu Leu Asn Thr Pro Met Ser Ser Gly Val Glu Tyr Leu Leu Met
                    210                 215                 220
        Leu Gly Phe Phe Ile Ala Phe Ala Val Lys Met Pro Val Pro Leu
        225                 230                 235                 240
        His Gly Trp Leu Pro Asp Ala His Ser Gln Ala Pro Thr Ala Gly Ser
                        245                 250                 255
        Val Asp Leu Ala Gly Ile Leu Leu Lys Thr Ala Ala Tyr Gly Leu Leu
                    260                 265                 270
        Arg Phe Ser Leu Pro Leu Phe Pro Asn Ala Ser Ala Glu Phe Ala Pro
                    275                 280                 285
        Ile Ala Met Trp Leu Gly Val Ile Gly Ile Phe Tyr Gly Ala Trp Met
                290                 295                 300
        Ala Phe Ala Gln Thr Asp Ile Lys Arg Leu Ile Ala Tyr Thr Ser Val
        305                 310                 315                 320
        Ser His Met Gly Phe Val Leu Ile Ala Ile Tyr Thr Gly Ser Gln Leu
                        325                 330                 335
        Ala Tyr Gln Gly Ala Val Ile Gln Met Ile Ala His Gly Leu Ser Ala
                    340                 345                 350
        Ala Gly Leu Phe Ile Leu Cys Gly Gln Leu Tyr Glu Arg Ile His Thr
                    355                 360                 365
        Arg Asp Met Arg Met Met Gly Gly Leu Trp Ser Lys Met Lys Trp Leu
                    370                 375                 380
        Pro Ala Leu Ser Leu Phe Phe Ala Val Ala Thr Leu Gly Met Pro Gly
        385                 390                 395                 400
        Thr Gly Asn Phe Val Gly Glu Phe Met Ile Leu Phe Gly Ser Phe Gln
                        405                 410                 415
        Val Val Pro Val Ile Thr Val Ile Ser Thr Phe Gly Leu Val Phe Ala
                    420                 425                 430
        Ser Val Tyr Ser Leu Ala Met Leu His Arg Ala Tyr Phe Gly Lys Ala
                    435                 440                 445
        Lys Ser Gln Ile Ala Ser Gln Glu Leu Pro Gly Met Ser Leu Arg Glu
                    450                 455                 460
        Leu Phe Met Ile Leu Leu Leu Val Val Leu Leu Val Leu Leu Gly Phe
        465                 470                 475                 480
        Tyr Pro Gln Pro Ile Leu Asp Thr Ser His Ser Ala Ile Gly Asn Ile
                        485                 490                 495
```

Gln Gln Trp Phe Val Asn Ser Val Thr Thr Thr Arg Pro
            500                 505

<210> SEQ ID NO 34
<211> LENGTH: 485
<212> TYPE: PRT
<213> ORGANISM: Escherichia coli

<400> SEQUENCE: 34

Met Thr Ile Thr Pro Gln Asn Leu Ile Ala Leu Leu Pro Leu Leu Ile
1               5                   10                  15

Val Gly Leu Thr Val Val Val Met Leu Ser Ile Ala Trp Arg Arg
            20                  25                  30

Asn His Phe Leu Asn Ala Thr Leu Ser Val Ile Gly Leu Asn Ala Ala
            35                  40                  45

Leu Val Ser Leu Trp Phe Val Gly Gln Ala Gly Ala Met Asp Val Thr
        50                  55                  60

Pro Leu Met Arg Val Asp Gly Phe Ala Met Leu Tyr Thr Gly Leu Val
65                  70                  75                  80

Leu Leu Ala Ser Leu Ala Thr Cys Thr Phe Ala Tyr Pro Trp Leu Glu
                85                  90                  95

Gly Tyr Asn Asp Asn Lys Asp Glu Phe Tyr Leu Val Leu Ile Ala
            100                 105                 110

Ala Leu Gly Gly Ile Leu Leu Ala Asn Ala Asn His Leu Ala Ser Leu
            115                 120                 125

Phe Leu Gly Ile Glu Leu Ile Ser Leu Pro Leu Phe Gly Leu Val Gly
        130                 135                 140

Tyr Ala Phe Arg Gln Lys Arg Ser Leu Glu Ala Ser Ile Lys Tyr Thr
145                 150                 155                 160

Ile Leu Ser Ala Ala Ser Ser Phe Leu Leu Phe Gly Met Ala Leu
                165                 170                 175

Val Tyr Ala Gln Ser Gly Asp Leu Ser Phe Val Ala Leu Gly Lys Asn
            180                 185                 190

Leu Gly Asp Gly Met Leu Asn Glu Pro Leu Leu Leu Ala Gly Phe Gly
        195                 200                 205

Leu Met Ile Val Gly Leu Gly Phe Lys Leu Ser Leu Val Pro Phe His
210                 215                 220

Leu Trp Thr Pro Asp Val Tyr Gln Gly Ala Pro Ala Pro Val Ser Thr
225                 230                 235                 240

Phe Leu Ala Thr Ala Ser Lys Ile Ala Ile Phe Gly Val Val Met Arg
                245                 250                 255

Leu Phe Leu Tyr Ala Pro Val Gly Asp Ser Glu Ala Ile Arg Val Val
            260                 265                 270

Leu Ala Ile Ile Ala Phe Ala Ser Ile Ile Phe Gly Asn Leu Met Ala
        275                 280                 285

Leu Ser Gln Thr Asn Ile Lys Arg Leu Leu Gly Tyr Ser Ser Ile Ser
            290                 295                 300

His Leu Gly Tyr Leu Leu Val Ala Leu Ile Ala Leu Gln Thr Gly Glu
305                 310                 315                 320

Met Ser Met Glu Ala Val Gly Val Tyr Leu Ala Gly Tyr Leu Phe Ser
                325                 330                 335

Ser Leu Gly Ala Phe Gly Val Val Ser Leu Met Ser Ser Pro Tyr Arg
            340                 345                 350

Gly Pro Asp Ala Asp Ser Leu Phe Ser Tyr Arg Gly Leu Phe Trp His

```
                355                 360                 365
Arg Pro Ile Leu Ala Ala Val Met Thr Val Met Met Leu Ser Leu Ala
    370                 375                 380

Gly Ile Pro Met Thr Leu Gly Phe Ile Gly Lys Phe Tyr Val Leu Ala
385                 390                 395                 400

Val Gly Val Gln Ala His Leu Trp Trp Leu Val Gly Ala Val Val Val
                405                 410                 415

Gly Ser Ala Ile Gly Leu Tyr Tyr Tyr Leu Arg Val Ala Val Ser Leu
                420                 425                 430

Tyr Leu His Ala Pro Glu Gln Pro Gly Arg Asp Ala Pro Ser Asn Trp
            435                 440                 445

Gln Tyr Ser Ala Gly Gly Ile Val Val Leu Ile Ser Ala Leu Leu Val
        450                 455                 460

Leu Val Leu Gly Val Trp Pro Gln Pro Leu Ile Ser Ile Val Arg Leu
465                 470                 475                 480

Ala Met Pro Leu Met
                485
```

ARTIFICIAL ORGANELLES FOR ENZYMATIC COFACTOR REDUCTION

CROSS-REFERENCE TO RELATED APPLICATIONS

This application claims priority to U.S. Provisional Patent Application No. 62/959,001, filed on Jan. 9, 2020, which is incorporated by reference herein in its entirety.

REFERENCE TO SEQUENCE LISTING

This application is filed with a Computer Readable Form of a Sequence Listing in accordance with 37 C.F.R. § 1.821(c). The text file submitted by EFS, "217297-9001-US02_sequence_listing_5-JAN-2021_ST25.K" was created on Jan. 5, 2021, contains 34 sequences, has a file size of 70.0 Kbytes, and is incorporated by reference herein in its entirety.

TECHNICAL FIELD

Described herein are engineered organelles comprising multi-component proteins from different species incorporated into a membrane structure with interior and exterior aspects. In one embodiment the artificial organelle incorporates one or more protein complexes that absorb optical energy and catalyze electron transfer in biochemical reactions that can be used to reduce $NAD^+$ to NADH or analogues thereof.

BACKGROUND

Regeneration of enzymatic cofactors is a significant technical hurdle preventing the widespread employment of biochemical synthetic reactions as a production process for fine chemical manufacturing. The high cost of the continual replacement of enzymatic cofactors limits the economic viability of this production methodology despite potentially significant improvements in product quality and an associated reduction in environmental impact.

Oxidoreductase enzymes currently are employed for over 50% of the consumer chemicals manufactured using biocatalysts. Of the known oxidoreductase enzymes, 80% require Nicotinamide coenzymes ($NAD^+$/NADH or $NADP^+$/NADPH). This makes nicotinamide coenzymes the most frequently used cofactors for consumer chemicals that are manufactured using biocatalysts [1]. Commonly, the cost of such cofactors significantly exceeds the product value. As a result, the high cost of these cofactors prohibits the use of redox enzymatic reactions in industrial applications. To make any industrial biosynthesis process that uses oxidoreductase enzymes economically feasible the consumed cofactors must be efficiently regenerated.

NADH regeneration technologies have made numerous advances in recent decades [2]. The most adopted technology by industry is the enzymatic regeneration of NADH. However, current enzymatic methods are technically difficult to execute making them unsuitable for biosynthetic transformations. These methods require a suitable enzyme to couple to the co-substrate, the engineering of an efficient separation strategy and to designing a rational reaction route [2-5]. Moreover, these methods require excess amounts of sacrificial electron donors (e.g., 1,4-butanediol, ethanol, isopropanol); the corresponding products are discarded as waste, and many produce $CO_2$.

Natural photosynthesis has exceptional features; quantum yields near unity and environmental compatibility that scientists have strived to mimic. Attempts at constructing a photobioreactor through the pairing of a biocatalysis cycle with photocatalysis, despite their progression over recent years, still pale in comparison to the efficiency found in nature [6]. Many of these technologies fail to provide the oxidation power necessary to oxidize water (1.3 V).

NADH:ubiquinone oxidoreductase (Complex I) is the first enzyme of the respiratory chain in both bacteria and mitochondria. There are three types of Complex I which are currently known: $H^+$ or $Na^+$ ion-translocating Complex I ($NDH^{-1}$ in bacterial), $Na^+$ ion-translocating Complex I ($Na^+$ NQR), and the non-electrogenic Complex I (NDH-2) found in both prokaryotes and eukaryotes [7]. The basic properties of Complex I and its function are common to both prokaryotic and eukaryotic variants [8].

The crystal structure of the entire Complex I from *Thermus thermophilus* was recently solved [9]. The prokaryotic NDH-1 is comprised of 16 subunits containing seven $Fe_4S_4$ and two $Fe_2S_2$ iron-sulfur clusters and one bound falvin mononucleotide (FMN) with an aggregate molecular weight of 536 kDa [9]. The enzyme is divided into two major domains: the membrane bound and aqueous domains, the latter of which stands tangent to the membrane bound embedded portion giving it a L-shaped structure [10]. NDH-1 is comprised of three specialized modules: (1) The hydrophilic NADH oxidizing/reducing module (N-module); (2) the hydrophobic module responsible for proton transport (P-Module); and (3) a Q-binding domain connecting the other two modules (Q-module).

The primary role of Complex I is the catalytic transfer of two electrons through oxidation of NADH produced in catabolic pathways into the respiratory chain [10]. It is a vectorial proton pump driven by electron transfer, moving protons from the positively charged to the negatively charged side of the membrane during forward electron transport. Upon binding NADH, electrons are transferred to the bound flavin mononucleotide (FMN) and passed through seven iron-sulfur (Fe—S) clusters to reduce ubiquinone (Q) [11]. The reduced form of Q, $QH_2$ acts as a reducing agent for subsequent enzymes in the respiratory system. Coupled with the electron transfer, four protons are transported into the periplasm, assisting in the generation of the proton motive force (PMF) used for driving ATP synthase [12].

It has been reported that Complex I is a reversible machine which can utilize the proton motive force for the reduction of NAD± to NADH [13-14]. It has been reported that proton motive force-dependent electron transport can occur reducing NADH through $QH_2$. In this process Q is reduced through the oxidation of succinate by membrane bound succinate dehydrogenase [15-16].

Photosystem II (PSII) from oxygenic phototrophs is a multi-subunit pigment-protein, transmembrane protein [17]. It is embedded in the thylakoid membrane of cyanobacteria, higher plants, and algae [18]. Functioning as a light-driven Water:Quinone oxidoreductase, its primary function is charge generation. PSII is the first protein complex in the photosynthesis chain. PSII harvests solar energy producing a charge separation catalyzing the splitting of water, extracting electrons, producing $O_2$ and protons contributing to the PMF for ATP synthesis [19]. The function of PSII is highly conserved across species and between kingdoms. See e.g., Thornton et al. at 122 [20].

The primary photochemical reaction takes place within the reaction center (RC), the core of PSII. The RC is comprised of two protein subunits D1 and D2. Bound to the RC are CP43 and CP47 proteins, which are responsible for the adsorption of light energy [21]. The excitation energy adsorbed by these pigment-containing proteins is transferred to the RC [22]. These subunits contain all the cofactors involved in photochemical charge separation, Q-reduction, and the oxidation of water [22]. To drive these reactions 680 nm photons are adsorbed by P680, the primary oxidant of PSII. There are four chlorophyll a (Chla) molecules and two pheophytin a (Pheo$_{D1}$/Pheo$_{D2}$) molecules, which form P680. Excitation of P680 promotes a number of electron transfer reactions [23].

Upon excitation of a Chla, P680 is converted to a strong reducing agent P680*. Very rapidly, a Pheo molecule is reduced by P680* forming a radical pair state P680*$^-$ Phe*$^-$. Within a few picoseconds Pheo*-reduces a plastoquinone (QA) molecule tightly bound to the D2 domain producing P680*$^-$PheoQ$_A^-$. With a redox potential >1 V, P680*+ oxidizes a tyrosine residue (Yz) located in the D1 domain within nanoseconds, forming Yz*+P680PheoQA$^-$. The Yz*+P680PheoQ$_A^-$ complex is responsible for the reduction of a second plastoquinone (QB) within the D1 protein forming Yz*+P680PheoQ$_A$Q$_B^-$. The oxidized tyrosine extracts an electron and a proton from one of four manganese atoms in the oxygen evolving complex (Mn$_4$CaO$_5$) ligated to the D1 and CP43 subunits [24]. This entire process is repeated to reduce Q$_B^-$ to QB$^{-2}$, which is released into Q-pool contained within lipid bilayer following protonation to QH$_2$. Two more photochemical turnovers provide the manganese cluster with four oxidizing equivalents necessary to split the two bound water molecules [21]. The overall reaction of water oxidation by PSII is given in Equation (1) [25], wherein H$^+_N$ represents protons on the negative side of the membrane, and H$^+_P$ represents protons on the positive side of the membrane.

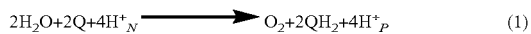

$$2H_2O+2Q+4H^+_N \longrightarrow O_2+2QH_2+4H^+_P \quad (1)$$

Both PSII and CMI use ubiquinone as an electron carrier. Ubiquinol is the fully reduced form of the molecule, which can be fully oxidized to ubiquinone or partially oxidized to semiquinone. There are many different analogues of ubiquinone, including for example decylubiquinone.

There is a need to provide biologically engineered organelle constructs comprising protein complexes from a variety of different organisms that can be used to convert light energy into reduced enzymatic cofactors.

SUMMARY

One embodiment described herein is an artificial cell free organelle system comprising: a membrane having two sides comprising an inner surface in contact with an inner aqueous medium and an outer surface in contact with an outer aqueous medium; one or more photosynthetic proteins and one or more oxidoreductase proteins are vectorially embedded within and traversing the membrane; one or more first redox active cofactors; one or more second redox active cofactors; water, and a photon energy source; wherein: when one or more photons are directed on the one or more photosynthetic proteins, the photosynthetic proteins harvest the photon energy and catalyze the oxidation of at least one water molecule in the inner aqueous medium, generating 0.5 equivalents of oxygen gas and yielding up to two protons and two electrons per two photons that are transferred to an oxidized form of the first redox active cofactor, generating a reduced form of the first redox active cofactor; the accumulation of protons in the inner aqueous medium generates a proton concentration gradient between the inner aqueous medium and the outer aqueous medium; and the one or more oxidoreductase proteins pumps protons from the inner aqueous medium through the membrane to the outer aqueous medium to reduce the proton concentration gradient and simultaneously catalyzes the transfer of electrons from the reduced first redox cofactor to an oxidized form of the second redox active cofactor, generating a reduced form of the second redox active cofactor and an oxidized form of the first redox active cofactor. In one aspect, the membrane comprises a biomimetic bilayer, a biomimetic three-dimensional bilayer, a unilamellar liposome, a planar membrane, or a membraneous polymer construct. In another aspect, the membraneous polymer construct comprises a triblock co-polymer membrane comprising varying lengths of poly (dimethylsiloxane) (PDMS) as the hydrophobic membrane-forming block and poly(2-methyloxazoline) (PMOXA) as the hydrophilic membrane-forming block. In another aspect, the membrane comprises a closed unilamellar liposome comprising a phospholipid bilayer. In another aspect, the one or more photosynthetic proteins and one or more oxidoreductase proteins are vectorially embedded in the membrane using a detergent. In another aspect, the detergent comprises one or more of CHAPS (3-[(3-cholamidopropyl) dimethylammonio]-1-propanesulfonate), DDM (n-dodecyl-β-D-maltoside), OG (octyl-β-D-glucopyranoside), or Triton X-100. In another aspect, the one or more photosynthetic proteins comprises the photosystem II complex of proteins and/or bacteriorhodopsin. In another aspect, the photosystem II complex of proteins comprises the photosystem II complexes from *Cyanobacterium synechocystis*, *Synechocystis* sp., *Synechococcus elongates*, *Thermosynechococcus elongatus*, *Thermosynechococcus vulcans*, *Pisum sativum*, *Chlamydomonas reinhardtii*, *Spinacia oleracea*, or *Arabidopsis thaliana*; and the bacteriorhodopsin comprises the bacteriorhodopsin from *Halobacterium salinarum*. In another aspect, the photosystem II complex of proteins or bacteriorhodopsin are purified or recombinant. In another aspect, the one or more photosynthetic proteins comprise the photosystem II complex of proteins from *Synechocystis* sp. PCC6803. In another aspect, the one or more oxidoreductase enzymes comprises the Respiratory Complex I complex of proteins. In another aspect, the Respiratory Complex I complex of proteins comprises the Respiratory Complex I of *Eschericia coli*, *Thermus thermophilus*, *Vibrio cholerae*, *Yarrowia lipolytica*, *Ovis aries*, *Bos taurus*, *Mus musculus*, or *Homo sapiens*. In another aspect, the Respiratory Complex I complex of proteins are purified or recombinant. In another aspect, the one or more oxidoreductase enzymes comprises the Respiratory Complex I complex of proteins from *E. coli*. In another aspect, the one or more oxidoreductase enzymes comprises a Respiratory Complex I that has been engineered to preferentially reduce NADPH. In another aspect, the one or more oxidoreductase enzymes are vectorially incorporated into the membrane in an orientation opposite to the orientation of the oxidoreductase enzyme in vivo. In another aspect, the first redox active cofactor comprises ubiquinone or a ubiquinone analogue. In another aspect, the ubiquinone analogue has the structure:

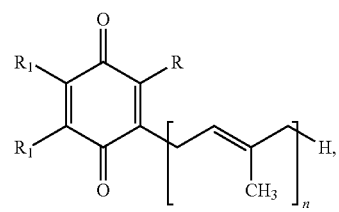

wherein R is methyl, hydroxyl, or hydrogen and $R_1$ is independently methoxy, methyl, hydroxyl or hydrogen, and n is an integer between 0 to 20, 6 to 12, or 7 to 10, including all integers within the specified ranges. In another aspect, the second redox active cofactor comprises $NAD^+$, $NADP^+$, an $NAD^+$ analogue, or an $NADP^+$ analogue. In another aspect, the $NAD^+$ or $NADP^+$ analogue has the structure:

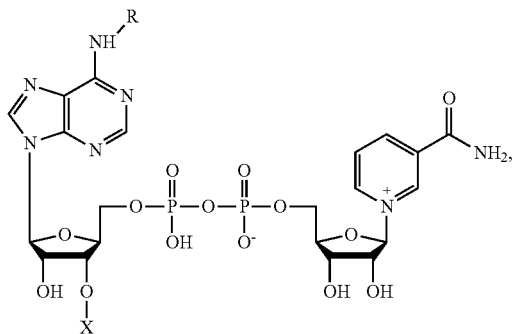

where R is a polyethylene glycol of 100 to 10,000 MW, a carbohydrate moiety or a polypeptide, and X is phosphate or hydrogen. In another aspect, the reduced form of the first redox active cofactor comprises ubiquinol, decylubiquinol, or a ubiquinol analogue. In another aspect, the ubiquinol analogue has the structure:

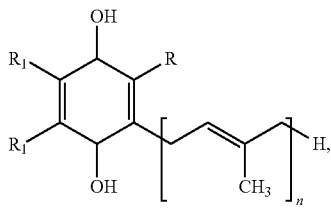

wherein R is methyl, hydroxyl, or hydrogen and $R_1$ is independently methoxy, methyl, hydroxyl or hydrogen, and n is an integer between 0 to 20, 6 to 12, or 7 to 10, including all integers within the specified ranges. In another aspect, the reduced form of the second redox active cofactor comprises NADH, NADPH, or an analogue thereof.

In another aspect, the NADH or NADPH analogue has the structure:

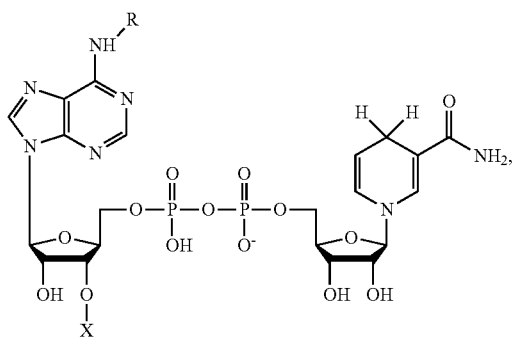

where R is a polyethylene glycol of 100 to 10,000 MW, a carbohydrate moiety, or a polypeptide, and X is phosphate or hydrogen. In another aspect, the system further comprises an ionophore comprising one or more of valinomycin, salinomycin, lasalocid, ionomycin, nonactin, beauvericin, or calcimycin. In another aspect, the system further comprises an ionophore comprising a potassium ionophore, and wherein the potassium ionophore comprises valinomycin or salinomycin.

Another embodiment described herein is a method or means for converting light energy and water into oxygen and reduced NADH, NADPH, or analogues thereof using artificial photosynthesis in an artificial cell free system, the method comprising: (a) providing an artificial cell free organelle system comprising: a membrane having two sides comprising an inner surface in contact with an inner aqueous medium and an outer surface in contact with an outer aqueous medium; one or more photosynthetic proteins comprising photosystem II or bacteriorhodopsin vectorially embedded within and traversing the membrane; one or more oxidoreductase proteins comprising Respiratory Complex I vectorially embedded within and traversing the membrane; ubiquinone or an analogue thereof; $NAD^+$, $NADP^+$ or an analogue thereof; water, and a photon energy source; (b) directing one or more photons to the one or more photosynthetic proteins; (c) the one or more photosynthetic proteins catalyzes the electron transfer from photon energy to ubiquinone or an analogue thereof, generating ubiquinol or an analogue thereof; and (d) the one or more oxidoreductase proteins catalyzes the electron transfer from ubiquinol or an analogue thereof to $NAD^+$, $NADP^+$, or analogues thereof, producing NADH, NADPH, or analogues thereof, and oxidizing ubiquinol or analogue thereof to ubiquinone or an analogue thereof. In one aspect, wherein: when one or more photons are directed on the one or more photosynthetic proteins, the photosynthetic proteins harvest the photon energy and catalyze the oxidation of at least one water molecule in the inner aqueous medium, generating 0.5 equivalents of oxygen gas and yielding up to two protons and two electrons per two photons that are transferred to ubiquinone or an analogue thereof, generating ubiquinol or an analogue thereof; the accumulation of protons in the inner aqueous medium generates a proton concentration gradient between the inner aqueous medium and the outer aqueous medium; and the oxidoreductase enzyme comprising Respiratory Complex I pumps protons from the inner aqueous medium through the membrane to the outer aqueous medium to reduce the proton concentration gradient and simultaneously catalyzes the transfer of electrons from ubiquinol or an analogue thereof to $NAD^+$, $NADP^+$, or analogues thereof, producing NADH, NADPH, or analogues thereof, and oxidizing ubiquinol or analogue thereof back to ubiquinone or a ubiquinone or an analogue thereof. In another aspect, the membrane comprises a biomimetic bilayer, a biomimetic three-dimensional bilayer, a unilamellar liposome, a planar membrane, or a membraneous polymer construct. In another aspect, the membraneous polymer construct comprises a triblock co-polymer membrane comprising varying lengths of poly(dimethylsiloxane) (PDMS) as the hydrophobic membrane-forming block and poly(2-methyloxazoline) (PMOXA) as the hydrophilic membrane-forming block. In another aspect, the membrane comprises a closed unilamellar liposome comprising a phospholipid bilayer. In another aspect, the one or more photosynthetic proteins and one or more oxidoreductase proteins are vectorially embedded in the membrane using a detergent. In another aspect, the detergent comprises one or more of CHAPS (3-[(3-cholamidopropyl)dimethylammonio]-1-propanesulfonate), DDM (n-dodecyl-β-D-maltoside), OG (octyl-β-D-glucopyranoside), or Triton X-100. In another aspect, the photosystem II complex of proteins comprises the photosystem II complexes from *Cyanobacterium synechocystis, Synechococcus elongates, Thermosynechococcus elongatus, Thermosynechococcus vulcans, Pisum sativum, Chlamydomonas reihhardtii, Spinacia oleracea,* or *Arabidopsis thaliana*; and the bacteriorhodopsin comprises the bacteriorhodopsin from *Halobacterium salinarum*. In another aspect, the photosystem II complex of proteins or bacteriorhodopsin are purified or recombinant. In another aspect, the one or more photosynthetic proteins comprise the photosystem II complex of proteins from *Cyanobacterium synechocystis*. In another aspect, the Respiratory Complex I complex of proteins comprises the Respiratory Complex I of *Eschericia coli, Thermus thermophilus, Vibrio cholerae, Yarrowia lipolytica, Ovis aries, Bos taurus, Mus musculus,* or *Homo sapiens*. In another aspect, the Respiratory Complex I complex of proteins are purified or recombinant. In another aspect, the one or more oxidoreductase enzymes comprises the Respiratory Complex I complex of proteins from *E. coli*. In another aspect, the one or more oxidoreductase enzymes comprises a Respiratory Complex I that has been engineered to preferentially reduce NADPH or an analogue thereof. In another aspect, the one or more oxidoreductase enzymes are vectorially incorporated into the membrane in an orientation opposite to the orientation of the oxidoreductase enzyme in vivo. In another aspect, the ubiquinone analogue has the structure:

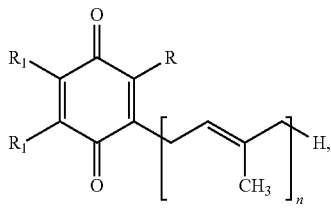

wherein R is methyl, hydroxyl, or hydrogen and $R_1$ is independently methoxy, methyl, hydroxyl or hydrogen, and n is an integer between 0 to 20, 6 to 12, or 7 to 10, including all integers within the specified ranges. In another aspect, the $NAD^+$ or $NADP^+$ analogue has the structure:

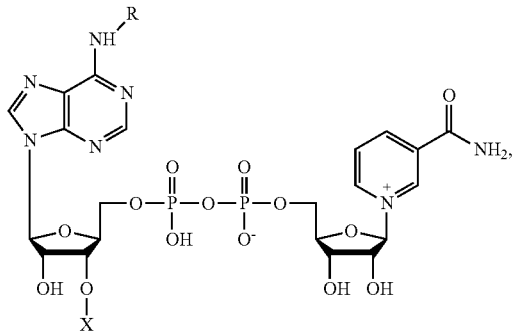

where R is a polyethylene glycol of 100 to 10,000 MW, a carbohydrate moiety or a polypeptide, and X is phosphate or hydrogen. In another aspect, the ubiquinol analogue has the structure:

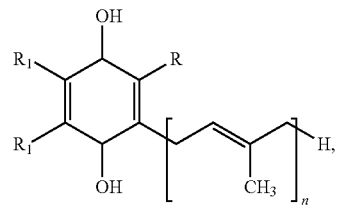

wherein R is methyl, hydroxyl, or hydrogen and $R_1$ is independently methoxy, methyl, hydroxyl or hydrogen, and n is an integer between 0 to 20, 6 to 12, or 7 to 10, including all integers within the specified ranges. In another aspect, the NADH or NADPH analogue has the structure:

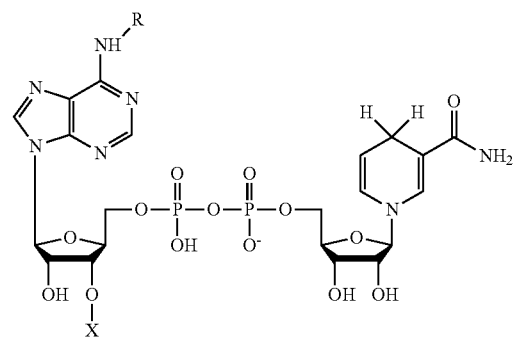

where R is a polyethylene glycol of 100 to 10,000 MW, a carbohydrate moiety, or a polypeptide, and X is phosphate or hydrogen. In another aspect, the method further comprises adding an ionophore comprising one or more of valinomycin, salinomycin, lasalocid, ionomycin, nonactin, beauvericin, or calcimycin. In another aspect, the method further comprises adding an ionophore comprising a potassium ionophore, and wherein the potassium ionophore comprises valinomycin or salinomycin.

Another embodiment described herein is NADH, NADPH, or analogues thereof produced by the methods described herein.

Another embodiment described herein is the use of an artificial cell free organelle system for converting light energy and water into oxygen and reduced NADH, NADPH, or analogues thereof using artificial photosynthesis in an artificial cell free system. In one aspect, the artificial cell free organelle system comprises: a membrane having two sides comprising an inner surface in contact with an inner aqueous medium and an outer surface in contact with an outer aqueous medium; one or more photosynthetic proteins comprising photosystem II or bacteriorhodopsin vectorially embedded within and traversing the membrane; one or more oxidoreductase proteins comprising Respiratory Complex I vectorially embedded within and traversing the membrane; ubiquinone or an analogue thereof; $NAD^+$, $NADP^+$ or an analogue thereof; water, and a photon energy source; wherein: the one or more photosynthetic proteins catalyzes the electron transfer from photon energy to ubiquinone or an analogue thereof, generating ubiquinol or an analogue thereof; and the one or more oxidoreductase proteins catalyzes the electron transfer from ubiquinol or an analogue thereof to $NAD^+$, $NADP^+$, or analogues thereof, producing NADH, NADPH, or analogues thereof, and oxidizing ubiquinol or analogue thereof to ubiquinone or an analogue thereof.

BRIEF DESCRIPTION OF THE DRAWINGS

Exemplary embodiments are illustrated in referenced figures of the drawings. It is intended that the embodiments and figures disclosed herein are to be considered illustrative rather than restrictive.

FIG. 2A shows a representative nickel affinity chromatogram. Solid dashed, and dotted lines represent absorbance at 280, 420, and 605 nm, respectively; the dashed-dotted line is the imidazole concentration. FIG. 2B shows a chromatogram on a HiLoad 16/600 Superdex 200 column. The black bars indicate fractions used in subsequent steps.

FIG. 4A shows the chromatogram from nickel affinity chromatography. The solid line, dashed line, and dotted line represent absorbance at 280, 480 and 673 nm, respectively. The dashed line overlaid with black dash-dot line is the imidazole concentration. FIG. 4B shows a chromatogram on a Superose 6 Increase 10/300 column to confirm purity. The black bar indicates fractions used in subsequent steps.

FIG. 5A shows the $NAD^+$ reduction rate vs. quantum flux of PCR-4 proteoliposomes with and without inhibition by DCMU. FIG. 5B shows the $NAD^+$ reduction rate of PCR-4 proteoliposomes with at 3000 µmol photons $s^{-1}$ $m^{-2}$ with linear equation fit for the first 3 minutes and exponential fit over 20 minutes of illumination. FIG. 5C shows the rates of $H^+$ consumption by CMI and production by PSII at 3,000 µmol photons $s^{-1}$ $m^{-2}$.

FIG. 8A shows NADH concentration and FIG. 8B shows ACMA signal for PCR-4 proteoliposomes (solid lines) and empty liposomes without protein (dashed lines). The results are the representation of three technical repeats of single biological replicate.

FIG. 9A shows NADH:DQ oxidoreductase (nmol NADH mg $CMI^{-1}$) activity of proteoliposomes with PCR-4 without DCMU and FIG. 9B shows results with DCMU. FIG. 9C shows the percent change in ACMA fluorescence of proteoliposomes without DCMU and FIG. 9D shows the results with DCMU. The light or dark condition is indicated along the top x-axis. The error bars represent the SEM of N biological replicates with three technical replicates for FIGS. 9A-D and N biological replicates.

FIG. 11A shows NADH:DQ oxidoreductase activity of PCR-4 proteoliposomes (nmol NADH mg $CMI^{-1}$) versus time (min). The light or dark condition is indicated along the top x-axis. FIG. 11B shows $NAD^+$ reduction rate (nmol NADH $min^{-1}$ mg $CMI^{-1}$) versus initial concentration of NADH (pmol) added. The error bars represent the SEM of N biological replicates each with three technical replicates for FIG. 11A and the standard deviation for N technical replicate for a single biological replicate for FIG. 11B.

FIG. 13A shows the NADH:DQ oxidoreductase activity versus time; after 5 minutes of incubation at 28° C., 200 µM NADH was added (indicated by the arrow) to samples that included Piericidin A, and CCCP. FIG. 13B shows ΔACMA vs. time.

FIG. 13C shows the same as FIG. 13B but at 8 minutes 5 μM CCCP was added to all samples to confirm the change in ΔACMA was caused by abolishing a proton gradient. Each trace is the mean of three technical repeats of a single biological replicate.

DETAILED DESCRIPTION

Figure 1A:
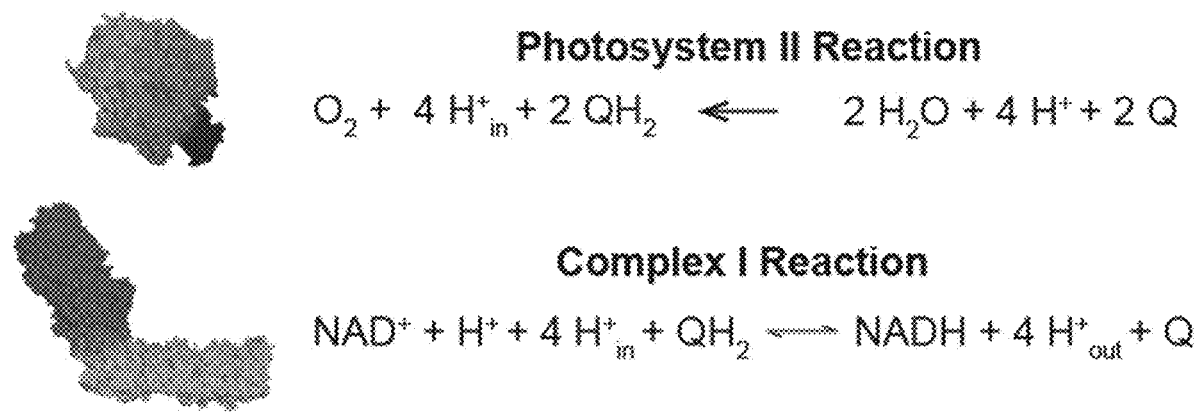
FIG. 1A is a schematic diagram showing the reactions catalyzed by Photosystem II (PSII) and Respiratory Complex I (CMI).

Unless otherwise defined, all technical and scientific terms used herein have the same meaning as commonly understood by one of ordinary skill in the art. For example, any nomenclatures used in connection with, and techniques of, cell and tissue culture, molecular biology, immunology, microbiology, genetics, and protein and nucleic acid chemistry and hybridization described herein are well known and commonly used in the art. In case of conflict, the present document, including definitions, will control. Preferred methods and materials are described below, although methods and materials similar or equivalent to those described herein can be used in practice or testing of the present invention.

As used herein, the terms "amino acid," "nucleotide," "polynucleotide," "vector," "polypeptide," and "protein" have their common meanings as would be understood by a biochemist of ordinary skill in the art. Standard single letter nucleotides (A, C, G, T, U) and standard single letter amino acids (A, C, D, E, F, G, H, I, K, L, M, N, P, Q, R, S, T, V, W, or Y) are used herein.

As used herein, the terms such as "include," "including," "contain," "containing," "having," and the like mean "comprising." The present disclosure also contemplates other embodiments "comprising," "consisting of," and "consisting essentially of," the embodiments or elements presented herein, whether explicitly set forth or not.

As used herein, the term "a," "an," "the" and similar terms used in the context of the disclosure (especially in the context of the claims) are to be construed to cover both the singular and plural unless otherwise indicated herein or clearly contradicted by the context. In addition, "a," "an," or "the" means "one or more" unless otherwise specified.

As used herein, the term "or" can be conjunctive or disjunctive.

As used herein, the term "substantially" means to a great or significant extent, but not completely.

As used herein, the term "about" or "approximately" as applied to one or more values of interest, refers to a value that is similar to a stated reference value, or within an acceptable error range for the particular value as determined by one of ordinary skill in the art, which will depend in part on how the value is measured or determined, such as the limitations of the measurement system. In one aspect, the term "about" refers to any values, including both integers and fractional components that are within a variation of up to ±10% of the value modified by the term "about." Alternatively, "about" can mean within 3 or more standard deviations, per the practice in the art. Alternatively, such as with respect to biological systems or processes, the term "about" can mean within an order of magnitude, in some embodiments within 5-fold, and in some embodiments within 2-fold, of a value. As used herein, the symbol "~" means "about" or "approximately."

All ranges disclosed herein include both end points as discrete values as well as all integers and fractions specified within the range. For example, a range of 0.1-2.0 includes 0.1, 0.2, 0.3, 0.4 . . . 2.0. If the end points are modified by the term "about," the range specified is expanded by a variation of up to ±10% of any value within the range or within 3 or more standard deviations, including the end points.

As used herein, the terms "control," or "reference" are used herein interchangeably. A "reference" or "control" level may be a predetermined value or range, which is employed as a baseline or benchmark against which to assess a measured result. "Control" also refers to control experiments or control cells.

Throughout the following description specific details are set forth in order to provide a more thorough understanding to persons skilled in the art. However, well known elements may not have been shown or described in detail to avoid unnecessarily obscuring the disclosure. Accordingly, the description and drawings are to be regarded in an illustrative, rather than a restrictive, sense.

Described herein is an artificial engineered biotic/abiotic organelle system that can be used to regenerate enzymatic cofactors. As an example, an artificial organelle was engineered to reduce $NAD^+$ using light and water, producing oxygen as a by-product, to fuel metabolic chemical synthesis. This system reduces nicotinamide coenzymes using light for energy. It sources the required electrons from water and generates oxygen as the sole by-product. This is accomplished by coupling two complex membrane proteins that do not directly interact in nature: Photosystem II and Respiratory Complex I. Through controlled vectoral assembly into an example embodiment using 180 nm lipid vesicles, these two proteins have been demonstrated to function cooperatively to yield NADH. An example embodiment of this system demonstrated reduction rates of 343.55±18.55 nmol $min^{-1}$ mg Complex $I^{-1}$ (n=7) over multiple oxidation/reduction cycles. By providing a critical enzymatic energy source that is regenerated from captured light, this technology could be applied to any isolated enzyme process that requires NADH or NADPH to produce chemicals.

As used herein, the term "vectoral" as used with reference to a membrane protein refers to a membrane protein having a specific orientation within a membrane, for example having the N-terminus of the protein always (or preferentially) on only one of the interior or the exterior of a vesicle or artificial organelle. As used with reference to a direction of transport, "vectoral" or "vectorial" means unidirectional transport from a first side of a membrane to a second side of the membrane. The term "vectoral" or "vectorially" as used with reference to the incorporation or reconstitution of a membrane protein into a membrane likewise refers to incorporating the membrane protein preferentially in a specific orientation with respect to a membrane, for example reconstituting the protein so that the N-terminus of most molecules of the protein is on only one of either the interior or the exterior of a vesicle or artificial organelle.

As used herein, "vesicle" refers to a membrane-bound fluid filled sac.

As used herein, "artificial organelle" refers to a vesicle with transmembrane proteins incorporated into the membrane of the vesicle. In one embodiment, the vesicle is a liposome.

As used herein "thermostable" means a first protein that is stable to a relatively higher temperature than a second protein. A thermostable protein may be obtained, for example, by obtaining that protein from an organism that is a thermophile or extremophile.

As used herein, the term "NAD$^+$" refers to the oxidized form of nicotinamide adenine dinucleotide and "NADH" refers to the reduced form. NAD$^+$ can be converted to NADH by the addition of two electrons and two protons as shown:

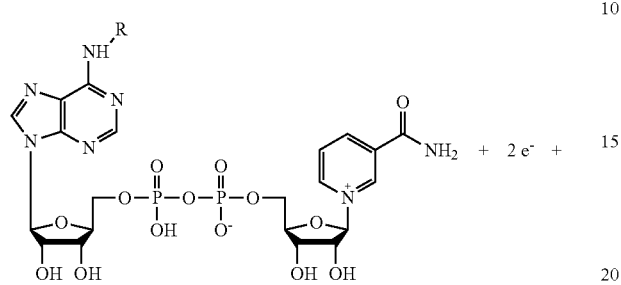

$2H^+ \rightleftharpoons$

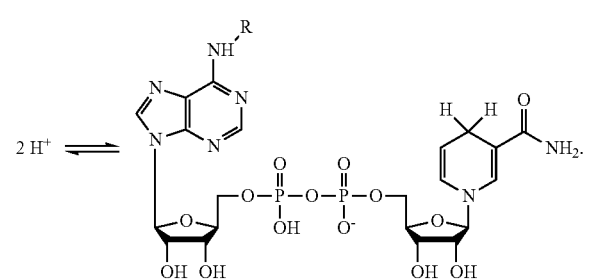

NADP$^+$ and NADPH are analagous to NAD$^+$ and NADH and have a phosphate (PO$_4$)$^{2-}$ moiety attached to the adenosine ribose 2'-hydroxyl (bolded above) forming a phosphoester linkage.

As used herein, the terms "NAD$^+$ analogue," "NADP$^+$ analogue," "NADH analogue" or "NADPH analogue" refer to a modified form of NAD$^+$, NADP$^+$, NADH, or NADPH (i.e., NADX$^+$ or NADXH, for simplicity). In one embodiment the NADX/H analogue comprises a PEGylated form of NAD(P)(H) or a conjugate of NAD(P)(H) with one or more moieties including carbohydrates or proteins. [26-27]. The modification, such as pegylation can be on the 6-amino group of adenine, as shown below in structures (1) or (2):

(1)

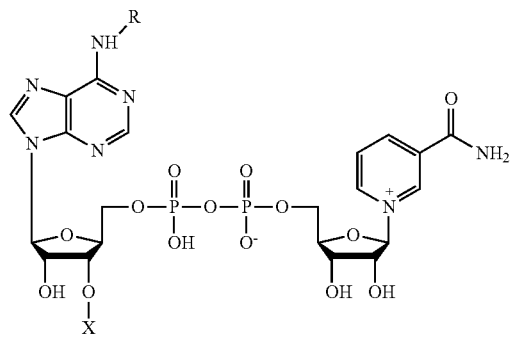

(2)

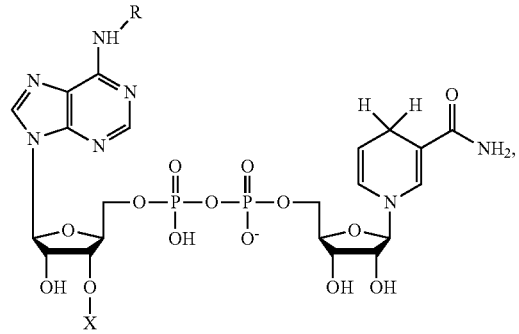

where R is a polyethylene glycol of 100 to 10,000 MW, a carbohydrate (e.g., sugar), or a polypeptide and X is a phosphate moiety or hydrogen. Other modifications include conjugates to the 2'- or 3'-hydroxyl moieties of the ribose sugars of adenosine or the nicotinamide riboside.

As used herein, the term "ubiquinone analogue" or "ubiquinol analogue" comprises compounds having the following structures (3) or (4):

(3)

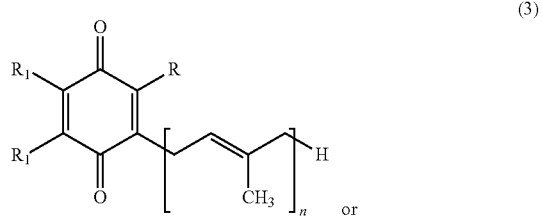

or (4)

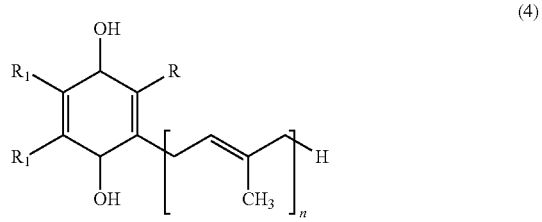

wherein R is methyl, hydroxyl, or hydrogen and R$_1$ is independently methoxy, methyl, hydroxyl or hydrogen, and n is an integer between 0 to 20, 6 to 12, or 7 to 10, including all integers within the specified ranges. Structures (3) and (4) shows a ubiquinone analogue and a ubiquinol analogue respectively but are representative of the hemi-reduced forms of ubiquinone, i.e., a "semiquinone analogue."

In one embodiment, a "ubiquinone analogue" or "ubiquinol analogue" comprises compounds having the following structures (5) or (6):

(5)

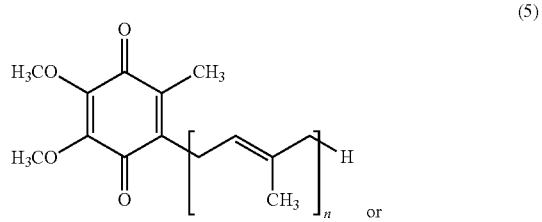

or

-continued (6)

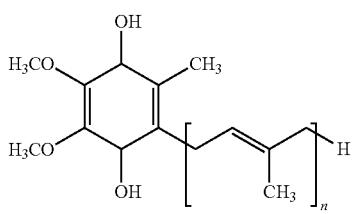

wherein n is any integer. In another embodiment, n is an integer between 6 and 12, including any value there between, e.g., 7, 8, 9, or 10. In another embodiment, n is an integer between 0 and 20, including any value there between. In another embodiment, one or more of the methyl or methoxy substituents on the benzoquinone ring is absent or comprises a different substituent group. For example, in some embodiments one or both of the methoxy groups may be absent from the benzoquinone ring or may independently be a different substituent such as a hydroxyl group. In another embodiment, the methyl group may be absent from the benzoquinone ring or may be a different substituent. Structures (5) and (6) shows ubiquinone and ubiquinol analogues but are representative of the hemi-reduced forms of ubiquinone, i.e., a "semiquinone analogue."

In one embodiment, "ubiquinone" or "Coenzyme Q" and "ubiquinol" have the following structures (7) or (8), respectively:

(7)

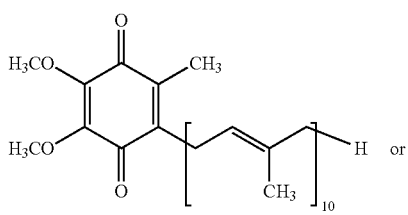

or (8)

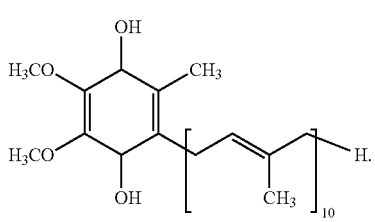

Ubiquinone has three redox states: fully oxidized (ubiquinone); partially reduced (semiquinone), and fully reduced (ubiquinol). Two electrons and two protons are required to fully reduce ubiquinone to ubiquinol as shown:

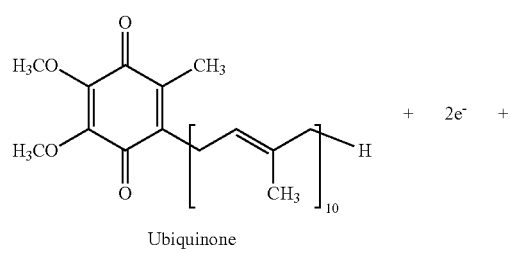

Ubiquinone

-continued

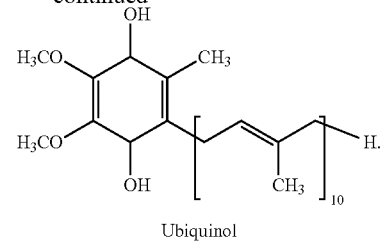

Ubiquinol

Semiquinone, not shown, is the intermediate form between a fully oxidized (ubiquinone) and fully reduced (ubiquinol) and has one hydroxyl moiety and one carbonyl moiety on the benzyl ring. As mentioned above, the analogues of ubiquinone and ubiquinol shown in structures (3)-(6) are representative of analogues of semiquinone depending on the redox state of the molecule.

Membranes suitable for use in accordance with various embodiments described herein can be any suitable material having a hydrophobic interior region surrounded by two hydrophilic regions, wherein the two hydrophilic regions are respectively in contact with aqueous solution on opposite first (e.g., inner) and second (e.g., outer) sides of the membrane. The membrane can be any suitable biomimetic membrane. The membrane can be a planar membrane or a polymer construct. For example, the membrane can be a solid substrate supported lipid or polymers with functionalized end groups which can be an azide, an alkyne, an alkene, a vinyl, an azidophenyl, or a thiol. The functionalized lipid or polymer can be coupled to a solid support surface by reaction of at least one functional group of at least one of the plurality of functionalized lipids or polymers. For example, in some embodiments the membrane comprises triblock co-polymers, which in some embodiments are in the form of a vesicle. Examples of biomimetic membranes are described by Shen et al., *J. Mem. Sci.* 454: 359-381 [28], which is incorporated by reference herein in its entirety for such teachings. In another embodiment, the triblock co-polymer comprises varying lengths of poly(dimethylsiloxane) (PDMS) as the hydrophobic membrane-forming block and poly(2-methyloxazoline) (PMOXA) as the hydrophilic membrane-forming block. In another embodiment, the membrane can be a lipid layer or a lipid bilayer. In some embodiments the membrane is in the form of a liposome. In another embodiment, the membrane comprises a unilamellar liposome. In another embodiment, the membrane comprises a closed unilamellar liposome.

In another embodiment, an engineered enzymatic cofactor regeneration system is constructed by incorporating a photosynthetic reaction center and an oxidoreductase enzyme into a membrane to use light energy to regenerate an enzymatic cofactor. In another embodiment, the photosynthetic reaction center uses energy from photons (i.e., hv or light), to: (1) split water to produce protons on a first side of the membrane to form a proton gradient from the first side of the membrane to a second side of the membrane; and (2) reduce ubiquinone (or an analogue thereof) to ubiquinol (or analogue thereof) within the hydrophobic portion of the membrane. In another embodiment, the oxidoreductase enzyme uses energy provided by the proton gradient and the ubiquinol (or analogue thereof) produced by the photosynthetic reaction center to carry out reverse electron transfer to reduce the enzymatic cofactor, thereby regenerating the enzymatic cofactor. In the process, water is used as the source of electrons to reduce the enzymatic cofactor, and oxygen is produced as a byproduct.

Any suitable method of achieving vectorial orientation of a membrane protein in a membrane can be used. Conventional approaches include mechanical means or detergent assisted reconstitution and rely on van der Waals and hydrophobic interactions to encourage the removal of detergent and embedding into the membrane material. This may be a slow process (days to weeks) and requires an external mechanical or thermodynamic force to drive detergent removal and offers limited control of transmembrane protein orientation [29]. Other methods for vectorial incorporation of membrane proteins into membranes are known. Liang et al. were the first to examine the impact of tuning electrostatic interactions between transmembrane proteins and the membrane material [30]. Transmembrane proteins are heterogeneously charged; the hydrophobic membrane spanning domains are largely anionic and the extramembrane domains comprise various charged amino acids. Using cationic lipids, transmembrane proteins can be rapidly assembled into the lipid bilayer and directed through electrostatic interactions [31]. This paradigm of charge-interaction-directed reconstitution (CIDR) translated to "rationally" designed amphiphilic block copolymers [32].

In another embodiment, the engineered enzymatic cofactor regeneration system comprises an artificial organelle, i.e., a vesicle formed from a membrane with the incorporated photosynthetic reaction center and oxidoreductase enzyme. In another embodiment, the artificial organelle comprises a proteoliposome, in which the membrane comprises a lipid bilayer membrane. In another embodiment, the artificial organelle contains a vectorially incorporated photosynthetic reaction center and a vectorially incorporated oxidoreductase enzyme. In another embodiment, the photosynthetic reaction center is oriented to produce a proton gradient from the inside to the outside of the vesicle, and the oxidoreductase enzyme is oriented to pump protons from the inside to the outside of the vesicle to carry out reverse electron transfer to reduce the enzymatic cofactor to be regenerated.

In one embodiment, the light harvesting protein is photosystem II (PSII) from any species of photosynthetic organism including plants, archaea, blue green algae, or the like. In another embodiment, the light harvesting protein is a thermostable photosystem II (PSII) from an extremophilic or thermophilic organism. In one embodiment, the light harvesting protein is photosystem II (PSII) is from *Cyanobacterium synechocystis, Synechocystis* sp., *Synechococcus elongates, Thermosynechococcus elongatus, Thermosynechococcus vulcans, Pisum sativum, Chlamydomonas reinhardtii, Spinacia oleracea*, or *Arabidopsis thaliana*.

In one embodiment, the photosynthetic reaction center is photosystem II (PSII) from *Synechocystis* sp. (strain PCC 6803).

In one embodiment, the photosynthetic reaction center is photosystem II (PSII) from *Synechocystis* sp. (strain PCC 6803) which comprises polypeptides having 90% to 100% identity to the polypeptides listed in Table 1 and SEQ ID NO: 1-20.

TABLE 1

Photosystem II Proteins *Synechocystis* sp. (strain PCC 6803)

| UNIPROT ID | Name | SEQ ID NO |
|---|---|---|
| P05429 | Photosystem II CP47 reaction center protein; 507 residues<br>MGLPWYRVHTVVLNDPGRLISVHLMHTALVAGWAGSMALYELAIFDSSDAVLNPMWRQGMFVLPFMARLGVTSSWN<br>GWSVTGETGLDPGFWSFEGVAAAHIVLSGLLFLAAVWHWVFWDLELFVDPRTGESALDLPKMFGIHLFLSGLLCFG<br>FGAFHLTGVWGPGMWVSDPYGLTGHVQPVAPEWGPAGFNPFNPGGVVAHHIAAGIVGIIAGLFHLTVRPPERLYKA<br>LRMGNIETVLSSSIAAVFFAAPVVAGTMWYGNATTPIELFGPTRYQWDKGYFQEEIQRRVDSQLAEGASLSEAWST<br>IPEKLAFYDYVGNSPAKGGLFRTGAMNSGDGIAQEWIGHPIFKDKEGRELEVRRMPNFFETFPVIMTDADGVVRAD<br>IPFRRSESKFSVEQTGVTVSFYGGALDGQTFSNPSDVKKFARKAQLGEGFDFDTETFNSDGVFRTSPRGWFTFGHA<br>VFALLFFFGHIWHGSRTLFRDVFAGVDPGLEEQVEFGVFAKVGDLSTRKEA | SEQ ID NO: 1 |
| P09193 | Photosystem II CP43 reaction center protein; 460 residues<br>MVTLSNTSMVGGRDLPSTGFAWWSGNARLINLSGKLLGAHVAHAGLIVFWAGAMTLFEVAHFIPEKPMYEQGLILL<br>PHIATLGWGVGPAGEVTDIFPFFVVGVLHLISSAVLGLGGIYHALRGPEVLEEYSSFFGYDWKDKNQMTNIIGYHL<br>ILLGCGALLLVFKAMFFGGVYDTWAPGGGDVRVITNPTLNPAIIFGYLLKAPFGGEGWIISVNNMEDIIGGHIWIG<br>LICISGGIWHILTKPFGWARRALIWSGEAYLSYSLGALSLMGFIASVFVWFNNTAYPSEFYGPTGMEASQSQAFTF<br>LVRDQRLGANIASAQGPTGLGKYLMRSPSGEIIFGGETMRFWDFRGPWLEPLRGPNGLDLDKLRNDIQPWQVRRAA<br>EYMTHAPLGSLNSVGGVITDVNSFNYVSPRAWLATSHFVLGFFFLVGHLWHAGRARAAAAGFEKGIDRETEPTLFM<br>PDLD | SEQ ID NO: 2 |
| P14835 | Photosystem II reaction center protein H; 64 residues<br>MAQRTRLGDILRPLNSEYGKVVPGWGTTPVMGVFMALFLVFLLIILQIYNSSLILEGFSVDWAG | SEQ ID NO: 3 |
| Q54697 | Photosystem II reaction center protein I; 38 residues<br>MLTLKIAVYIVVGLFISLFIFGFLSSDPTRNPGRKDFE | SEQ ID NO: 4 |
| P73070 | Photosystem II reaction center protein J; 39 residues<br>MFAEGRIPLWVVGVVAGIGAIGVLGLFFYGAYAGLGSSM | SEQ ID NO: 5 |
| P15819 | Photosystem II reaction center protein K; 45 residues<br>METIYLLAKLPEAYQIFDPLVDVLPVIPLFFLALAFVWQAAVGFK | SEQ ID NO: 6 |
| Q55354 | Photosystem II reaction center protein L; 39 residues<br>MDRNSNPNRQPVELNRTSLYLGLLLVAVLGILFSSYFFN | SEQ ID NO: 7 |
| P72701 | Photosystem II reaction center protein M; 35 residues<br>MQVNNLGFIASILFVLVPTVFLLILFIQTGKQSES | SEQ ID NO: 8 |
| P74787 | Photosystem II reaction center protein T; 31 residues<br>MESVAYILVLTMALAVLFFAIAFREPPRIEK | SEQ ID NO: 9 |

TABLE 1-continued

Photosystem II Proteins *Synechocystis* sp. (strain PCC 6803)

| UNIPROT ID | Name | SEQ ID NO |
|---|---|---|
| P72575 | Photosystem II reaction center X protein; 39 residues | SEQ ID NO: 10 |

MTPSLANFLWSLVLGAAIVLIPATVGLIFISQKDKITRS

| P73676 | Photosystem II protein Y; 39 residues | SEQ ID NO: 11 |

MDWRVIVVVSPLLIAATWAAINIGAAAIRQLQDVLGREA

| Q55438 | Photosystem II reaction center protein Ycf12; 39 residues | SEQ ID NO: 12 |

MELLAALNLEPIFQLTFLGLIVLAGPAVVFVLAFRGGDL

| P73528 | Photosystem II reaction center protein Z; 62 residues | SEQ ID NO: 13 |

MSIVFQIALAALVLFSFVMVVGVPVAYASPQNWDRSKPLLYLGSGIWAILVIVVALLNFLVV

| Q55356 | Photosystem II reaction center Psb28 protein; 112 residues | SEQ ID NO: 14 |

MAEIQFSKGVAETVVPEVRLSKSKNGQSGMAKFYFLEPTILAKESTDDITGMYLIDDEGEIITREVKGKFINGRPT
AIEATVILNSQPEWDRFMRFMERYGAENGLGFSKSE

| P07826 | Photosystem II protein D1 1; 360 residues | SEQ ID NO: 15 |

MTTTQLGLQEQSLWSRFCCWITSTSNRLYIGWFGVLMIPTLLTATTCFIIAFIAAPPVDIDGIREPIAGSLLYGNN
IITAAVVPSSNAIGLHFYPIWEAHSLDEWLYNGGPYQLIVFHFLIGIFCYLGRQWELSYRLGMRPWICVAYSAPVA
AATATLLIYSIGQGSFSDGLPLGISGTFNFMLVLQAEHNVLMHPFHMLGVAGVFGGALFAAMHGSLVTSSLIREIT
EVESQNQGYKFGQEEETYNIVAAHGYFGRLIFQYASFNNSRALHFFLGAWPVVGIWFAALAVCCFAFNLNGFNFNQ
SILDAQGRPVSTWADVINRANIGFEVMHERNVHNFPLDLASGDAQMVALNAPAIEG

| P16033 | Photosystem II protein D1 2; 360 residues | SEQ ID NO: 16 |

MITTLQQRESASLWEQFCQWVTSTNNRIYVGWFGTLMIPTLLTATTCFIIAFIAAPPVDIDGIREPVAGSLLYGNN
IISGAVVPSSNAIGLHFYPIWEAASLDEWLYNGGPYQLVVFHFLIGIFCYMGRQWELSYRLGMRPWICVAYSAPVS
AATAVFLIYPIGQGSFSDGMPLGISGTFNFMIVFQAEHNILMHPFHMLGVAGVFGGSLFSAMHGSLVTSSLVRETT
EVESQNYGYKFGQEEETYNIVAAHGYFGRLIFQYASFNNSRSLHFFLGAWPVIGIWFTAMGVSTMAFNLNGFNFNQ
SILDSQGRVIGTWADVLNRANIGFEVMHERNAHNFPLDLASGEQAPVALTAPAVNG

| P09192 | Photosystem II D2 protein; 352 residues | SEQ ID NO: 17 |

MTIAVGRAPVERGWFDVLDDWLKRDRFVFIGWSGLLLFPCAFMALGGWLIGTTFVTSWYTHGLASSYLEGANFLTV
AVSSPADAFGHSLLFLWGPEAQGNLTRWFQIGGLWPFVALHGAFGLIGFMLRQFEISRLVGIRPYNAIAFSGPIAV
FVSVFLMYPLGQSSWFFAPSFGVAGIFRFILFLQGFHNWTLNPFHMMGVAGILGGALLCAIHGATVENTLFEDGED
SNTFRAFEPTQAEETYSMVTANRFWSQIFGIAFSNKRWLHFFMLFVPVTGLWMSSVGIVGLALNLRAYDFVSQELR
AAEDPEFETFYTKNILLNEGMRAWMAPQDQPHENFIFPEEVLPRGNAL

| P10549 | Photosystem II manganese-stabilizing polypeptide; 274 residues | SEQ ID NO: 18 |

MRFRPSIVALLSVCFGLLTFLYSGSAFAVDKSQLTYDDIVNTGLANVCPEISSFTRGTIEVEPNTKYFVSDFCMEP
QEYFVKEEPVNKRQKAEYVKGKVLTRQTTSLEQIRGSIAVGADGTLTFKEKDGIDFQPITVLLPGGEEVPFFFTVK
NFTGTTEPGFTSINSSTDFVGDFNVPSYRGAGFLDPKARGLYTGYDNAVALPSAADKFRINKKETPLGKGILSLQV
TQVDGSTGEIAGIFESEQPSDTDLGAKEPLDVKVRGIFYGRVDTDV

| P74367 | Photosystem II lipoprotein Psb27; 134 residues | SEQ ID NO: 19 |

MSFLKNQLSRLLALILVVAIGLTACDSGTGLTGNYSQDTLTVIATLREAIDLPQDAPNRQEVQDTARGQINDYISR
YRRKGDAGGLKSFTTMQTALNSLAGYYTSYGARPIPEKLKKRLQLEFTQAERSIERGV

| Q55332 | Photosystem II 12 kDa extrinsic protein; 131 residues | SEQ ID NO: 20 |

MKFISRLLVACSLLIGLMGFLGADLAQALTPNPILAELNAVDAKLTTDFGQKIDLNNSDIRDFRGLRGFYPNLASE
IIKNAPYDTVEEVLDIPGLSETQKSRLEANLGSFTVTEPSIELTSGDDRINPGVY

In another embodiment, the light harvesting protein is a bacteriorhodopsin (BR), proteorhodopsin (PR), archaerhodopsin (AR), xanthorhodopsin (xR) or Gloeobacter rhodopsin (GR). In one embodiment, the bacteriorhodopsin comprises thermostable or extremophilic bacteriorhodopsin from a thermophilic or extremophilic organism. In one embodiment, the bacteriorhodopsin comprises the bacteriorhodopsin from *Halobacterium salinarum*.

In one embodiment, bacteriorhodopsin from *Halobacterium salinarum* which comprises polypeptides having 90% to 100% identity to the polypeptide listed in Table 2 and SEQ ID NO:

TABLE 2

Bacteriorhodopsin *Halobacterium salinarum* (strain ATCC 29341)

| UNIPROT ID | Name | SEQ ID NO |
|---|---|---|
| B0R5N9 | Bacteriorhodopsin; 262 residues | SEQ ID NO: 21 |

MLELLPTAVEGVSQAQITGRPEWIWLALGTALMGLGTLYFLVKGMGVSDPDAKKFYAITTLVPAIAFTMYLSMLLG
YGLTMVPFGGEQNPIYWARYADWLFTTPLLLLDLALLVDADQGTILALVGADGIMIGTGLVGALTKVYSYRFVWWA
ISTAAMLYILYVLFFGFTSKAESMRPEVASTFKVLRNVTVVLWSAYPVVWLIGSEGAGIVPLNIETLLFMVLDVSA
KVGFGLILLRSRAIFGEAEAPEPSAGDGAAATSD

In another embodiment, the oxidoreductase enzyme is respiratory complex (I) (CMI, NADH:Ubiquinone oxidoreductase), which is used to carry out reverse electron transfer to reduce the enzymatic cofactor, for example by reducing NAD⁺ to NADH. In another embodiment, the CMI is from any organism or species. In another embodiment, the CMI is thermostable CMI from an extremophilic or thermophilic organism. In another embodiment, the CMI is from *Eschericia coli, Thermus thermophilus, Vibrio cholerae, Yarrowia lipolytica, Ovis aries, Bos taurus, Mus musculus,* or *Homo sapiens*. In one embodiment, the oxidoreductase enzyme is respiratory complex (I) (CMI, NADH:Ubiquinone oxidoreductase), from *E. coli*.

In one embodiment, oxidoreductase enzyme is respiratory complex (I) (CMI, NADH:Ubiquinone oxidoreductase), from *E. coli* which comprises polypeptides having 90% to 100% identity to the polypeptides listed in Table 3 and SEQ ID NO: 22-34.

TABLE 3

Respiratory Complex I proteins *Escherichia coli* (strain K12)

| UNIPROT ID | Name | SEQ ID NO |
|---|---|---|
| P0AFC3 | NADH-quinone oxidoreductase subunit A; 147 residues | SEQ ID NO: 22 |

MSMSTSTEVIAHHWAFAIFLIVAIGLCCLMLVGGWFLGGRARARSKNVPFESGIDSVGSARLRLSAKFYLVAMFFV
IFDVEALYLFAWSTSIRESGWVGFVEAAIFIFVLLAGLVYLVRIGALDWTPARSRRERMNPETNSIANRQR

| P0AFC7 | NADH-quinone oxidoreductase subunit B; 220 residues | SEQ ID NO: 23 |

MDYTLTRIDPNGENDRYPLQKQEIVTDPLEQEVNKNVFMGKLNDMVNWGRKNSIWPYNFGLSCCYVEMVTSFTAVH
DVARFGAEVLRASPRQADLMVVAGTCFTKMAPVIQRLYDQMLEPKWVISMGACANSGGMYDIYSVVQGVDKFIPVD
VIIPGCPPRPEAYMQALMLLQESIGKERRPLSWVVGDQGVYRANMQSERERKRGERIAVTNLRTPDEI

| P33599 | NADH-quinone oxidoreductase subunit C/D; 596 residues | SEQ ID NO: 24 |

MTDLTAQEPAWQTRDHLDDPVIGELRNREGPDAFTVQATRTGVPVVWIKREQLLEVGDFLKKLPKPYVMLFDLHGM
DERLRTHREGLPAADFSVFYHLISIDRNRDIMLKVALAENDLHVPTFTKLFPNANWYERETWDLFGITFDGHPNLR
RIMMPQTWKGHPLRKDYPARATEFSPFELTKAKQDLEMEALTFKPEEWGMKRGTENEDFMELNLGPNHPSAHGAFR
IVLQLDGEEIVDCVPDIGYHHRGAEKMGERQSWHSYIPYTDRIEYLGGCVNEMPYVLAVEKLAGITVPDRVNVIRV
MLSELFRINSHLLYISTFIQDVGAMTPVFFAFTDRQKIYDLVEAITGERMHPAWFRIGGVAHDLPRGWDRLLREFL
DWMPKRLASYEKAALQNTILKGRSQGVAAYGAKEALEWGTTGAGLRATGIDFDVRKARPYSGYENFDFEIPVGGGV
SDCYTRVMLKVEELRQSLRILEQCLNNMPEGPFKADHPLTTPPPKERTLQHIETLITHFLQVSWGPVMPANESFQM
IEATKGINSYYLTSDGSTMSYRTRVRTPSFAHLQQIPAAIRGSLVSDLIVYLGSIDFVMSDVDR

| P0AFD1 | NADH-quinone oxidoreductase subunit E; 166 residues | SEQ ID NO: 25 |

MHENQQPQTEAFELSAAEREAIEHEMHHYEDPRAASIEALKIVQKQRGWVPDGAIHAIADVLGIPASDVEGVATFY
SQIFRQPVGRHVIRYCDSVVCHINGYQGIQAALEKKLNIKPGQTTFDGRFTLLPTCCLGNCDKGPNMMIDEDTHAH
LTPEAIPELLERYK

| P31979 | NADH-quinone oxidoreductase subunit F; 445 residues | SEQ ID NO: 26 |

MKNIIRTPETHPLTWRLRDDKQPVWLDEYRSKNGYEGARKALTGLSPDEIVNQVKDAGLKGRGGAGFSTGLKWSLM
PKDESMNIRYLLCNADEMEPGTYKDRLLMEQLPHLLVEGMLISAFALKAYRGYIFLRGEYIEAAVNLRRAIAEATE
AGLLGKNIMGTGFDFELFVHTGAGRYICGEETALINSLEGRRANPRSKPPFPATSGAWGKPTCVNNVETLCNVPAI
LANGVEWYQNISKSKDAGTKLMGFSGRVKNPGLWELPFGTTAREILEDYAGGMRDGLKFKAWQPGGAGTDELTEAH
LDLPMEFESIGKAGSRLGTALAMAVDHEINMVSLVRNLEEFFARESCGWCTPCRDGLPWSVKILRALERGEGQPGD
IETLEQLCRFLGPGKTFCAHAPGAVEPLQSAIKYFREEFEAGIKQPFSNTHLINGIQPNLLKERW

| P33602 | NADH-quinone oxidoreductase subunit G; 908 residues | SEQ ID NO: 27 |

MATIHVDGKEYEVNGADNLLEACLSLGLDIPYFCWHPALGSVGACRQCAVKQYQNAEDTRGRLVMSCMTPASDGTF
ISIDDEEAKQFRESVVEWLMTNHPHDCPVCEEGGNCHLQDMTVMTGHSFRRYRFTKRTHRNQDLGPFISHEMNRCI
ACYRCVRYYKDYADGTDLGVYGAHDNVYFGRPEDGTLESEFSGNLVEICPTGVFTDKTHSERYNRKWDMQFAPSIC
QQCSIGCNISPGERYGELRRIENRYNGTVNHYFLCDRGRFGYGYVNLKDRPRQPVQRRGDDFITLNAEQAMQGAAD
ILRQSKKVIGIGSPRASVESNFALRELVGEENFYTGIAHGEQERLQLALKVLREGGIYTPALREIESYDAVLVLGE
DVTQTGARVALAVRQAVKGKAREMAAAQKVADWQIAAILNIGQRAKHPLFVTNVDDTRLDDIAAWTYRAPVEDQAR
LGFAIAHALDNSAPAVDGIEPELQSKIDVIVQALAGAKKPLIISGTNAGSLEVIQAAANVAKALKGRGADVGITMI
ARSVNSMGLGIMGGGSLEEALTELETGRADAVVVLENDLHRHASAIRVNAALAKAPLVMVVDHQRTAIMENAHLVL
SAASFAESDGTVINNEGRAQRFFQVYDPAYYDSKTVMLESWRWLHSLHSTLLSREVDWTQLDHVIDAVVAKIPELA
GIKDAAPDATFRIRGQKLAREPHRYSGRTAMRANISVHEPRQPQDIDTMFTFSMEGNNQPTAHRSQVPFAWAPGWN
SPQAWNKFQDEVGGKLRFGDPGVRLFETSENGLDYFTSVPARFQPQDGKWRIAPYYHLFGSDELSQRAPVFQSRMP
QPYIKLNPADAAKLGVNAGTRVSFSYDGNTVTLPVEIAEGLTAGQVGLPMGMSGIAPVLAGAHLEDLKEAQQ

| P0AFD4 | NADH-quinone oxidoreductase subunit H; 325 residues | SEQ ID NO: 28 |

MSWISPELIEILLTILKAVVILLVVVTCGAFMSFGERRLLGLFQNRYGPNRVGWGGSLQLVADMIKMFFKEDWIPK
FSDRVIFTLAPMIAFTSLLLAFAIVPVSPGWVVADLNIGILFFLMMAGLAVYAVLFAGWSSNNKYSLLGAMRASAQ
TLSYEVFLGLSLMGVVAQAGSFNMTDIVNSQAHVWNVIPQFFGFITFAIAGVAVCHRHPFDQPEAEQELADGYHIE
YSGMKFGLFFVGEYIGIVTISALMVTLFFGGWQGPLLPPFIWFALKTAFFMMMFILIRASLPRPRYDQVMSFGWKI
CLPLTLINLLVTAAVILWQAQ

| P0AFD6 | NADH-quinone oxidoreductase subunit I; 180 residues | SEQ ID NO: 29 |

MTLKELLVGFGTQVRSIWMIGLHAFAKRETRMYPEEPVYLPPRYRGRIVLTRDPDGEERCVACNLCAVACPVGCIS
LQKAETKDGRWYPEFFRINFSRCIFCGLCEEACPTTAIQLTPDFEMGEYKRQDLVYEKEDLLISGPGKYPEYNFYR
MAGMAIDGKDKGEAENEAKPIDVKSLLP

| P0AFE0 | NADH-quinone oxidoreductase subunit J; 184 residues | SEQ ID NO: 30 |

MEFAFYICGLIAILATLRVITHINPVHALLYLIISLLAISGVFFSLGAYFAGALEIIVYAGAIMVLFVFVVMMLNL
GGSEIEQERQWLKPQVWIGPAILSAIMLVVIVYAILGVNDQGIDGTPISAKAVGITLFGPYVLAVELASMLLLAGL
VVAFHVGREERAGEVLSNRKDDSAKRKTEEHA

TABLE 3-continued

Respiratory Complex I proteins *Escherichia coli* (strain K12)

| UNIPROT ID | Name | SEQ ID NO |
|---|---|---|
| P0AFE4 | NADH-quinone oxidoreductase subunit K; 100 residues | SEQ ID NO: 31 |

MIPLQHGLILAAILFVLGLTGLVIRRNLLFMLIGLEIMINASALAFVVAGSYWGQTDGQVMYILAISLAAAEASIG
LALLLQLHRRRQNLNIDSVSEMRG

| P33607 | NADH-quinone oxidoreductase subunit L; 613 residues | SEQ ID NO: 32 |

MNMLALTIILPLIGFVLLAFSRGRWSENVSAIVGVGSVGLAALVTAFIGVDFFANGEQTYSQPLWTWMSVGDFNIG
FNLVLDGLSLTMLSVVTGVGFLIHMYASWYMRGEEGYSRFFAYTNLFIASMVVLVLADNLLLMYLGWEGVGLCSYL
LIGFYYTDPKNGAAAMKAFVVTRVGDVFLAFALFILYNELGTLNFREMVELAPAHFADGNNMLMWATLMLLGGAVG
KSAQLPLQTWLADAMAGPTPVSALIHAATMVTAGVYLIARTHGLFLMTPEVLHLVGIVGAVTLLLAGFAALVQTDI
KRVLAYSTMSQIGYMFLALGVQAWDAAIFHLMTHAFFKALLFLASGSVILACHHEQNIFKMGGLRKSIPLVYLCFL
VGGAALSALPLVTAGFFSKDEILAGAMANGHINLMVAGLVGAFMTSLYTFRMIFIVFPHGKEQIHAHAVKGVTHSLP
LIVLLILSTFVGALIVPPLQGVLPQTTELAHGSMLTLEITSGVVAVVGILLAAWLWLGKRTLVTSIANSAPGRLLG
TWWYNAWGFDWLYDKVFVKPFLGIAWLLKRDPLNSMMNIPAVLSRFAGKGLLLSENGYLRWYVASMSIGAVVVLAL
LMVLR

| P0AFE8 | NADH-quinone oxidoreductase subunit M; 409 residues | SEQ ID NO: 33 |

MLLPWLILIPFIGGFLCWQTERFGVKVPRWIALITMGLTLALSLQLWLQGGYSLTQSAGIPQWQSEFDMPWIPRFG
ISIHLAIDGLSLLMVVLTGLLGVLAVLCSWKEIEKYQGFFHLNLMWILGGVIGVFLAIDMFLFFFFWEMMLVPMYF
LIALWGHKASDGKTRITAATKFFIYTQASGLVMLIAILALVFVHYNATGVWTFNYEELLNTPMSSGVEYLLMLGFF
IAFAVKMPVVPLHGWLPDAHSQAPTAGSVDLAGILLKTAAYGLLFRSLPLFPNASAEFAPIAMWLGVIGIFYGAWM
AFAQTDIKRLIAYTSVSHMGFVLIAIYTGSQLAYQGAVIQMIAHGLSAAGLFILCGQLYERIHTRDMRMMGGLWSK
MKWLPALSLFFAVATLGMPGTGNFVGEFMILFGSFQVVPVITVISTFGLVFASVYSLAMLHRAYFGKAKSQIASQE
LPGMSLRELFMILLLVVLLVLLGFYPQPILDTSHSAIGNIQQWFVNSVITTRP

| P0AFF0 | NADH-quinone oxidoreductase subunit N; 485 residues | SEQ ID NO: 34 |

MTITPQNLIALLPLLIVGLTVVVVMLSIAWRRNHFLNATLSVIGLNAALVSLWFVGQAGAMDVTPLMRVDGFAMLY
TGLVLLASLATCTFAYPWLEGYNDNKDEFYLLVLIAALGGILLANANHLASLFLGIELISLPLFGLVGYAFRQKRS
LEASIKYTILSAAASSFLLFGMALVYAQSGDLSFVALGKNLGDGMLNEPLLLAGFGLMIVGLGFKLSLVPFHLWTP
DVYQGAPAPVSTFLATASKIAIFGVVMRLFLYAPVGDSEAIRVVLAIIAFASIIFGNLMALSQINIKRLLGYSSIS
HLGYLLVALIALQTGEMSMEAVGVYLAGYLFSSLGAFGVVSLMSSPYRGPDADSLFSYRGLFWHRPILAAVMTVMM
LSLAGIPMTLGFIGKFYVLAVGVQAHLWWLVGAVVVGSAIGLYYYLRVAVSLYLHAPEQPGRDAPSNWQYSAGGIV
VLISALLVLVLGVWPQPLISIVRLAMPLM

Other protein complexes are useful for the artificial cell free organelle systems described herein. For example, Photosystem II complexes from *Thermosynechococcus elongatus* (PBD ID: 2AXT), *Thermosynechococcus vulcanus* (PDB ID: 3WU2), *Pisum sativum* (PDB ID: 5XNL), *Chlamydomonas reinhardtii* (PDB ID: 6KAD), *Spinacia oleracea* (PDB ID: 3JCU), and *Arabidopsis thaliana* (PDB ID: 5MDX) have solved biomolecular structures and can be purified to homogeneity [56-62]; the polypeptide sequences of the structures in the indicated Protein Data Base accession numbers and publication references are incorporated by reference herein for such teachings. Similarly, oxidoreductase complex I structures have been solved for *Thermus thermophilus* (PDB ID 3IAM), *Vibrio cholerae* (PDB ID 4P6V), *Yarrowia lipolytica* (PDB ID: 6RFR), *Ova aries* (PDB ID: 6ZKJ), *Bos taurus* (PDB ID: 5LDX), *Mus musculus* (PDB ID: 6ZTQ), and *Homo sapiens* (PDB ID: SXTD) [63-68]; the polypeptide sequences of the structures in the indicated Protein Data Base accession numbers and publication references are incorporated by reference herein for such teachings. Other homologous PSII, bacteriorhodopsin, and oxidoreductase complex I proteins and protein complexes may be used in the cell free organelle systems described herein.

The proteins and protein complexes for the photosynthetic proteins or oxidoreductase proteins can be purified from their natural organisms or recombinantly expressed in typical expression organisms. Generally, with complex multiprotein complexes, it is preferable to purify the protein complex from the natural source.

In one embodiment described herein, the artificial cell free organelle system is reconstituted with a light harvesting or photosynthetic protein or protein complex from one organism and an oxidoreductase protein or protein complex from another organism. Each protein or protein complex is vectorially incorporated into an artificial membrane system. This permits precise control of the reconstitution stoichiometry, the membrane composition, buffer systems, and concentrations of the enzymatic cofactors such as ubiquinone, ubiquinol or analogues thereof and $NAD^+$, $NADP^+$, NADH, NADPH, or analogues thereof.

In one embodiment, the artificial cell free organelle system uses ubiquinone or an analogue thereof as an enzymatic cofactor or coenzyme. In another embodiment, the system uses ubiquinol, decylubiquinol, or an analogue of ubiquinol as a coenzyme.

In another embodiment, the artificial cell free organelle system uses $NAD^+$, NADH, or an analogue thereof as an enzymatic cofactor or coenzyme. In another embodiment, the enzymatic cofactor is $NADP^+$, NADPH (nicotinamide adenine dinucleotide phosphate), or an analogue thereof. For example, some researchers have produced CMI containing point mutations that increase its affinity for binding $NADP^+$/NADPH over $NAD^+$/NADH [33], and such constructs can be used to regenerate NADPH in the same manner as described with reference to the exemplary embodiment used to regenerate NADH. In one embodiment, the desired product of the artificial cell free organelle system is NADH, NADPH, or analogues thereof.

In one embodiment, water ($H_2O$) is used as the electron donor to regenerate the enzymatic cofactor. In another embodiment, oxygen ($O_2$) is essentially the only byproduct produced in the process of regenerating the enzymatic cofactor (e.g., NADH, NADPH, or analogues thereof).

In another embodiment, an ionophore, for example a potassium ionophore, is added to the reaction mixture to reduce the electrical component of the pH gradient produced by the photosynthetic reaction center, which in some embodiments allows a higher pH gradient to be established across the membrane. In another embodiment, the potassium ionophore is valinomycin. In other embodiments, the potassium ionophore is salinomycin. In other embodiments, the ionophore is lasalocid, ionomycin, nonactin, beauvericin, calcimycin, or the like.

Figure 1B:
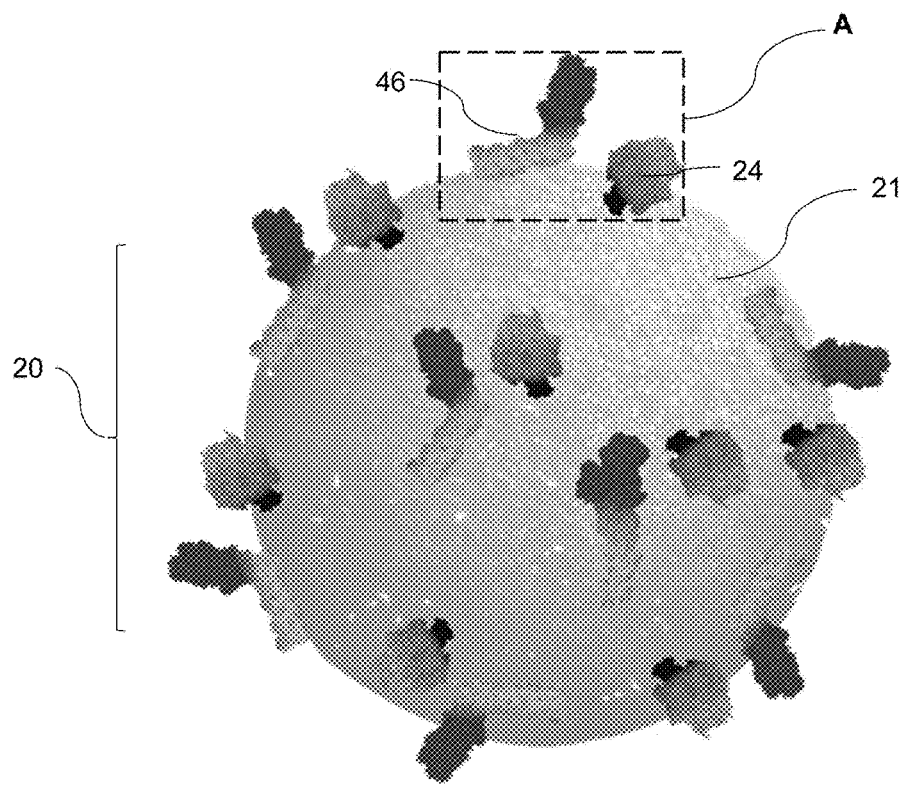
FIG. 1B shown an exemplary proteoliposome 20 comprising a membrane, which is a lipid bilayer 21 in the illustrated embodiment. The proteoliposome contains Photosystem II (PSII) 24 and Respiratory Complex I (CMI) 46 integrated into the phospholipid bilayer 21 of the membrane. An enlarged view of the area indicated as "A" is shown in FIG. 1C.
Figure 1C:
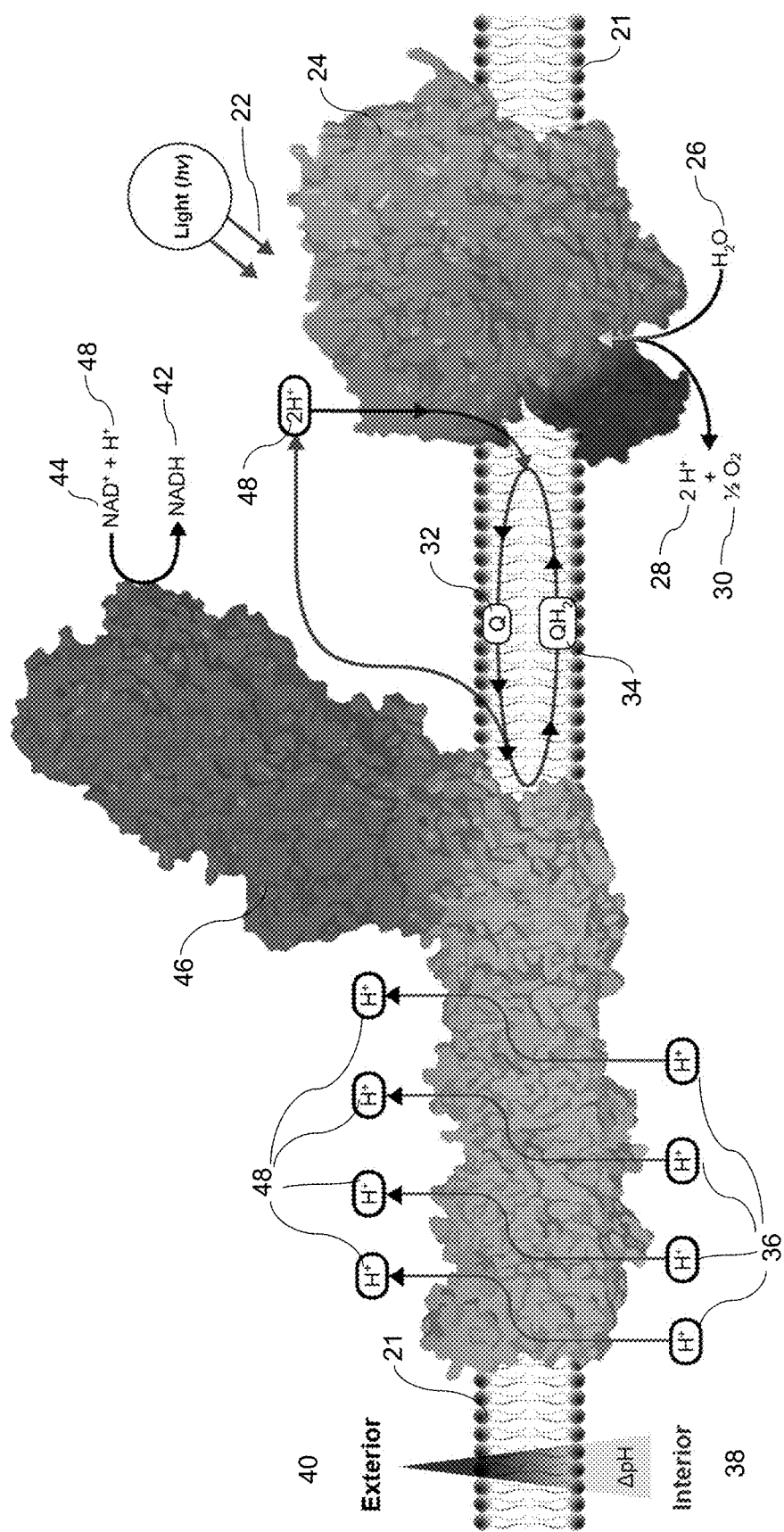
FIG. 1C shows an enlarged view of the "A" region of FIG. 1B and illustrates the specific reactions that occur on the interior 38 and exterior 40 of the phospholipid bilayer 21 of the membrane. PSII 24 harvests light energy 22, splitting water 26 to oxygen 30 and protons 28 on the inside 38 of the proteoliposome; electrons are transferred from water 26 to Q 32 to form $QH_2$ 34 within the lipid bilayer 21 of the proteoliposome. The production of 4 protons in the interior of the proteoliposomes by PSII 24 generates a PMF driving the reverse reaction of CMI 46. CMI 46 oxidizes the $QH_2$ 34 produced by PSII 24 transferring the electrons and a proton 48 to $NAD^+$ 44 resulting in NADH 42, and the cycle repeats.

In one exemplary embodiment, Photosystem II (PSII) 24 and Respiratory Complex I (CMI) (NADH:ubiquinone oxidoreductase) 46 are integrated into liposomes to form proteoliposomes 20, resulting in an artificial organelle capable of $NAD^+$ photoreduction (see FIG. 1A-C, with an enlarged view of FIG. 1B, region A provided in FIG. 1C). PSII 24 harvests light energy 22, splitting water 26 to oxygen 30 and protons 28 on the inside 38 of the proteoliposome; electrons are transferred from water 26 to Q 32 to form $QH_2$ 34 within the lipid bilayer 21 of the proteoliposome. The production of 4 protons in the interior of the proteoliposomes by PSII 24 generates a PMF driving reverse electron transfer of CMI 46. CMI 46 oxidizes the $QH_2$ 34 produced by PSII 24 transferring the electrons and a proton 48 to $NAD^+$ 44 resulting in NADH 42 and the cycle repeats.

In more detail, the proteoliposomes 20 comprise a membrane, which is a lipid bilayer 21 in the illustrated embodiment (FIG. 1B). Photons 22 harvested by PSII 24 result in water oxidation generating oxygen and protons as part of the process (illustrated in FIG. 1A as one molecule of $H_2O$ (26) yielding 2 $H^+$ (28)+½ $O_2$ (30) in the inside 38 of the proteoliposomes). The electrons from water are transferred to ubiquinone (Q) (32) within the lipid bilayer 21, producing ubiquinol ($QH_2$) (34) [34-35].

The accumulation of protons 36 on the inside 38 of the lipid bilayer 21 as compared with the outside 40 of the lipid bilayer generates a proton motive force (PMF) that diminishes the thermodynamic gap of the standard redox potentials between $NADH/NAD^+$ (42/44) and $QH_2/Q$ (34/32) to permit reverse electron transfer (RET) from $QH_2$ 34 to $NAD^+$ 44 by CMI 46 [36] as protons 36 from the inside 38 of the lipid bilayer 21 are pumped through CMI 46 to the outside 40 of the lipid bilayer 21 (illustrated as protons 48). By artificially coupling the associated metabolisms of these two enzymes, NADH 48 is produced from $NAD^+$ using light 22 and water 26 as substrates, with oxygen 30 as the only by-product. While $NAD^+/NADH$ are used as exemplary coenzymes in FIG. 1A-C, $NAD^+/NADH$, $NADP^+/NAPH$, or analogues thereof can be used in the systems described herein. Similarly, ubiquinone, ubiquinol, or analogues thereof can be used in the systems described herein.

In another embodiment, the artificial cell free organelle system comprises an enzymatic cofactor regeneration system, for example in the form of proteoliposomes 20, is incorporated into or supplied to a primary reaction system that requires the regeneration of spent NADH or NADPH (e.g., $NAH^+$, $NADP^+$, or analogues thereof). Examples of reaction systems that require regeneration of NADH, NADPH, or analogues thereof include diketoreductase, ketoreductase, oxidoreductase, aminoacid dehydrogenases, transaminases, and alpha-transaminase. See e.g., Bezborodov and Zagustina [37].

In another embodiment, supplying the engineered enzymatic cofactor regeneration system to the primary reaction system comprises adding an artificial organelle comprising a membrane, a photosynthetic reaction center (e.g., PSII) and an oxidoreductase enzyme (e.g., CMI) as described herein to the primary reaction system. In another embodiment, ubiquinol or an analogue thereof are incorporated into the membrane of the artificial organelle. In another embodiment, an ionophore, optionally a potassium ionophore, is also supplied to the primary reaction system. By applying light to the primary reaction system incorporating the artificial organelle, the artificial organelle is able to regenerate NADH, NADPH, or analogues thereof for use by the primary reaction system. Because the artificial organelle uses water as the source of electrons and produces only oxygen as a byproduct, use of the artificial organelle is unlikely to interfere with the primary reaction system.

One embodiment described herein is an artificial cell free organelle system comprising: a membrane having two sides comprising an inner surface in contact with an inner aqueous medium and an outer surface in contact with an outer aqueous medium; one or more photosynthetic proteins and one or more oxidoreductase proteins are vectorially embedded within and traversing the membrane; one or more first redox active cofactors; one or more second redox active cofactors; water, and a photon energy source; wherein: when one or more photons are directed on the one or more photosynthetic proteins, the photosynthetic proteins harvest the photon energy and catalyze the oxidation of at least one water molecule in the inner aqueous medium, generating 0.5 equivalents of oxygen gas and yielding up to two protons and two electrons per two photons that are transferred to an oxidized form of the first redox active cofactor, generating a reduced form of the first redox active cofactor; the accumulation of protons in the inner aqueous medium generates a proton concentration gradient between the inner aqueous medium and the outer aqueous medium; and the one or more oxidoreductase proteins pumps protons from the inner aqueous medium through the membrane to the outer aqueous medium to reduce the proton concentration gradient and simultaneously catalyzes the transfer of electrons from the reduced first redox cofactor to an oxidized form of the second redox active cofactor, generating a reduced form of the second redox active cofactor and an oxidized form of the first redox active cofactor. In one aspect, the membrane comprises a biomimetic bilayer, a biomimetic three-dimensional bilayer, a unilamellar liposome, a planar membrane, or a membraneous polymer construct. In another aspect, the membraneous polymer construct comprises a triblock co-polymer membrane comprising varying lengths of poly (dimethylsiloxane) (PDMS) as the hydrophobic membrane-forming block and poly(2-methyloxazoline) (PMOXA) as the hydrophilic membrane-forming block. In another aspect, the membrane comprises a closed unilamellar liposome comprising a phospholipid bilayer. In another aspect, the one or more photosynthetic proteins and one or more oxidoreductase proteins are vectorially embedded in the membrane using a detergent. In another aspect, the detergent comprises one or more of CHAPS (3-[(3-cholamidopropyl) dimethylammonio]-1-propanesulfonate), DDM (n-dodecyl-8-D-maltoside), OG (octyl-β-D-glucopyranoside), or Triton X-100. In another aspect, the one or more photosynthetic proteins comprises the photosystem II complex of proteins and/or bacteriorhodopsin. In another aspect, the photosystem II complex of proteins comprises the photosystem II complexes from *Cyanobacterium synechocystis, Synechocystis* sp., *Synechococcus elongates, Thermosynechococcus elongatus, Thermosynechococcus vulcans, Pisum sativum, Chlamydomonas reinhardtii, Spinacia oleracea*, or *Arabidopsis thaliana*; and the bacteriorhodopsin comprises the bacteriorhodopsin from *Halobacterium salinarum*. In another aspect, the photosystem II complex of proteins or bacteriorhodopsin are purified or recombinant. In another aspect, the one or more photosynthetic proteins comprise the photosystem II complex of proteins from *Synechocystis* sp. PCC6803. In another aspect, the one or more oxidoreductase enzymes comprises the Respiratory Complex I complex of proteins. In another aspect, the Respiratory Complex I complex of proteins comprises the Respiratory Complex I of *Eschericia coli, Thermus thermophilus, Vibrio cholerae, Yarrowia lipolytica, Ovis aries, Bos taurus, Mus musculus,* or *Homo sapiens*. In another aspect, the Respiratory Complex I complex of proteins are purified or recombinant. In another aspect, the one or more oxidoreductase enzymes comprises the Respiratory Complex I complex of proteins from *E. coli*. In another aspect, the one or more oxidoreductase enzymes comprises a Respiratory Complex I that has been engineered to preferentially reduce NADPH. In another aspect, the one or more oxidoreductase enzymes are vectorially incorporated into the membrane in an orientation opposite to the orientation of the oxidoreductase enzyme in vivo. In another aspect, the first redox active cofactor comprises ubiquinone or a ubiquinone analogue. In another aspect, the ubiquinone analogue has the structure:

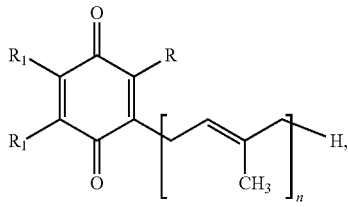

wherein R is methyl, hydroxyl, or hydrogen and $R_1$ is independently methoxy, methyl, hydroxyl or hydrogen, and n is an integer between 0 to 20, 6 to 12, or 7 to 10, including all integers within the specified ranges. In another aspect, the second redox active cofactor comprises $NAD^+$, $NADP^+$, an $NAD^+$ analogue, or an $NADP^+$ analogue. In another aspect, the $NAD^+$ or $NADP^+$ analogue has the structure:

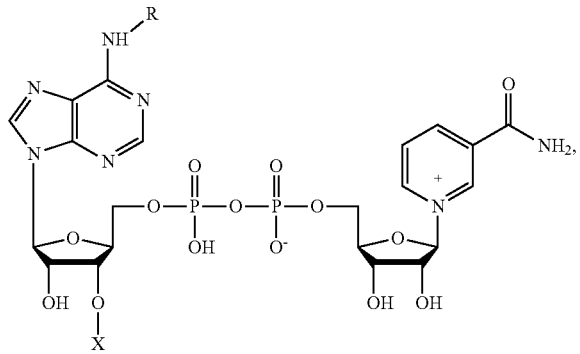

where R is a polyethylene glycol of 100 to 10,000 MW, a carbohydrate moiety or a polypeptide, and X is phosphate or hydrogen. In another aspect, the reduced form of the first redox active cofactor comprises ubiquinol, decylubiquinol, or a ubiquinol analogue. In another aspect, the ubiquinol analogue has the structure:

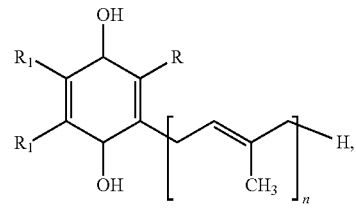

wherein R is methyl, hydroxyl, or hydrogen and $R_1$ is independently methoxy, methyl, hydroxyl or hydrogen, and n is an integer between 0 to 20, 6 to 12, or 7 to 10, including all integers within the specified ranges. In another aspect, the reduced form of the second redox active cofactor comprises NADH, NADPH, or an analogue thereof.

In another aspect, the NADH or NADPH analogue has the structure:

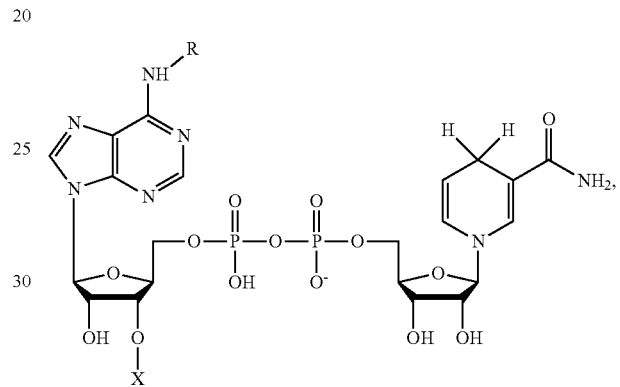

where R is a polyethylene glycol of 100 to 10,000 MW, a carbohydrate moiety, or a polypeptide, and X is phosphate or hydrogen. In another aspect, the system further comprises an ionophore comprising one or more of valinomycin, salinomycin, lasalocid, ionomycin, nonactin, beauvericin, or calcimycin. In another aspect, the system further comprises an ionophore comprising a potassium ionophore, and wherein the potassium ionophore comprises valinomycin or salinomycin.

Another embodiment described herein is a method or means for converting light energy and water into oxygen and reduced NADH, NADPH, or analogues thereof using artificial photosynthesis in an artificial cell free system, the method comprising: (a) providing an artificial cell free organelle system comprising: a membrane having two sides comprising an inner surface in contact with an inner aqueous medium and an outer surface in contact with an outer aqueous medium; one or more photosynthetic proteins comprising photosystem II or bacteriorhodopsin vectorially embedded within and traversing the membrane; one or more oxidoreductase proteins comprising Respiratory Complex I vectorially embedded within and traversing the membrane; ubiquinone or an analogue thereof; $NAD^+$, $NADP^+$ or an analogue thereof; water, and a photon energy source; (b) directing one or more photons to the one or more photosynthetic proteins; (c) the one or more photosynthetic proteins catalyzes the electron transfer from photon energy to ubiquinone or an analogue thereof, generating ubiquinol or an analogue thereof; and (d) the one or more oxidoreductase proteins catalyzes the electron transfer from ubiquinol or an analogue thereof to $NAD^+$, $NADP^+$, or analogues thereof, producing NADH, NADPH, or analogues thereof, and oxidizing ubiquinol or analogue thereof to ubiquinone or an analogue thereof. In one aspect, wherein: when one or more photons are directed on the one or more photosynthetic proteins, the photosynthetic proteins harvest the photon energy and catalyze the oxidation of at least one water molecule in the inner aqueous medium, generating 0.5 equivalents of oxygen gas and yielding up to two protons and two electrons per two photons that are transferred to ubiquinone or an analogue thereof, generating ubiquinol or an analogue thereof; the accumulation of protons in the inner aqueous medium generates a proton concentration gradient between the inner aqueous medium and the outer aqueous medium; and the oxidoreductase enzyme comprising Respiratory Complex I pumps protons from the inner aqueous medium through the membrane to the outer aqueous medium to reduce the proton concentration gradient and simultaneously catalyzes the transfer of electrons from ubiquinol or an analogue thereof to $NAD^+$, $NADP^+$, or analogues thereof, producing NADH, NADPH, or analogues thereof, and oxidizing ubiquinol or analogue thereof back to ubiquinone or a ubiquinone or an analogue thereof. In another aspect, the membrane comprises a biomimetic bilayer, a biomimetic three-dimensional bilayer, a unilamellar liposome, a planar membrane, or a membraneous polymer construct. In another aspect, the membraneous polymer construct comprises a triblock co-polymer membrane comprising varying lengths of poly(dimethylsiloxane) (PDMS) as the hydrophobic membrane-forming block and poly(2-methyloxazoline) (PMOXA) as the hydrophilic membrane-forming block. In another aspect, the membrane comprises a closed unilamellar liposome comprising a phospholipid bilayer. In another aspect, the one or more photosynthetic proteins and one or more oxidoreductase proteins are vectorially embedded in the membrane using a detergent. In another aspect, the detergent comprises one or more of CHAPS (3-[(3-cholamidopropyl)dimethylammonio]-1-propanesulfonate), DDM (n-dodecyl-β-D-maltoside), OG (octyl-β-D-glucopyranoside), or Triton X-100. In another aspect, the photosystem II complex of proteins comprises the photosystem II complexes from *Cyanobacterium synechocystis, Synechococcus elongates, Thermosynechococcus elongatus, Thermosynechococcus vulcans, Pisum sativum, Chlamydomonas reihhardtii, Spinacia oleracea,* or *Arabidopsis thaliana*; and the bacteriorhodopsin comprises the bacteriorhodopsin from *Halobacterium salinarum*. In another aspect, the photosystem II complex of proteins or bacteriorhodopsin are purified or recombinant. In another aspect, the one or more photosynthetic proteins comprise the photosystem II complex of proteins from *Cyanobacterium synechocystis*. In another aspect, the Respiratory Complex I complex of proteins comprises the Respiratory Complex I of *Eschericia coli, Thermus thermophilus, Vibrio cholerae, Yarrowia lipolytica, Ovis aries, Bos taurus, Mus musculus,* or *Homo sapiens*. In another aspect, the Respiratory Complex I complex of proteins are purified or recombinant. In another aspect, the one or more oxidoreductase enzymes comprises the Respiratory Complex I complex of proteins from *E. coli*. In another aspect, the one or more oxidoreductase enzymes comprises a Respiratory Complex I that has been engineered to preferentially reduce NADPH or an analogue thereof. In another aspect, the one or more oxidoreductase enzymes are vectorially incorporated into the membrane in an orientation opposite to the orientation of the oxidoreductase enzyme in vivo. In another aspect, the ubiquinone analogue has the structure:

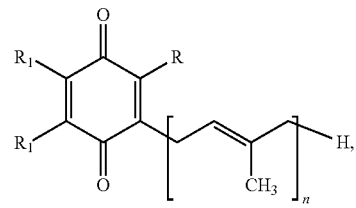

wherein R is methyl, hydroxyl, or hydrogen and $R_1$ is independently methoxy, methyl, hydroxyl or hydrogen, and n is an integer between 0 to 20, 6 to 12, or 7 to 10, including all integers within the specified ranges. In another aspect, the $NAD^+$ or $NADP^+$ analogue has the structure:

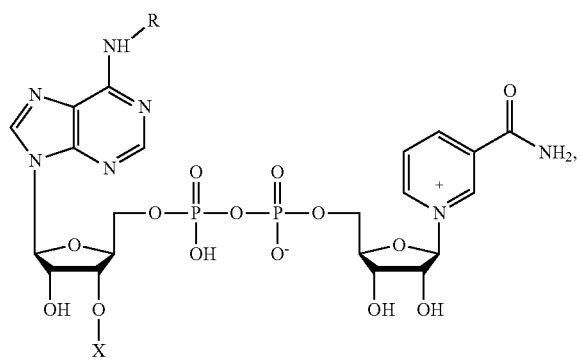

where R is a polyethylene glycol of 100 to 10,000 MW, a carbohydrate moiety or a polypeptide, and X is phosphate or hydrogen. In another aspect, the ubiquinol analogue has the structure:

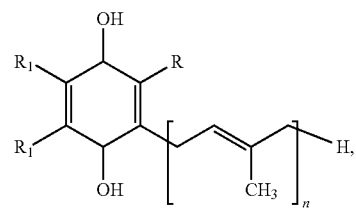

wherein R is methyl, hydroxyl, or hydrogen and $R_1$ is independently methoxy, methyl, hydroxyl or hydrogen, and n is an integer between 0 to 20, 6 to 12, or 7 to 10, including all integers within the specified ranges. In another aspect, the NADH or NADPH analogue has the structure:

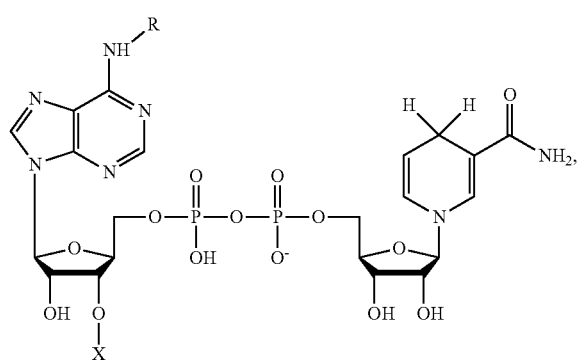

where R is a polyethylene glycol of 100 to 10,000 MW, a carbohydrate moiety, or a polypeptide, and X is phosphate or hydrogen. In another aspect, the method further comprises adding an ionophore comprising one or more of valinomycin, salinomycin, lasalocid, ionomycin, nonactin, beauvericin, or calcimycin. In another aspect, the method further comprises adding an ionophore comprising a potassium ionophore, and wherein the potassium ionophore comprises valinomycin or salinomycin.

Another embodiment described herein is NADH, NADPH, or analogues thereof produced by the methods described herein.

Another embodiment described herein is the use of an artificial cell free organelle system for converting light energy and water into oxygen and reduced NADH, NADPH, or analogues thereof using artificial photosynthesis in an artificial cell free system. In one aspect, the artificial cell free organelle system comprises: a membrane having two sides comprising an inner surface in contact with an inner aqueous medium and an outer surface in contact with an outer aqueous medium; one or more photosynthetic proteins comprising photosystem II or bacteriorhodopsin vectorially embedded within and traversing the membrane; one or more oxidoreductase proteins comprising Respiratory Complex I vectorially embedded within and traversing the membrane; ubiquinone or an analogue thereof; $NAD^+$, $NADP^+$ or an analogue thereof; water, and a photon energy source; wherein: the one or more photosynthetic proteins catalyzes the electron transfer from photon energy to ubiquinone or an analogue thereof, generating ubiquinol or an analogue thereof; and the one or more oxidoreductase proteins catalyzes the electron transfer from ubiquinol or an analogue thereof to $NAD^+$, $NADP^+$, or analogues thereof, producing NADH, NADPH, or analogues thereof, and oxidizing ubiquinol or analogue thereof to ubiquinone or an analogue thereof.

Further embodiments described herein include nucleic acid molecules comprising polynucleotides having nucleotide sequences about 50%, 55%, 60%, 65%, 70%, 75%, 80%, 85%, 90%, 91%, 92%, 93%, 94%, 95%, 96%, 97%, 98%, or 99% identical, and more preferably at least about 90-99% or 100% identical to (a) nucleotide sequences, or degenerate, homologous, or codon-optimized variants thereof, encoding polypeptides having the amino acid sequences in SEQ ID NO: 1-34; (b) nucleotide sequences, or degenerate, homologous, or codon-optimized variants thereof, encoding polypeptides having the amino acid sequences in SEQ ID NO: 1-34; and (c) nucleotide sequences capable of hybridizing to the complement of any of the nucleotide sequences in (a) or (b) above and capable of expressing functional polypeptides of amino acid sequences in SEQ ID NO: 1-34.

By a polynucleotide having a nucleotide sequence at least, for example, 90-99% "identical" to a reference nucleotide sequence encoding a protein as described herein is intended that the nucleotide sequence of the polynucleotide be identical to the reference sequence except that the polynucleotide sequence can include up to about 10 to 1 point mutations, additions, or deletions per each 100 nucleotides of the reference nucleotide sequence encoding the proteins described herein.

In other words, to obtain a polynucleotide having a nucleotide sequence about at least 90-99% identical to a reference nucleotide sequence, up to 10% of the nucleotides in the reference sequence can be deleted, added, or substituted, with another nucleotide, or a number of nucleotides up to 10% of the total nucleotides in the reference sequence can be inserted into the reference sequence. These mutations of the reference sequence can occur at the 5'- or 3'-terminal positions of the reference nucleotide sequence or anywhere between those terminal positions, interspersed either individually among nucleotides in the reference sequence or in one or more contiguous groups within the reference sequence. The same is applicable to polypeptide sequences about at least 90-99% identical to a reference polypeptide sequence.

As noted above, two or more polynucleotide sequences can be compared by determining their percent identity. Two or more amino acid sequences likewise can be compared by determining their percent identity. The percent identity of two sequences, whether nucleic acid or peptide sequences, is generally described as the number of exact matches between two aligned sequences divided by the length of the shorter sequence and multiplied by 100. An approximate alignment for nucleic acid sequences is provided by the local homology algorithm of Smith and Waterman, *Advances in Applied Mathematics* 2: 4 82-489 (1981). This algorithm can be extended to use with peptide sequences using the scoring matrix developed by Dayhoff, *Atlas of Protein Sequences and Structure*, M. O. Dayhoff ed., 5 suppl. 3: 353-358, National Biomedical Research Foundation, Washington, D.C., USA, and normalized by Gribskov, *Nucl. Acids Res.* 14(6): 6745-6763 (1986).

For example, due to the degeneracy of the genetic code, one having ordinary skill in the art will recognize that a large number of the nucleic acid molecules having a sequence at least 50%, 55%, 60%, 65%, 70%, 75%, 80%, 85%, 90%, 91%, 92%, 93%, 94%, 95%, 96%, 97%, 98%, 99%, or 100% identical to the nucleic acid sequences encoding the polypeptides shown in SEQ ID NO: 1-34, or degenerate, homologous, or codon-optimized variants thereof, will encode a protein described herein.

The polynucleotides described herein include those encoding mutations, variations, substitutions, additions, deletions, and particular examples of the polypeptides described herein. For example, guidance concerning how to make phenotypically silent amino acid substitutions is provided in Bowie et al., "Deciphering the Message in Protein Sequences: Tolerance to Amino Acid Substitutions," *Science* 247: 1306-1310 (1990), wherein the authors indicate that proteins are surprisingly tolerant of amino acid substitutions.

Thus, fragments, derivatives, or analogs of the polypeptides of SEQ ID NO: 1-34 can be (i) ones in which one or more of the amino acid residues (e.g., 1, 2, 3, 4, 5, 7, 8, 9, 10, 11, 12, 13, 14, 15, 16, 17, 18, 19, 20, 25, 30, 35, 40, 45, or 50 residues, or even more) are substituted with a conserved or non-conserved amino acid residue (preferably a conserved amino acid residue). Such substituted amino acid residues may or may not be one encoded by the genetic code, or (ii) ones in which one or more of the amino acid residues includes a substituent group (e.g., 1, 2, 3, 4, 5, 7, 8, 9, 10, 15, 20, 25, 30, 35, 40, 45, or 50 residues or even more), or (iii) ones in which the mature polypeptide is fused with another polypeptide or compound, such as a compound to increase the half-life of the polypeptide (for example, polyethylene glycol), or (iv) ones in which the additional amino acids are fused to the mature polypeptide, such as an IgG Fc fusion region peptide or leader or secretory sequence or a sequence which is employed for purification of the mature polypeptide or a proprotein sequence. Such fragments, derivatives, and analogs are deemed to be within the scope of those skilled in the art from the teachings herein.

In addition, fragments, derivatives, or analogs of the polypeptides of SEQ ID NO: 1-34 can be substituted with one or more conserved or non-conserved amino acid residue (preferably a conserved amino acid residue). In some cases these polypeptides, fragments, derivatives, or analogs thereof will have a polypeptide sequence at least 50%, 55%, 60%, 65%, 70%, 75%, 80%, 85%, 90%, 91%, 92%, 93%, 94%, 95%, 96%, 97%, 98%, 99% or 100% identical to the polypeptide sequence shown in SEQ ID NO: 1-34 and will comprise functional or non-functional proteins or enzymes. Similarly, additions or deletions to the polypeptides can be made either at the N- or C-termini or within non-conserved regions of the polypeptide (which are assumed to be non-critical because they have not been photogenically conserved).

As described herein, in many cases the amino acid substitutions, mutations, additions, or deletions are preferably of a minor nature, such as conservative amino acid substitutions that do not significantly affect the folding or activity of the protein or additions or deletions to the N- or C-termini. Of course, the number of amino acid substitutions, additions, or deletions a skilled artisan would make depends on many factors, including those described herein. Generally, the number of substitutions, additions, or deletions for any given polypeptide will not be more than about 100, 90, 80, 70, 60, 50, 40, 30, 25, 20, 19, 18, 17, 16, 15, 14, 13, 12, 11, 10, 9, 8, 7, 5, 6, 4, 3, 2, or 1.

Another embodiment described herein is a reaction mixture for reducing a spent enzymatic cofactor to yield a regenerated enzymatic cofactor upon exposure to light, the reaction mixture comprising: an engineered enzymatic cofactor regeneration system comprising: a membrane; a photosynthetic reaction center vectorially incorporated in the membrane; an oxidoreductase enzyme vectorially incorporated into the membrane; ubiquinol (2,3-dimethoxy-5-methyl-6-poly prenyl-1,4-benzoquinol) or an analogue thereof; and water ($H_2O$). In one aspect, the membrane comprises first and second hydrophilic layers surrounding an interior hydrophobic layer. In another aspect, the membrane comprises a lipid bilayer or a triblock co-polymer membrane. In another aspect, the membrane comprises a biomimetic membrane. In another aspect, the triblock co-polymer membrane comprises varying lengths of poly(dimethylsiloxane) (PDMS) as the hydrophobic membrane-forming block and poly(2-methyloxazoline) (PMOXA) as the hydrophilic membrane-forming block. In another aspect, the photosynthetic reaction center comprises photosystem II from any species. In another aspect, the photosynthetic reaction center comprises a thermostable photosystem II. In another aspect, the oxidoreductase enzyme comprises respiratory complex I. In another aspect, the respiratory complex I comprises respiratory complex I from any species. In another aspect, the respiratory complex I comprises a thermostable respiratory complex I. In another aspect, the oxidoreductase enzyme is vectorially incorporated into the membrane in an orientation opposite to the orientation of the oxidoreductase enzyme in vivo. In another aspect, the photosynthetic reaction center is vectorially incorporated in the membrane so that, upon exposure to light, the photosynthetic reaction center forms a proton gradient on a first side of the membrane. In another aspect, the oxidoreductase enzyme is vectorially incorporated in the membrane so that the oxidoreductase enzyme can carry out reverse electron transfer using the energy provided by the proton gradient by pumping protons from the first side of the membrane to a second side of the membrane. In another aspect, the membrane comprises a lipid bilayer, the engineered enzymatic cofactor regeneration system comprises proteoliposomes, and the photosynthetic reaction center and the oxidoreductase enzyme are vectorially incorporated into the membrane using CHAPS (3-[(3-cholamidopropyl)dimethylammonio]-1-propanesulfonate) as the detergent. In another aspect, the membrane comprises a triblock co-polymer membrane, and the engineered enzymatic cofactor regeneration system comprises vesicles formed from the membrane. In another aspect, the photosynthetic reaction center is vectorially incorporated into the proteoliposomes or the vesicles so that, upon exposure to light, the photosynthetic reaction center forms a proton gradient with an increased concentration of protons on the inside of the proteoliposomes or vesicles. In another aspect, the oxidoreductase enzyme is vectorially incorporated in the proteoliposomes or the vesicles so that it can carry out reverse electron transfer using the energy provided by the proton gradient by pumping protons from the inside of the proteoliposomes or the vesicles to the outside of the proteoliposomes or the vesicles. In another aspect, the ubiquinol or analogue thereof comprises a compound having the following structure:

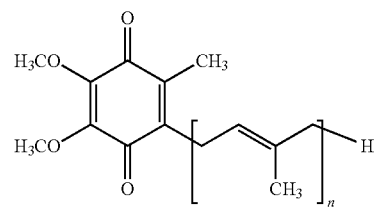

wherein n is an integer, wherein optionally n is between 0 and 20, or wherein optionally n is between 6 and 10, wherein optionally one or more of the methyl or methoxy substituents on the benzoquinone ring is absent or comprises a different substituent group, wherein optionally the ubiquinol or analogue thereof comprises ubiquinol or decylubiquinol. In another aspect, the spent enzymatic cofactor comprises $NAD^+$ or an analogue thereof and the regenerated enzymatic cofactor comprises NADH or an analogue thereof. In another aspect, the spent enzymatic cofactor comprises $NADP^+$ and the regenerated enzymatic cofactor comprises NADPH or an analogue thereof. In another aspect, the oxidoreductase enzyme comprises a respiratory complex 1 that has been engineered to preferentially reduce NADPH or an analogue thereof. In another aspect, the reaction mixture further comprises an ionophore, wherein the ionophore optionally comprises valinomycin, salinomycin, lasalocid, ionomycin, nonactin, beauvericin, or calcimycin. In another aspect, the ionophore comprises a potassium ionophore, and wherein the potassium ionophore optionally comprises valinomycin or salinomycin. In another aspect, the water ($H_2O$) supplies electrons to reduce the spent enzymatic cofactor upon exposure of the reaction mixture to light, and wherein essentially the only byproduct produced by the reaction mixture upon exposure to light is oxygen ($O_2$).

Another embodiment described herein is a method of regenerating a spent enzymatic cofactor using a reaction mixture as described herein, the method comprising: supplying the reaction mixture with the spent enzymatic cofactor; and supplying light to the reaction mixture. In one aspect, the reaction mixture further comprising: gathering energy from photons using the photosynthetic reaction center to cause the photosynthetic reaction center to transport protons across the membrane to form a proton gradient from a first side of the membrane to a second side of the membrane and reduce the ubiquinone or analogue thereof to ubiquinol or analogue thereof; and allowing the oxidoreductase enzyme to use energy provided by the proton gradient to carry out reverse electron transfer to reduce the spent enzymatic cofactor while oxidizing ubiquinol or analogue thereof to ubiquinone or analogue thereof.

Another embodiment described herein is a method of regenerating a spent enzymatic cofactor in a synthetic chemical process carried out in a primary reaction solution, the method comprising providing a reaction mixture as described herein in the primary reaction solution. In one aspect, the spent enzymatic cofactor comprises $NAD^+$, $NADP^+$ or analogues thereof.

Another embodiment described herein is an engineered enzymatic cofactor regeneration system comprising: a membrane; a photosynthetic reaction center vectorially incorporated in the membrane; and an oxidoreductase enzyme vectorially incorporated into the membrane.

Another embodiment described herein is an enzymatic cofactor regeneration system comprises one or more characteristics of the enzymatic cofactor regeneration system of the reaction mixture as described herein.

Another embodiment described herein is an artificial organelle for carrying out reduction of a spent enzymatic cofactor to produce a regenerated enzymatic cofactor, the artificial organelle comprising an engineered enzymatic cofactor regeneration system as described herein.

It will be apparent to one of ordinary skill in the relevant art that suitable modifications and adaptations to the compositions, formulations, methods, processes, apparata, assemblies, and applications described herein can be made without departing from the scope of any embodiments or aspects thereof. The compositions, apparata, assemblies, and methods provided are exemplary and are not intended to limit the scope of any of the disclosed embodiments. All the various embodiments, aspects, and options disclosed herein can be combined in any variations or iterations. The scope of the compositions, formulations, methods, apparata, assemblies, and processes described herein include all actual or potential combinations of embodiments, aspects, options, examples, and preferences described herein. The compositions, formulations, apparata, assemblies, or methods described herein may omit any component or step, substitute any component or step disclosed herein, or include any component or step disclosed elsewhere herein. The ratios of the mass of any component of any of the compositions or formulations disclosed herein to the mass of any other component in the formulation or to the total mass of the other components in the formulation are hereby disclosed as if they were expressly disclosed. Should the meaning of any terms in any of the patents or publications incorporated by reference conflict with the meaning of the terms used in this disclosure, the meanings of the terms or phrases in this disclosure are controlling. All patents and publications cited herein are incorporated by reference herein for the specific teachings thereof.

REFERENCES

A number of references are of interest with respect to the subject matter described herein.

1. Meyer et al., "The use of enzymes in organic synthesis and the life sciences: perspectives from the Swiss Industrial Biocatalysis Consortium (SIBC)," *Catal. Sci. Technol.* 3: 29-40 (2013).
2. Wu et al., "Methods for the regeneration of nicotinamide coenzymes," *Green Chem.* 15: 1773-1789 (2013).
3. Quinto et al., "Recent Trends in Biomimetic NADH Regeneration," *Top. Catal.* 57: 321-331 (2014).
4. Liu and Wang, "Cofactor regeneration for sustainable enzymatic biosynthesis," *Biotechnol. Adv.* 25: 369-384 (2007).
5. Uppada et al., "Cofactor regeneration—an important aspect of biocatalysis," *Curr. Sci. India* 106: 946-957 (2014).
6. Lee et al., "Coupling Photocatalysis and Redox Biocatalysis Toward Biocatalyzed Artificial Photosynthesis," *Chem. Eur. J.* 19: 4392-4406 (2013).
7. Steffen and Steuber, "Cation transport by the respiratory NADH: quinone oxidoreductase (complex I): facts and hypotheses," *Biochem. Soc. Trans.* 41: 1280-1287 (2013).
8. Verkhovskaya and Bloch, "Energy-converting respiratory Complex I: On the way to the molecular mechanism of the proton pump," *Int. J. Biochem. Cell. Biol.* 491-511 (2013).
9. Baradaran et al., "Crystal structure of the entire respiratory complex I." *Nature* 494(7438): 443-448 (2013).
10. Brandt, "Energy Converting NADH: Quinone Oxidoreductase (Complex I)," *Ann. Rev. Biochem.* 75 (1): 69-92 (2006).
11. Efremov et al., "The architecture of respiratory complex I," *Nature* 465(7297): 441-451 (2010).
12. Ohnishi et al., "A new hypothesis on the simultaneous direct and indirect proton pump mechanisms in NADH-quinone oxidoreductase (complex I)," *FEBS Lett.* 584 (19): 4131-4137 (2010).
13. Nore, "$\Delta pH$ driven energy-linked $NAD^+$ reduction in *Rhodospirillum rubrum* chromatophores," *Arch. Biochem. Biophys.* 274(1): 285-289 (1989).
14. Ohnishi et al., "Functional role of Coenzyme Q in the energy coupling of NADH-CoQ oxidoreductase (Complex I): Stabilization of the semiquinone state with the application of inside-positive membrane potential to proteoliposomes," *BioFactors* 32(1-4), 13-22 (2008).
15. Selivanov et al., "Reactive Oxygen Species Production by Forward and Reverse Electron Fluxes in the Mitochondrial Respiratory Chain," *PLoS Comput. Biol.* 7(3): e1001115 (2011).
16. Kotlyar and Borovok, "NADH oxidation and $NAD^+$ reduction catalysed by tightly coupled inside-out vesicles from *Paracoccus denitrificans*," *Eur. J. Biochem.* 269 (16): 4020-4024 (2002).
17. Wang et al., "Fast Isolation of Highly Active Photosystem II Core Complexes from Spinach," *J. Integr. Plant. Biol.* 52(9): 793-800 (2010).
18. Ramesh et al., "Isolation and characterization of an oxygen evolving photosystem 2 core complex from the thermophilic cyanobacterium *Mastigocladus laminosus*," *Photosynthetica*, 40(3): 355-361 (2002.
19. Kato et al., "Reisner, E., Protein film photoelectrochemistry of the water oxidation enzyme photosystem II," *Chem. Soc. Rev.* 43(18): 6485-6497 (2014).
20. Thornton et al., "The Low Molecular Weight Proteins of Photosystem II," in Wydrzynski and Satoh, Eds., Photosystem II The Light-Driven Water:Plastoquinone Oxidoreductase, Springer, 2006.
21. Barber, "Photosystem II: a multisubunit membrane protein that oxidises water," *Cur. Opin. Struct. Biol.* 12(4): 523-530 (2002).
22. Saito et al., "Mechanism of proton-coupled quinone reduction in Photosystem II," *Proc. Natl. Acad. Sci. USA* 110(3): 954-959 (2013).
23. Mavelli et al., "The binding of quinone to the photosynthetic reaction centers: kinetics and thermodynamics of reactions occurring at the Q(B)-site in zwitterionic and anionic liposomes," *Eur. Biophys. J. Biophy.* 43(6-7): 301-315 (2014).
24. Glockner et al., "Structural Changes of the Oxygen-evolving Complex in Photosystem II during the Catalytic Cycle," *J. Biol. Chem.* 288(31): 22607-22620 (2013).
25. Brudvig, "Water oxidation chemistry of photosystem II," *Philos. Trans. Royal Soc. B: Biol. Sci.* 363(1494): 1211-1219 (2008).
26. Liu and Wang, "Cofactor regeneration for sustainable enzymatic biosynthesis," *Biotechnol. Adv.* 25(4): 369-384 (2007).
27. Okuda et al., "Synthesis of Poly(Ethylene Glycol)-Bound NADP by Selective Modification at the 6-Amino Group of NADP," *Eur. J. Biochem.* 151, 33-38 (1985).
28. Shen et al., "Biomimetic membranes: A review," *J. Memb. Sci.*, 454:359-381 (2014).
29. Rigaud and Levy, "Reconstitution of membrane proteins into liposomes," *Liposomes, Pt B*, 372: 65-86 (2003).
30. Liang et al., "Inherently tunable electrostatic assembly of membrane proteins," *Nano Let.* 8(1): 333-339 (2008).
31. Hua et al., "Self-Directed Reconstitution of Proteorhodopsin with Amphiphilic Block Copolymers Induces the Formation of Hierarchically Ordered Proteopolymer Membrane Arrays," *J. Am. Chem. Soc.* 133(8): 2354-2357 (2011).
32. Liang et al., "The directed cooperative assembly of proteorhodopsin into 2D and 3D polarized arrays," *Proc. Natl. Acad. Sci. USA* 104(20): 8212-8217 (2007).
33. Morina et al. "Engineering the Respiratory Complex I to Energy-converting NADPH:Ubiquinone Oxidoreductase," *J. Biolog. Chem.* 268 (40): 34627-34634 (2011).
34. Muh et al., Light-induced quinone reduction in photosystem II," *Biochimica Biophysica Acta Bioenerg.* 1817: 44-65 (2012).
35. Barber, "Photosystem II: a multisubunit membrane protein that oxidises water," *Cur. Opin. Struc. Biol.* 12: 523-530 (2002).
36. Brandt, "Energy Converting NADH: Quinone Oxidoreductase (Complex I)," *Ann. Rev. Biochem.* 75: 69-92 (2006).
37. Bezborodov and Zagustina, "Enzymatic Biocatalysis in Chemical Synthesis of Pharmaceuticals," App. *Biochem. Microbiol.* 52(3): 237-249 (2016).
38. Pohl et al., "Lambda Red-mediated mutagenesis and efficient large scale affinity purification of the *Escherichia coli* NADH:ubiquinone oxidoreductase (complex I)," *Biochemistry* 46, 10694-10702 (2007).
39. Bricker et al., "Isolation of a highly active Photosystem II preparation from *Synechocystis* 6803 using a histidine-tagged mutant of CP47," *Biochimica Biophysica Acta* Bioenerg. 1409: 50-57 (1998).
40. Vavilin, in *Photosynthesis Research* Protocols, Second Edition, R. Carpentier, Ed., Humana Press Inc, Totowa, 684: 29-40 (2011).
41. Rigaud and Levy, "Reconstitution of membrane proteins into liposomes," *Liposomes*, Pt B 372: 65-86 (2003).
42. Pryde and Hirst, "Superoxide is produced by the reduced flavin in mitochondrial complex I: a single, unified mechanism that applies during both forward and reverse electron transfer," *J. Biolog. Chem.* 286:18056-18065 (2011).
43. Kotlyar and Vinogradov, "Slow Active Inactive Transition of the Mitochondrial Nadh-Ubiquinone Reductase," *Biochimica Biophysica Acta Bioenerg.* 1019:151-158 (1990).
44. Hsu et al., "The two binding sites for DCMU in Photosystem II," *Biochem. Biophys. Res. Comm.* 141: 682-688 (1986).
45. Trebst, "Inhibitors in the functional dissection of the photosynthetic electron transport system," *Photosynth. Res.* 92: 217-224 (2007).
46. Vinogradov et al., "Catalytic properties of mitochondrial NADH-ubiquinone reductase (Complex I)," *Biochemistry* 64:136-152 (1999).
46. Armstrong and Hirst, "Reversibility and efficiency in electrocatalytic energy conversion and lessons from enzymes," *Proc. Nat. Acad. Sci. USA* 108(34): 14049-14054 (2011).
47. Seigneuret and Rigaud, "Analysis of Passive and Light-Driven Ion Movements in Large Bacteriorhodopsin Liposomes Reconstituted by Reverse-Phase Evaporation. 2. Influence of Passive Permeability and Back-Pressure Effects Upon Light-Induced Proton Uptake," *Biochemistry* 25(21): 6723-6730 (1986).
48. Hazard and Montemagno, "Improved purification for thermophilic $F_1F_0$ ATP synthase using n-dodecyl beta-D-maltoside," *Arch, Biochem Biophys.* 407(1): 117-124 (2002).
49. Vinogradov and Grivennikova, "Oxidation of NADH and ROS production by respiratory complex I," *Biochimica Biophysica Acta Bioenerg.* 1857(7): 863-871 (2016).
50. Zu et al., "Reversible, Electrochemical Interconversion of NADH and $NAD^+$ by the Catalytic (Iλ) Subcomplex of Mitochondrial NADH:Ubiquinone Oxidoreductase (Complex I)," *J. Am. Chem. Soc.* 125(20): 6020-6021 (2003).
51. Friedrich et al., "2 Binding-Sites for Naturally-Occurring Inhibitors in Mitochondrial and Bacterial Nadh-Ubiquinone Oxidoreductase (Complex-I)," *Biochem Soc. Transact.* 22(1): 226-230 (1994).
52. Ohnishi et al., "Possible roles of two quinone molecules in direct and indirect proton pumps of bovine heart NADH-quinone oxidoreductase (complex I)," *Biochimica Biophysica Acta Bioenerg.* 1797(12): 1891-1893 (2010).
53. Belevich et al., "Activation of respiratory Complex I from *Escherichia coli* studied by fluorescent probes," *Heliyon* 3(1): e00224 (2017).
54. Casadio, "Measurements of Transmembrane pH Differences of Low Extents in Bacterial Chromatophores—a Study with the Fluorescent-Probe 9-Amino, 6-Chloro, 2-Methoxyacridine," *Eur. Biophys. J.* 19(4): 189-201 (1991).
55. D'Alessandro et al., "Quantitative evaluation of the intrinsic uncoupling modulated by ADP and Pi in the reconstituted ATP synthase of *Escherichia coli*," *Biochimica Biophysica Acta Bioenerg.* 1807(1): 130-143 (2011).
56. Loll et al., "*Towards complete cofactor arrangement in the* 3.0 Å resolution structure of photosystem II," *Nature* 438: 1040-1044 (2005).
57. Umena et al., "Crystal structure of oxygen-evolving photosystem II at a resolution of 1.9 Å," *Nature* 473: 55-60 (2011).
58. Su et al., "Structure and assembly mechanism of plant $C_2S_2M_2$-type PSII-LHCII supercomplex," *Science* 357 (6353): 815-820 (2017).
59. Sheng et al., "Structural insight into light harvesting for photosystem II in green algae," *Nature Plants* 5: 1320-1330 (2019).

60. Wei et al., "Structure of spinach photosystem II-LHCII supercomplex at 3.2 Å resolution," *Nature* 534: 69-74 (2016).
61. van Bezouwen et al., "Subunit and chlorophyll organization of the plant photosystem II supercomplex," *Nature Plants* 3: 17080 (2017).
62. Sazanov and Hinchliffe, "Structure of the hydrophilic domain of respiratory complex I from *Thermus thermophilus*," *Science* 311(5766): 1430-1466 (2006).
63. Steuber et al., "Structure of the *V. cholerae* Na+-pumping NADH:quinone oxidoreductase," *Nature* 516: 62-67 (2014).
64. Parey et al., "High-resolution cryo-EM structures of respiratory complex I: Mechanism, assembly, and disease," *Science Advances* 5(12): eaax9484 (2019).
65. Kampjut and Sazanov, "The coupling mechanism of mammalian respiratory complex I," *Science* 370 (6516): eabc4209 (2020).
66. Zhu et al., "Structure of mammalian respiratory complex I," *Nature* 536: 354-358 (2016).
67. Bridges et al., "Structure of inhibitor-bound mammalian complex I," *Nature Comm.* 11(5261) (2020).
68. Guo et al., "Architecture of Human Mitochondrial Respiratory Megacomplex $I_2III_2IV_2$," *Cell* 170(6): 1247-1257 (2017).

EXAMPLES

Example 1

Materials and Methods
Purification of NADH:Ubiquinone Oxidoreductase (Complex I)

Figure 2A:
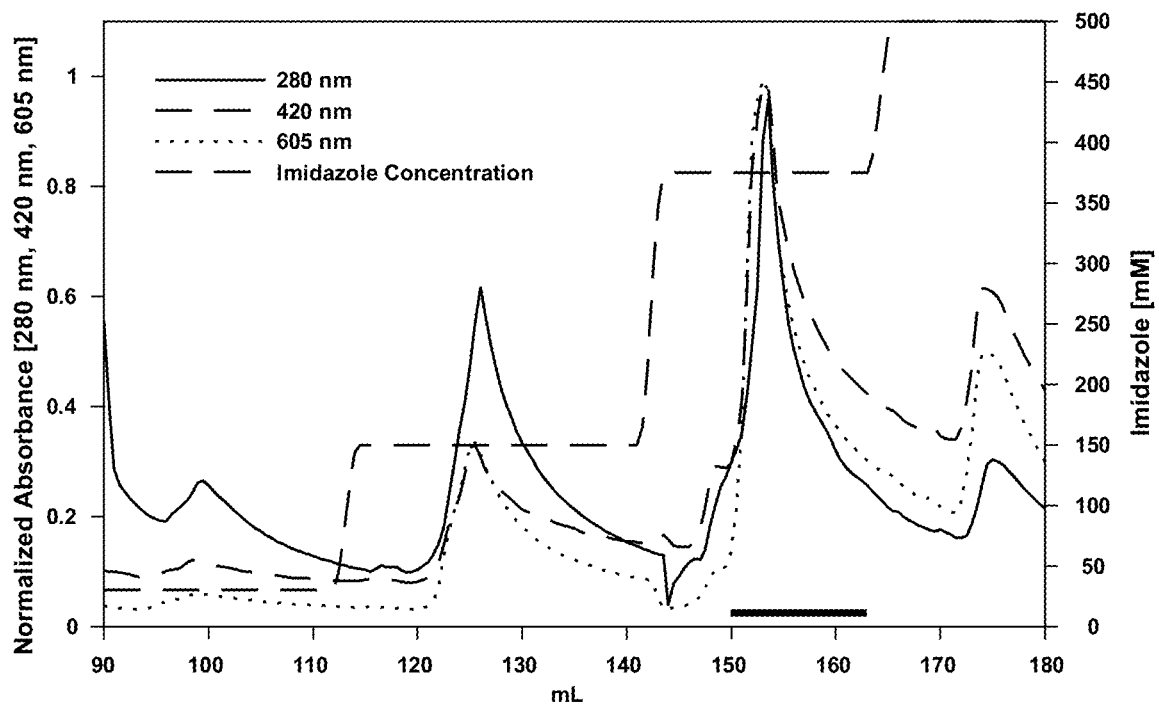
FIG. 2A-B show the purification of NADH:ubiquinone oxidoreductase (Complex 1) from *E. coli*.
Figure 2B:
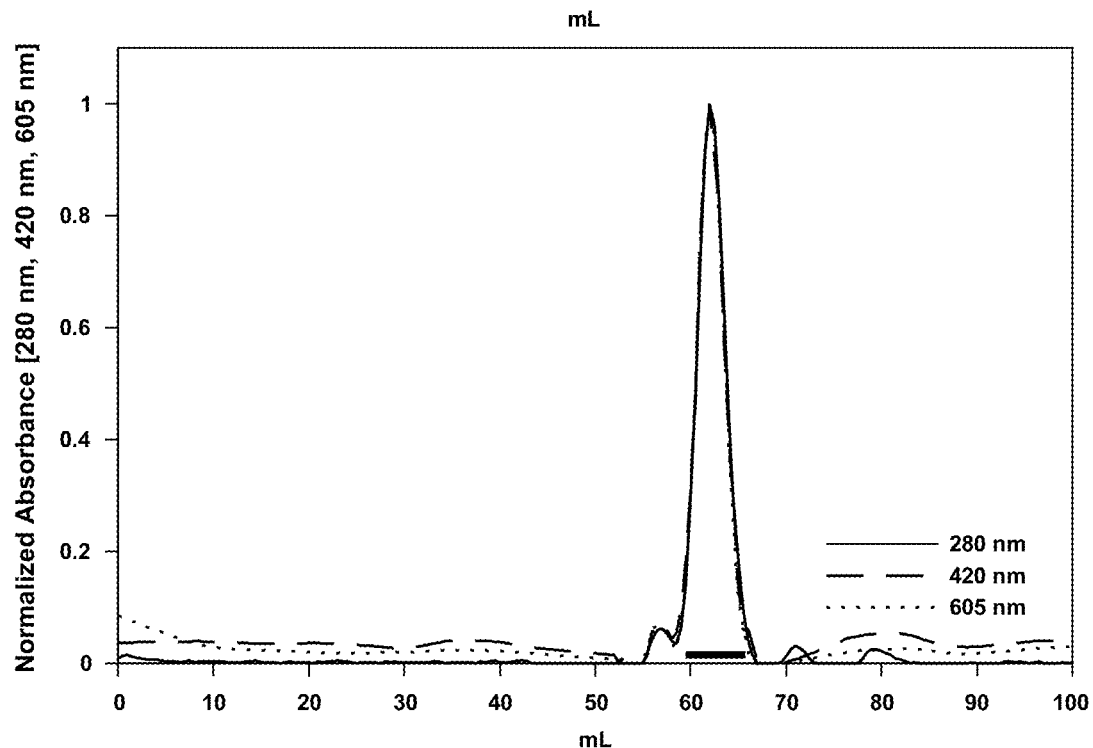
Figure 3:
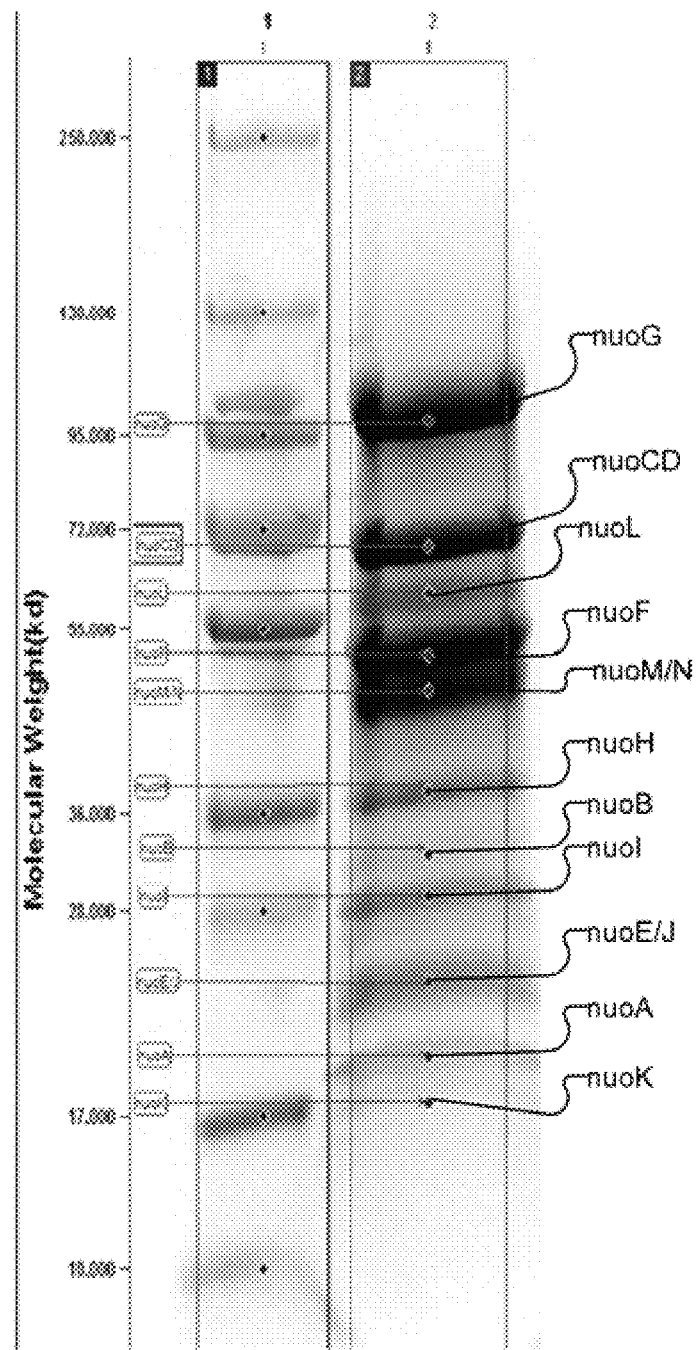
FIG. 3 shows a sodium dodecyl sulfate-polyacrylamide gel electrophoresis SDS-PAGE of purified Complex I from *E. coli*. Lane 1, molecular weight markers; Lane 2, 100 µg of purified Complex I. All 13 subunits of *E. coli* Complex I are present with no contaminating bands. Bands are labeled by the apparent molecular weight of the subunits.

Respiratory Complex I (CMI) was purified from *E. coli* overexpression strain ANN0221 using modifications to the methods described by Pohl et al. [38]. All chromatographic steps were performed using a GE ÄKTApure 25 or ÄKTAavant 125. The anion exchange step was omitted, and affinity chromatography was completed using a Tricorn 10 mm×100 mm (GE Healthcare Life Sciences, Inc.) column packed with High-Performance $Ni^{2+}$ resin (GE Healthcare Life Sciences, Inc.). The sample was adjusted to a final imidazole concentration of 50 mM and 200 mM NaCl, followed by sample loading at 153 cm $h^{-1}$; the column was washed with 150 mM imidazole and CMI was eluted with 375 mM imidazole step gradient at 76.5 cm $h^{-1}$ in up-flow operation (FIG. 2A). The fractions containing CMI (indicated by black bar) were concentrated using a 100 kD MWCO Amicon® Ultra centrifugal filter (EMD Millipore, Inc.) to 2-3 mL. The concentrated protein sample was polished and desalted into 50 mM MES, pH 6.0, 50 mM NaCl 0.1% (w/v) DDM by applying to a HiLoad 16/600 Superdex 200 (GE Healthcare Life Sciences, Inc.) size exclusion column (FIG. 2B). Fractions containing CMI (indicated by black bar) were concentrated to 4-5 mg $mL^{-1}$ using Amicon® Ultra centrifugal filters, aliquoted, snap frozen, and stored at −80° C. FIG. 3 shows SDS-PAGE of the purified CMI confirming that all 13 subunits of Complex I are present with no contaminating bands.

Purification of Photosystem II

Figure 4A:
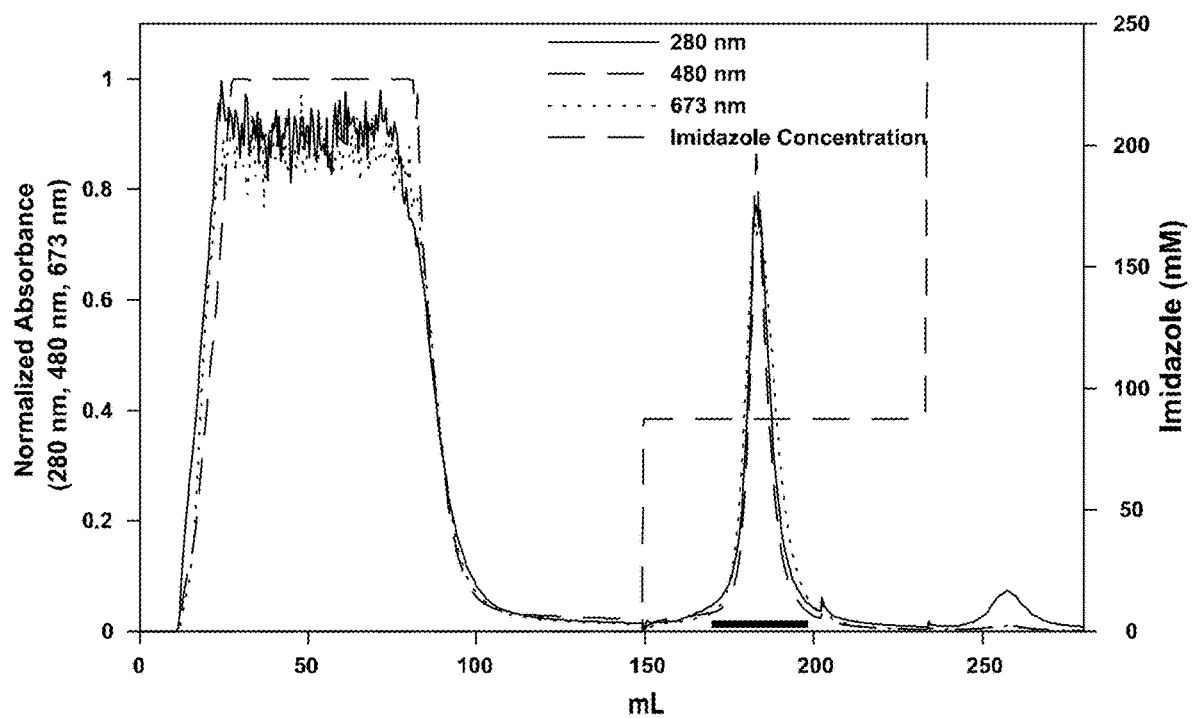
FIG. 4A-B show the purified Photosystem II (PSII) from *Cyanobacterium synechocystis* 6803 (*Synechocystis* sp. PCC 6803) used in the examples.
Figure 4B:
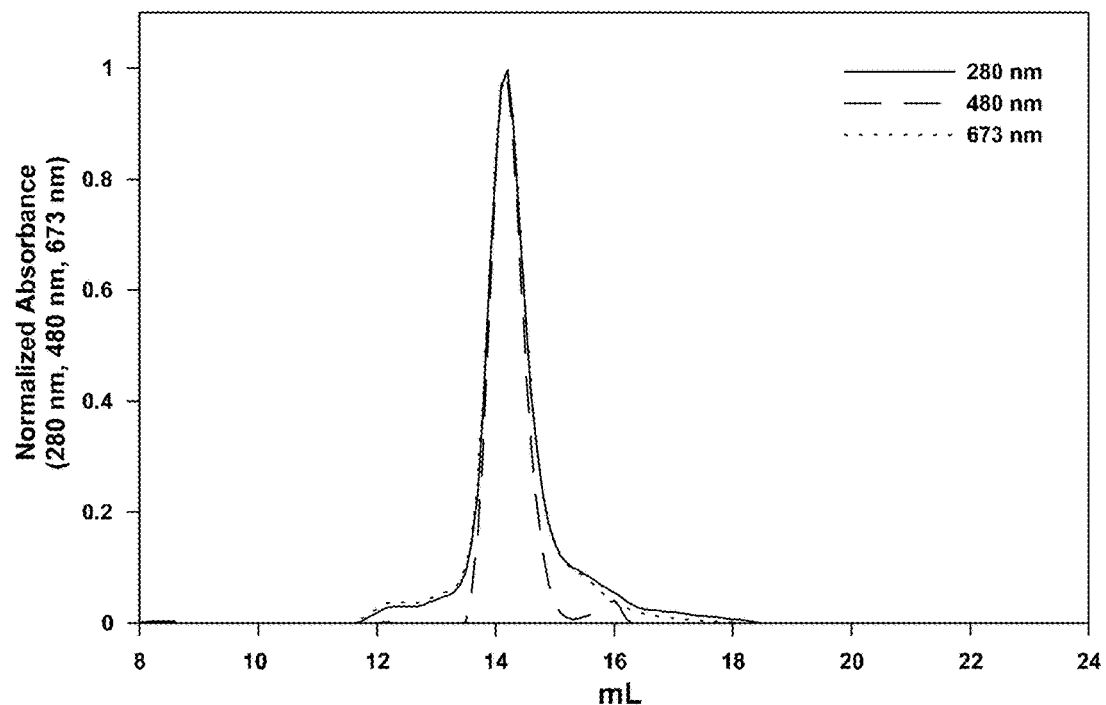

Photosystem II (PSII) with a histidine tag located on the CD47 subunit was isolated from *Cyanobacterium synechocystis* 6803 (*Synechocystis* sp. PCC6803) [39]. Isolated thylakoid membranes were resuspended to 1 mg ChlA $mL^{-1}$ in 50 mM MES, pH 6.0 10 mM $MgCl_2$, 5 mM $CaCl_2$, 25% (v/v) glycerol. The membranes were solubilized by dropwise addition of 20% (w/v) DDM to a final concentration of 0.8% (w/v) and incubated at 4° C. for 20 min. Non-solubilized material was removed by centrifugation using a multiple speed increase 100 rcf×1 min, 2,900 rcf×1 min, 4,900 rcf×1 min, 8,000 rcf×1 min, 15,100 rcf×1 min and 22,100 rcf×10 minutes using a Beckman Coulter Type 45-Ti Rotor. All chromatography steps were performed using an ÄKTAPure 25. The sample was loaded onto an XK 20/10 column (GE Healthcare Life Sciences, Inc.) packed with High-Performance $Ni^{2+}$ resin (GE Healthcare Life Sciences, Inc.) pre-equilibrated with binding buffer at a linear flow rate of 38 cm $h^{-1}$. Column washing was continued with binding buffer at 38 cm $h^{-1}$ until the absorbance at 280 nm fell below 90 mAU. PSII was eluted using 87.5 mM L-Histidine in up-flow operation at 22.6 38 cm $h^{-1}$ and 2 mL fractions were collected (FIG. 4A). Fractions containing PSII (shown by black bar) were pooled and concentrated using a 100 kD MWCO Amicon® Ultra centrifugal filter (EMD Millipore, Inc.). Removal of L-histidine was completed by diluting the concentrated sample 10-fold with binding buffer and concentrated; this was repeated 3 times. Samples were concentrated to 2-3 mg $mL^{-1}$ using Amicon® Ultra centrifugal filters, aliquoted, snap frozen and stored at −80° C. Chlorophyll A concentration was determined using 80% (v/v) acetone extraction [40]. Purity of the obtained PSII was verified by size exclusion chromatography on a Superose 6 Increase 10/300 column (FIG. 4B); black bars indicate fractions used in subsequent steps).

Unilamellar Liposome Preparation

Total *E. coli* lipid extract (Avanti Lipids Polar, Inc.) were dissolved in chloroform ($CHCl_3$) at 20 mg $mL^{-1}$ in a glass scintillation vial. A thin film was formed by removal of the $CHCl_3$ under vacuum at 0 mm Hg using a rotary evaporator. The thin film was rehydrated to 15.34 mg $mL^{-1}$ using 5 mM MES, pH 6.5 50 mM KCl, 5 mM $MgCl_2$ 2 mM $CaCl_2$ buffer and placed in a sonication bath for 5 min followed by two freeze-thaw cycles before being extruded through a 0.4 µm polycarbonate membrane 21 times. The mean diameter was measured by dynamic light scattering; a typical preparation was 180 nm.

Enzyme Reconstitution

The unilamellar liposome suspension was diluted to a final lipid concentration of 4 mg $mL^{-1}$ and CHAPS concentration of 5 mM by the combination of appropriate amounts of the corresponding buffer, 200 mM CHAPS in the corresponding buffer and concentrated protein. The liposomes-detergent mixture was incubated for 10 min before the addition of protein. The appropriate amount of CMI (4.7 mg $mL^{-1}$, 50 mM MES, pH 6.0, 50 mM NaCl 1.95 mM n-dodecyl-β-D-maltoside (DDM)) and PSII (2.6 mg $mL^{-1}$, 50 mM MES, pH 6.0 10 mM $MgCl_2$, 5 mM $CaCl_2$, 25% (v/v) glycerol, 0.78 mM DDM) were added to the CHAPS-solubilized preformed liposomes and incubated for 30 min at 4° C. will gentle mixing in the dark. For control experiments which did not contain an enzyme, the difference in volume was adjusted with buffer.

After the incubation period, the detergent was removed from the lipid-detergent-protein mixture by 3 successive additions of Bio-Beads SM-2 (80 mg $mL^{-1}$) every 60 min followed by a final addition of 240 mg $mL^{-1}$ and 60 min incubation.

Complex I Activity Measurements

Complex I NADH:DQ oxidoreductase and proton pumping activity were measured simultaneously using a Flexstation 3 (Molecular Devices, Inc.). NADH:DQ oxidoreductase activity was monitored through NADH oxidation by fluorescence spectroscopy ($\lambda_{exictation}$=340 nm, $\lambda_{emission}$=455 nm), while proton gradient generation was determined by quenching of ACMA ($\lambda_{exictation}$=410 nm, $\lambda_{emission}$=480 nm). The assay was conducted at 28° C. in the corresponding buffer, 25 µL of proteoliposomes were added to 175 µL assay mixture containing 100 µM DQ, 200 µM NADH, 0.2 µM valinomycin, 2.5 µM ACMA and for decoupling and inhibition assays 5 µM CCCP (carbonyl cyanide 3-chlorophenylhydrazone) and 50 µM Piericidin A, respectively. The sample was incubated for 5 min prior to reaction initiation by addition of NADH. When conducting inhibition assays proteoliposomes were incubated for 5 min with Piericidin A before the addition of DQ.

For these experiments, decylubiquinone (DQ) was selected as the analogue of ubiquinone because it could be readily incorporated into the proteoliposomes and could be used by both PSII and CMI. One skilled in the art could use alternative analogues of ubiquinone or ubiquinol for use in any particular situation.

Photosystem II Activity Measurements

Oxygen evolution assays were performed using 50 mM MES, pH 6.5, 10 mM NaCl, 5 mM $MgCl_2$, 20 mM $CaCl_2$) using a Clarke-type electrode (Hansatech Instruments, Ltd.). 2 mM ferricyanide and either 300 µM 2,5-dicholor-1,4-benzoquinone (DCBQ) or 50 µM DQ was added as electron acceptor with $5 \times 10^{-10}$ µg of ChlA of the sample to a final volume of 1.5 mL. The reaction took place at 28° C. and was initiated by red light at 2800 µmol $s^{-1}$ $m^{-2}$.

ATAD+ Photoreduction Assay

Photoreduction by CMI:PSII proteoliposomes were routinely performed at 28° C. in 5 mM MES, pH 6.5, 50 mM KCl, 5 mM $MgCl_2$ 2 mM $CaCl_2$, 25 µL of proteoliposomes were added to 175 µL assay mixture containing 50 µM DQ, 0.2 µM valinomycin, 2.5 µM ACMA; and for decoupling and inhibition assays: 5 µM CCCP and 100 µM DCMU, respectively. The potassium ionophore, valinomycin, was added to collapse the electrical component of the PMF and generate a higher ΔpH. Without being bound by any theory, the reverse electron transfer activity of CMI is believed to be more dependent on the proton component of the pH gradient than the electrical component of the pH gradient. Saturating white light >2200 µmol photons $m^{-2}$ $s^{-1}$ was provided by a 100 W Mercury lamp. The light was passed through a 2 L water bath. The reaction was monitored using Flexstation 3 (Molecular Devices, Inc.), NADH concentration was monitored by fluorescence spectroscopy ($\lambda_{exictation}$=340 nm, $\lambda_{emission}$=455 nm), while the proton gradient generation was determined by the change in ACMA signal ($\lambda_{exictation}$=410 nm, $\lambda_{emission}$=480 nm).

Protein Concentration

Protein concentration was routinely determined using Millipore Direct Detect® infrared spectrometer (EMD Millipore, Inc.).

Example 2

Production of Exemplary Proteoliposome Constructs

The isolated enzymes were reconstituted into liposomes following the methods delineated by Riguard [41]. When reconstituting membrane proteins, preservation of structure and activity, and also vectoral insertion of the membrane protein into the membrane in the correct orientation are important. Control of the concentrations of buffer and salt, and control of pH, can be used to preferentially drive reconstitution of the membrane protein with the desired orientation in the membrane.

Successful co-reconstitution of both enzymes into a single liposome initially required detergent screening experiments to reconstitute each enzyme independently (results shown in Tables 4 and 5). The optimal detergent and concentration were selected based upon their impact both on the PMF generation and enzymatic activity for each reconstituted enzyme/detergent pair.

The zwitterionic surfactant CHAPS (3-[(3-cholamidopropyl)dimethylammonio]-1-propanesulfonate) was found most suitable for co-reconstitution under the conditions tested. Other tested detergents were DDM (n-dodecyl-β-D-maltopyranoside), Triton X-100™ (polyethylene glycol p-(1,1,3,3-tetramethylbutyl)-phenyl ether), and OG (n-octyl-β-D-glucoside).

TABLE 4

Detergent Screening for CMI.

| Detergent | Detergent Concentration (mM) | ACMA Fluorescence decrease | NADH:DQ oxidoreductase activity (umol min$^{-1}$ mg CMI$^{-1}$) |
|---|---|---|---|
| DDM | 3.8 | 1.46% | 13.43 |
| DDM | 7 | 0.32% | 0.76 |
| Triton X-100 ™ | 1.8 | -2.75% | -0.00 |
| Triton X-100 ™ | 7 | -4.90% | 9.05 |
| OG | 18 | 0.71% | 5.24 |
| OG | 26 | -0.16% | 8.95 |
| CHAPS | 3.0 | 0.58% | N/A[1] |
| CHAPS | 7 | 74.54% | N/A[1] |

[1]Rates were too fast to measure, and were confirmed by the inhibition with 50 µM Piericidin A.
Rates for inhibited samples CHAPS 3.0 and 7.0 mM proteoliposomes were -1.05 and -0.48 (umol min$^{-1}$ mg CMI$^{-1}$), respectively.

TABLE 5

Detergent Screening for PSII.

| Detergent | Detergent Concentration (mM) | $O_2$ Evolution (umol $O_2$ hr$^{-1}$ ug ChlA) (mean ± S.D.) |
|---|---|---|
| CHAPS | 3.0 | 178.08 ± 9.91 |
| CHAPS | 7 | 509.24 ± 256.84 |
| DDM | 3.8 | 565.87 ± 25.19 |
| DDM | 6.8 | 396.55 ± 69.76 |
| OG | 18 | 306.95 ± 44.24 |
| OG | 26 | 481.01 ± 192.16 |
| TRITON X-100 ™ | 1.8 | 530.72 ± 2.53 |
| TRITON X-100 ™ | 7 | 218.69 ± 67.01 |

Figure 5A:
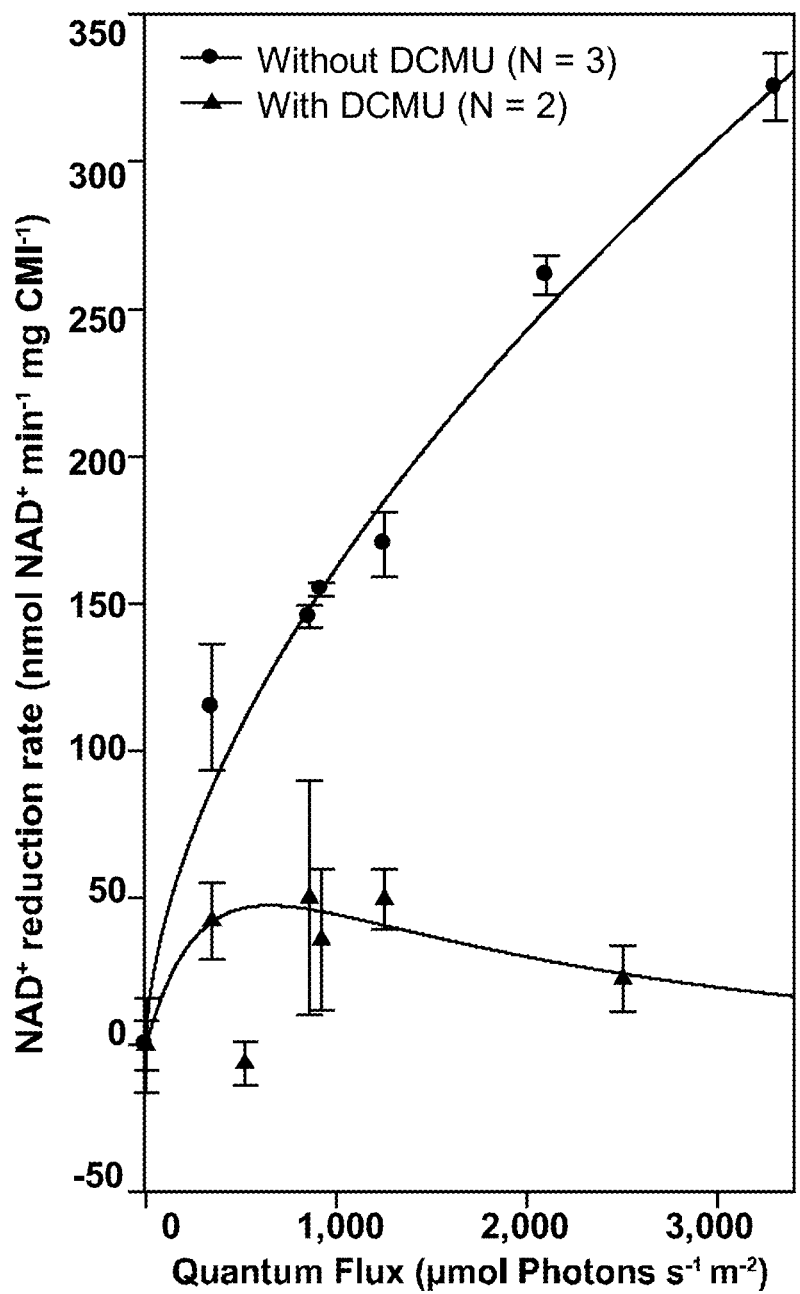
FIG. 5A-C show activity versus quantum flux and Coupling efficiency of PSII and Complex I.

To confirm that CMI was reconstituted into the liposomes both NADH:decylubiquinone (DQ) oxidoreductase activity and proton translocation were measured by monitoring NADH oxidation with the corresponding quenching of the pH sensitive fluorophore 9-amino-6-chloro-2-methoxyacridine (ACMA), respectively. The results are shown in FIG. 5. In FIG. 5A, after 5 min of incubation at 28° C., 200 µM NADH was added, and the depletion of NADH (dashed lines) and ACMA signal (solid lines) was monitored. The ACMA signal begins to increase at ~5 min due to the complete oxidation of NADH by CMI.

Figure 5B:
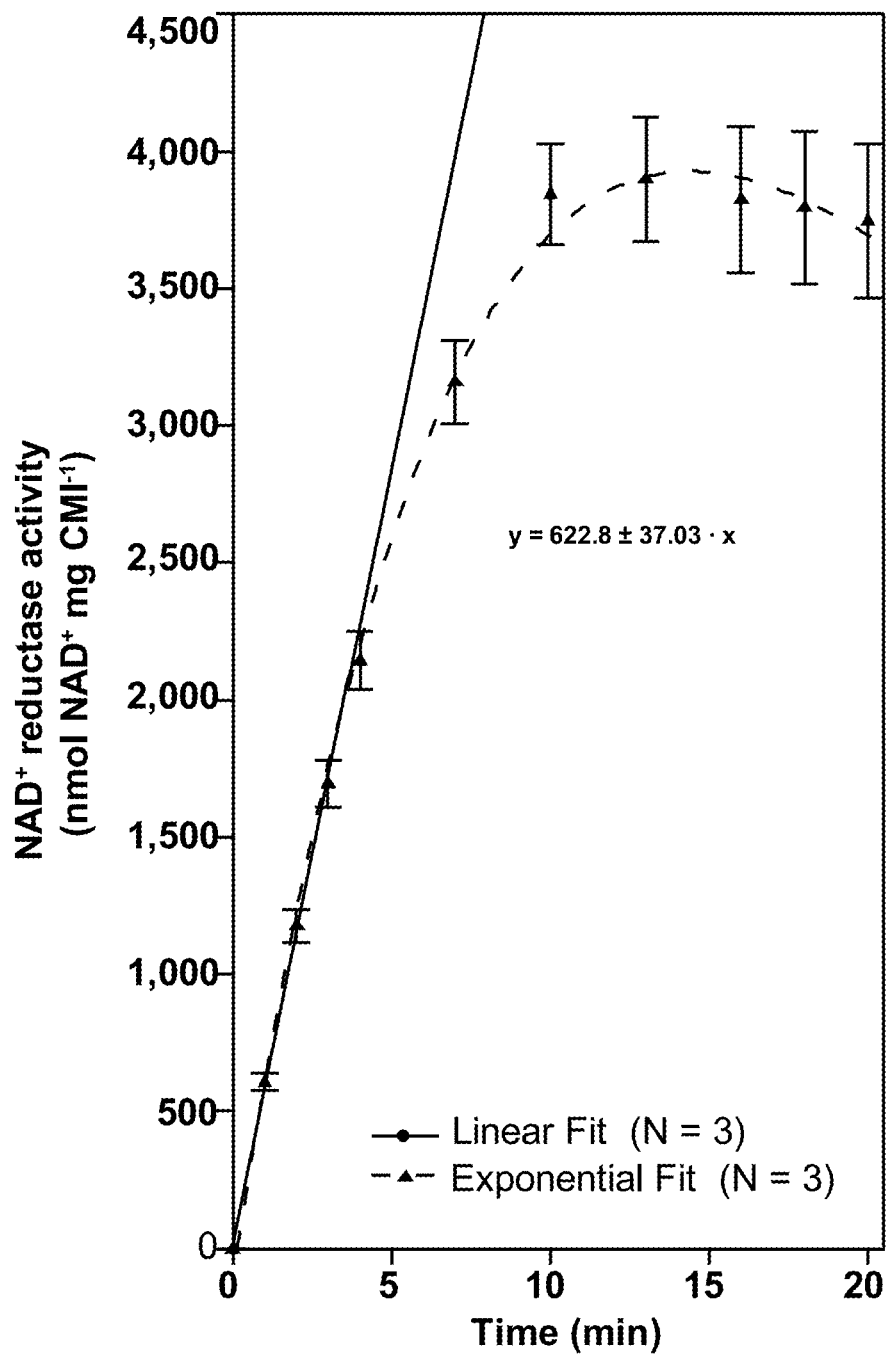
Figure 5C:
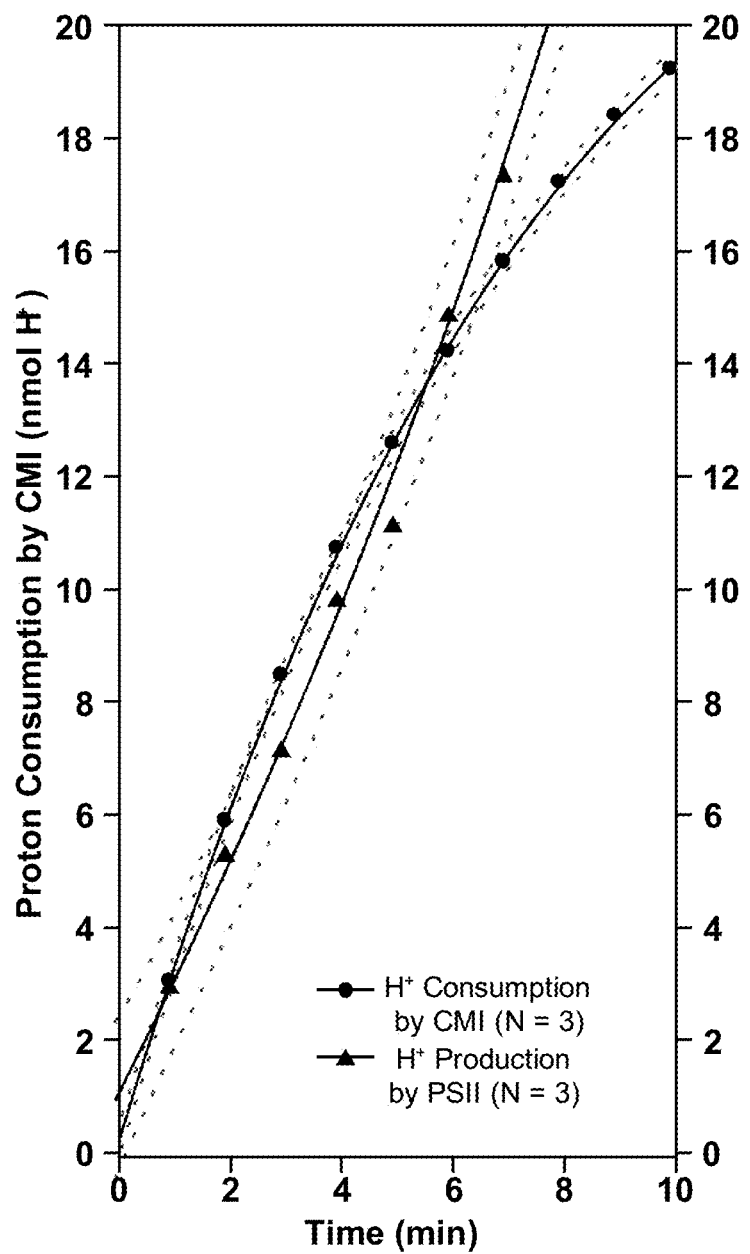
Figure 5D:
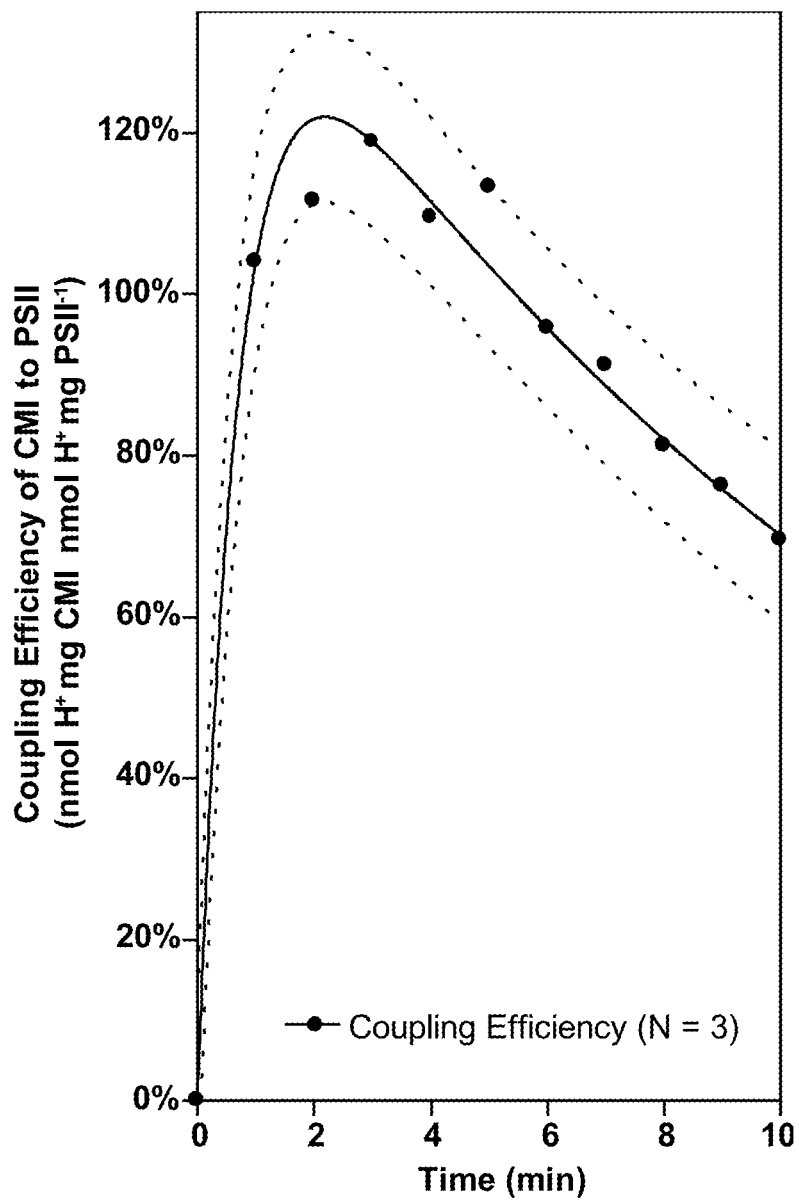
FIG. 5D shows the coupling efficiency based on the stoichiometric H+ and consumption and production by CMI and PSII, respectively at 3,000 µmol photons $s^{-1}$ $m^{-2}$. The dotted lines in FIG. 5C and FIG. 5D are the 95% confidence bounds of the exponential best-fit equation. The error bars represent the SEM of N biological replicates with three technical replicates.

In FIG. 5B, the effect on PMF formation by CMI proteoliposomes of NADH alone (dot-dashed line, labelled ACMA), NADH plus Piericidin A (dashed line) and NADH plus CCCP (solid line) are shown. Samples were incubated for 5 min with addition reagents (CCCP or Piericidin A as indicated) before the addition of 200 µM NADH at the indicated point. At 8 min 5 µM CCCP was added to all samples and the proton gradient was abolished. The data in FIG. 5 represent the mean of three independent measurements of a single preparation.

CMI proteoliposome preparations result in an ~80% decrease in ACMA fluorescence with a NADH:DQ oxidoreductase specific activity of 3,200 nmol NADH min$^{-1}$ mg CMI$^{-1}$ (FIG. 5A, solid line labelled ACMA). The decrease in ACMA signal was confirmed to be the result of CMI activity from incubation with the protonophore carbonyl cyanide 3-chlorophenylhydrazone (CCCP) (which quenches the proton gradient), because minimal change in ACMA fluorescence was observed (FIG. 5A), solid line labelled ACMA 5 μM CCCP). Additionally, the NADH:DQ oxidoreductase specific activity of CMI proteoliposomes was inhibited >95% when incubated with 50 μM Piericidin A (FIG. 5A), compare dashed line labelled NADH 50 μM Piericidin A with dashed line labeled NADH; a potent CMI inhibitor [38].

Figure 6:
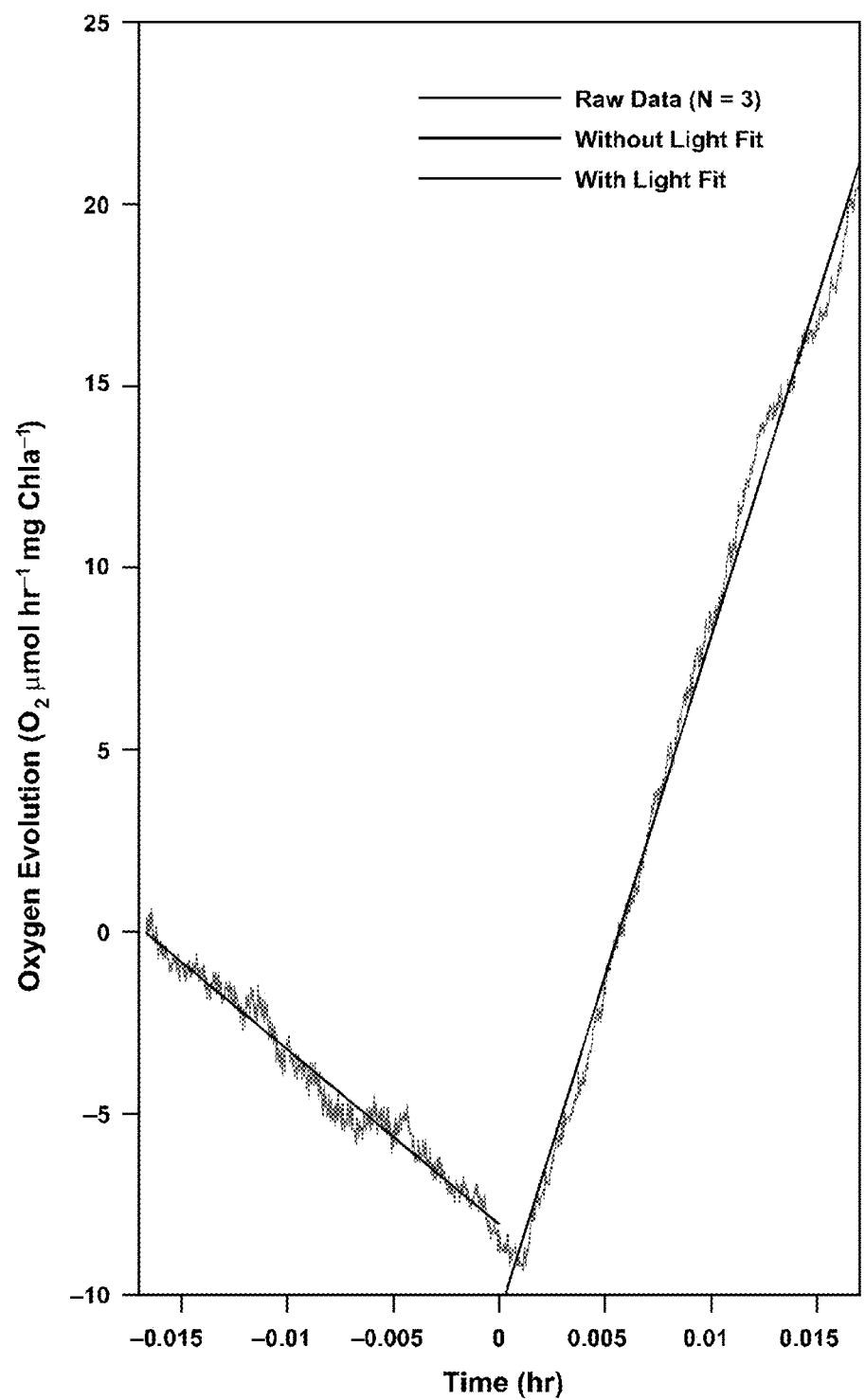
FIG. 6 shows oxygen evolution activity of purified Photosystem II. Results of one technical measurements of N PSII preparations. At time=0, Photosystem II was activated by the addition of saturated red light. The solid lines are 1$^{st}$ degree polynomial fits of the dark (y=−(481±6.6)·x−(8.051±0.064)) and light (y=−(1863±11)·x−(10.53±0.11)) portions of the experiment. The dark correct oxygen evolution rate is 2343.9±24.75 µmol $O_2$ $hr^{-1}$ $mg$ $Chla^{-1}$.

The reconstitution procedure for PSII was identical to that of the CMI proteoliposomes. The lipid to PSII ratio was fixed at 30:1 (w/w) to simplify the interpretation of the effect on the PSII to CMI ratio. FIG. 6 shows oxygen evolution by reconstituted PSII for one example tested. Results are shown from three independent measurements of a single PSII preparation. Saturated red light was added at 0 sec. The maximum rate of oxygen evolution was calculated as 1996.0±156.2 μmol $O_2$ hr$^{-1}$ mg Chlorophyll-a$^{-1}$.

For reconstituted proteoliposomes incorporating both PSII and CMI, oxygen evolution in addition to proton production of the resulting proteoliposomes were measured using a Clarke-type electrode and ACMA, respectively. Typical preparations resulted in a 35% decrease in ACMA signal with oxygen evolution rates of 509.24±256.84 μmol $O_2$ hr$^{-1}$ mg Chlorophyll-a$^{-1}$ (ChlA) with saturated light.

Example 3

Varying Ratios of CMI and PSII

Proteoliposomes containing CMI and PSII were prepared using the same method for the reconstitution of the individual proteins using 5 mM CHAPS. A suite of experiments varying CMI to PSII ratio were conducted including two PSII:CMI ratios; approximately 2 and 4 PSII molecules per molecule of CMI. The rationale for including more PSII then CMI was to allow PSII to rapidly generate and maintain the PMF necessary for the NAD$^+$:DQH$_2$ oxidoreductase activity of CMI.

Figure 7:
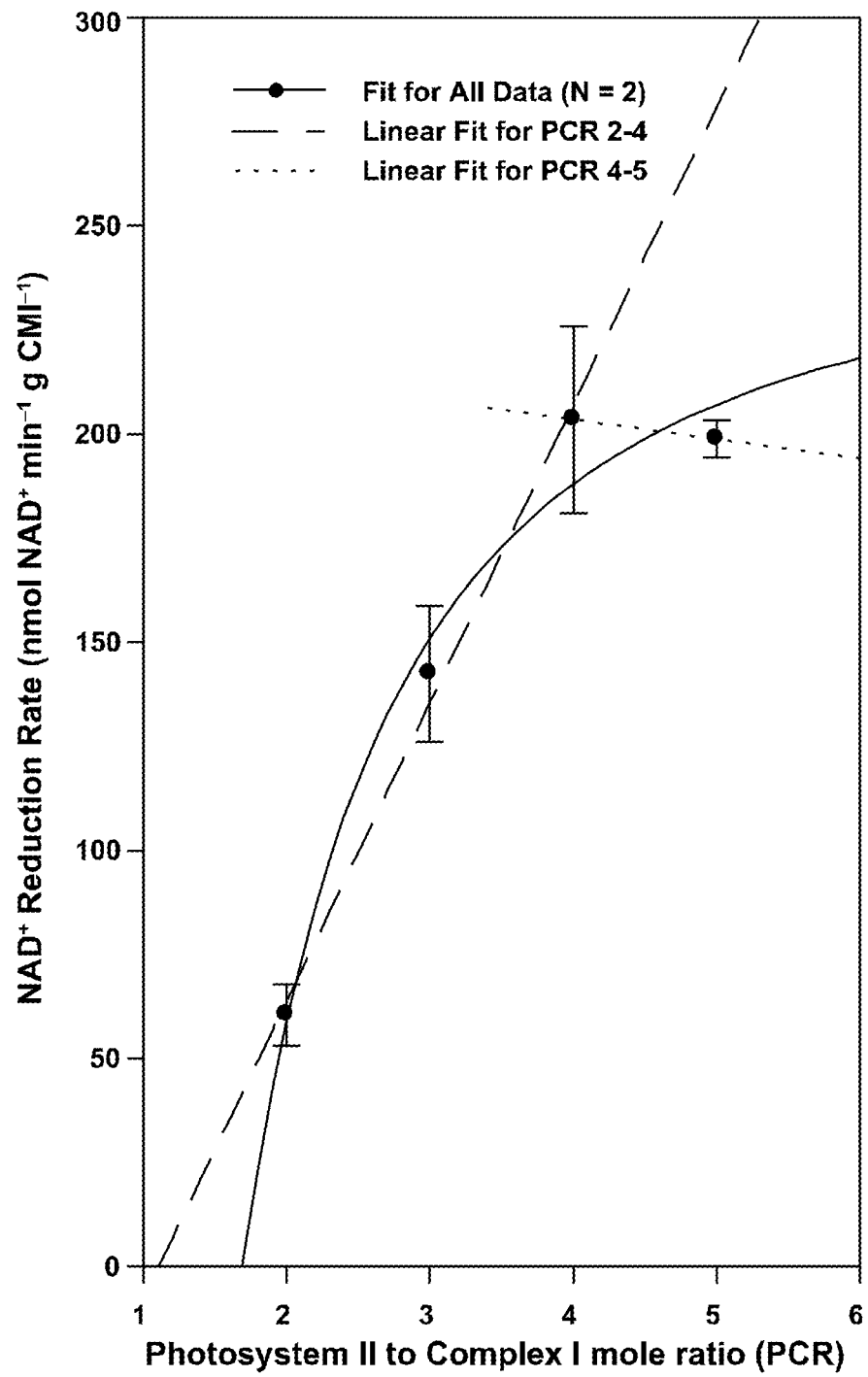
FIG. 7 shows the relationship between PCR and NADH production rate and total NADH produced. The rate of $NAD^+$ reduction versus Photosystem II to Complex I mole ratio (PCR). The error bars represent the standard deviation of n technical repeats of single biological replicate.

Results are shown in FIG. 7. FIG. 7A shows results at 1 mM NAD$^+$, and FIG. 7B shows results with 200 micromolar NADH. FIG. 7C and FIG. 7D show the images inset in FIG. 7A and FIG. 7B, respectively, and include results for empty liposome controls. Data are presented as the mean and standard deviation of three independent measurements of a single preparation.

The first series of NAD$^+$ photoreduction experiments were performed using 1 mM NAD$^+$ as the substrate (FIG. 7A). These initial experiments indicated that the rate of NAD$^+$ photoreduction of the samples containing higher PSII to CMI ratios (4PSII:1CMI) to be 28.6 nmol min$^{-1}$ mg CMI$^{-1}$ which is nearly twice that of rates from samples containing lower PSII to CMI (2PSII:1CMI), 15.1 nmol min$^{-1}$ mg CMI$^{-1}$.

Figure 8A:
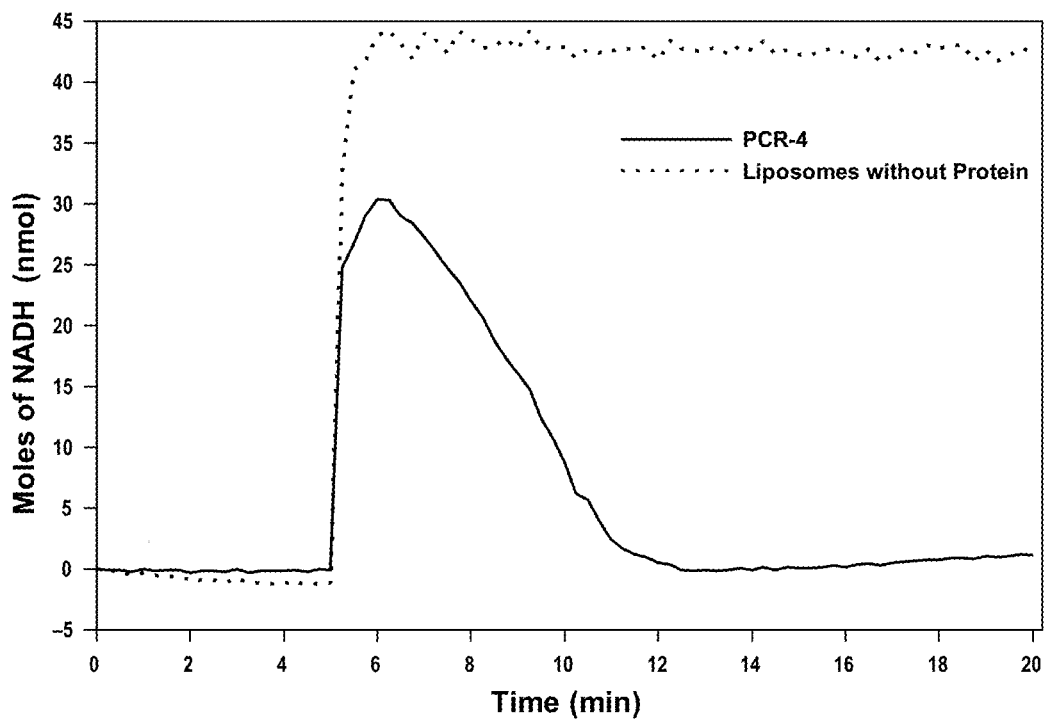
FIG. 8A-B show pre-initiation of $NAD^+$ photoreduction. Typical results from experiments which used 200 µM NADH as substrate before initiating photoreduction. Samples were incubated for 5 minutes prior to addition of 200 µM NADH (added at 5 min) and incubated for an additional 10-15 minutes to allow the ACMA signal to stabilize before starting photoreduction experiments.
Figure 8B:
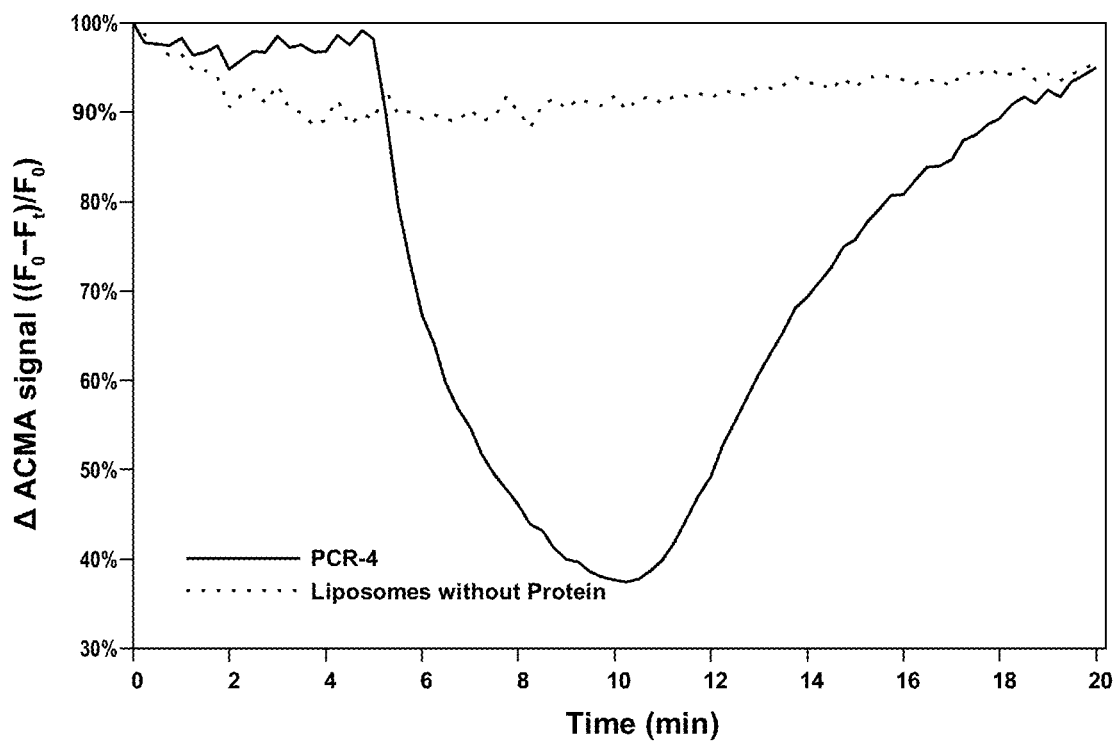

Previous studies on the succinate-supported NAD$^+$ oxidoreduction with submitochondrial particles (SMPs) revealed the addition of NADH activated CMI and rates of RET activity increased [42-43]. Without being bound by theory, results from this example are consistent with these earlier works when NAD$^+$ photoreduction assays are conducted by the addition of 200 μM NADH and initiating photoreduction after CMI no longer is oxidizing the substrate (results shown in FIG. 7B), pre-initiation of NAD$^+$ photoreduction using 200 μM NADH as the substrate is shown in FIG. 8A (NADH concentration) and FIG. 8B (ACMA signal). The resulting NAD$^+$ photoreduction rates were 323 and 89 nmol min$^{-1}$ mg CMI$^{-1}$ for 4PSII:1CMI and 2PSII:1CMI, respectively. In comparison to the experiments using 1 mM NAD$^+$ as the substrate, the rates were nearly an order of magnitude greater. Additionally, the NAD$^+$ photoreduction rate for the 4PSII:1CMI samples approached 4 times of the 2PSII:1CMI samples.

Results from experiments performed to determine the influence of PSII to CMI ratios on NAD$^+$ photoreduction concluded that proteoliposomes 4PSII:1CMI outperformed 2PSII:1CMI. This indicates that more PSII is necessary to maintain the activity of CMI, most likely to maintain the PMF. 4PSII:1CMI preparations, using 200 μM NADH as the substrate were selected for further characterization in subsequent experiments.

Example 4

Inhibition of PSII by DCMU

Figure 9A:
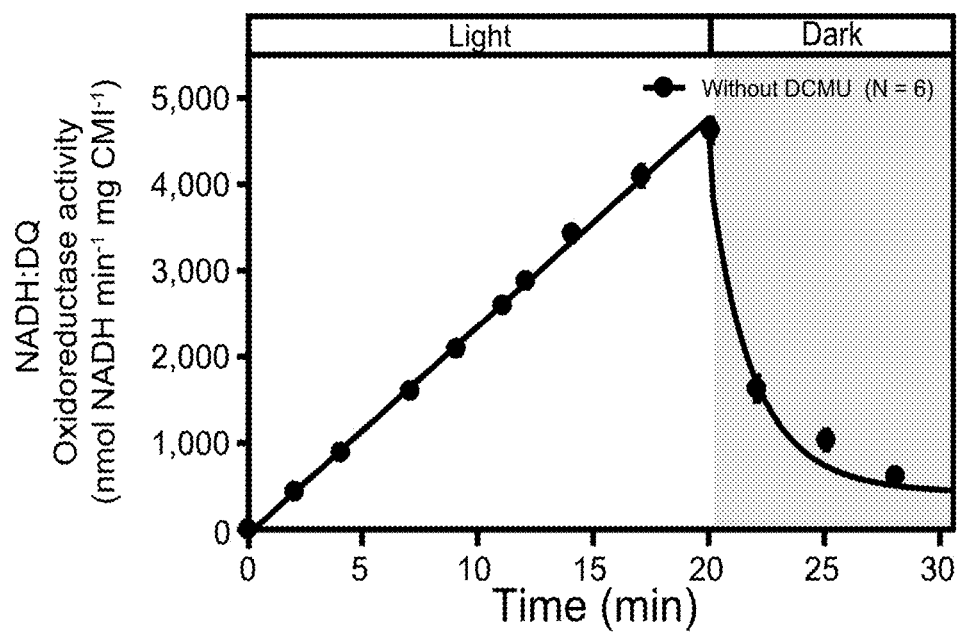
FIG. 9A-D show the relationship between $NAD^+$ photoreduction activity and ACMA signal of PCR-4 proteoliposomes.

To determine the consistency of the methods for preparing the 4PSII:1CMI proteoliposomes, three separate preparations were used. The preparations yielded consistent results, with an average maximum NAD$^+$ photoreduction rate of 354.85±38.71 nmol min$^{-1}$ mg CMI$^{-1}$ (FIG. 9A). Comparing the production rates of H$^+$ to NADH, it is possible to calculate the coupling efficiency of the two enzymes using the reaction stoichiometry of 5 H$^+$ to produce one NADH molecule. During the reaction PSII produces H$^+$ at 4.36±0.79 nmol min$^{-1}$ [calculated from the oxygen evolution activity of 4PSII:1CMI proteoliposomes 377.37±67.97 mol $O_2$ hr$^{-1}$ mg Chlorophyll-a$^{-1}$], whereas CMI is responsible for their consumption at −1.77±0.19 nmol min$^{-1}$ yielding a coupling efficiency of 38.32%±10.80%. Without being bound by theory, the remainder of unused H$^+$ could be accounted for by the protons required to generate the PMF together with protons produced by PSII molecules reconstituted in the incorrect orientation and proton leakage across the vesicle membrane.

When NAD$^+$ photoreduction is initiated both ACMA signal and NADH concentration increase in a similar fashion, suggesting that CMI is pumping protons out of the proteoliposomes as it is reducing NAD$^+$. After photoreduction, confirmation that NADH was being produced was obtained by letting the sample remain in the dark while continuing to monitor ACMA and NADH concentration. Once placed in the dark the NADH accumulated was oxidized. Additionally, as NADH concentration decreased the ACMA signal also decreased, indicating that CMI is pumping protons into the interior of the proteoliposomes. Both observations affirm NADH is being produced through coupling of PSII and CMI activity.

Figure 9B:
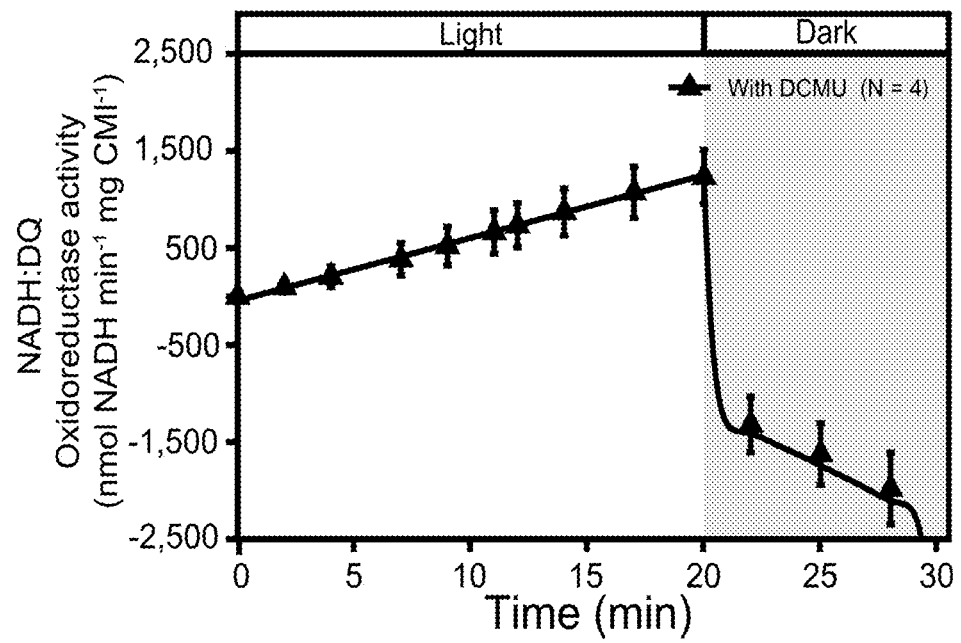
Figure 9C:
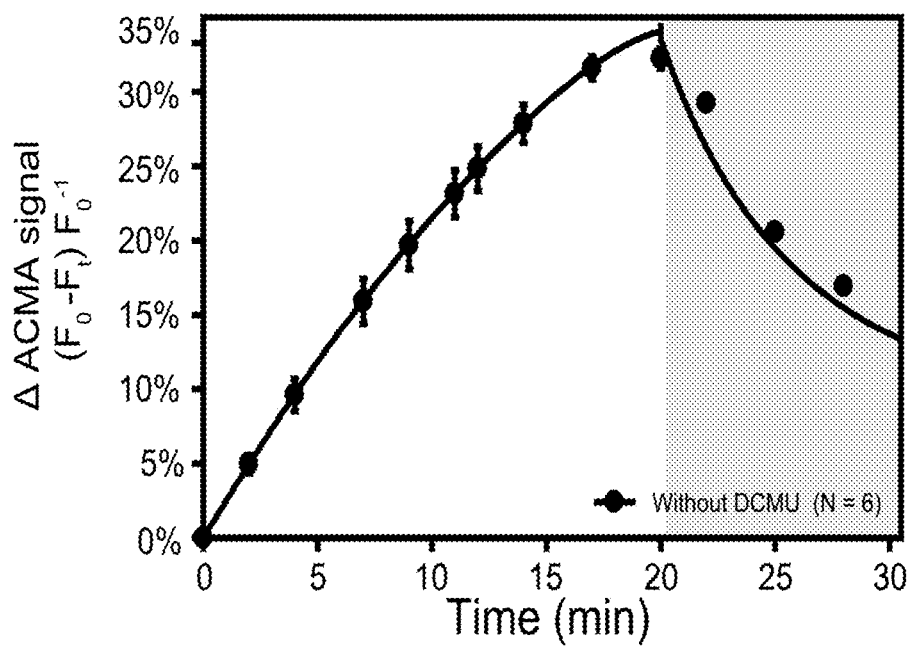
Figure 9D:
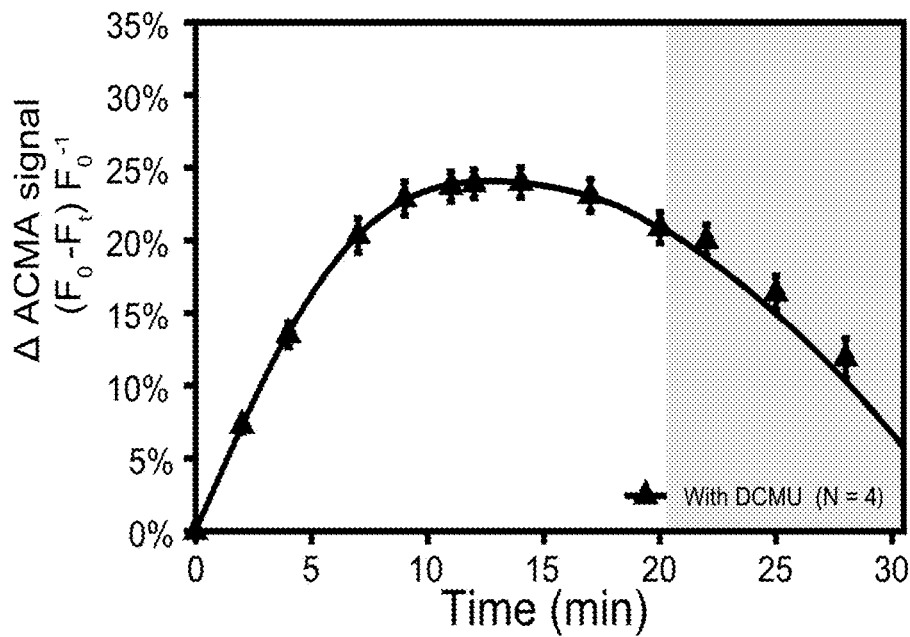

To reinforce the conclusion that PSII is providing electrons through decylubiquinol (DQH$_2$) and the PMF required for CMI to reduce NAD$^+$, PSII inhibition experiments were conducted (FIG. 9B). Prior to the initiation of photoreduction, proteoliposomes were incubated for 5 minutes with 100 μM 3-(3,4-dicholorophenyl)-1,1-dimethylurea (DCMU) an inhibitor of PSII [44-45]. While under illumination the inhibited sample shows a maximum rate of NADH production of 6.44±24.97 nmol min$^{-1}$ mg CMI$^{-1}$ compared to 222.29±12.57 nmol min$^{-1}$ mg CMI$^{-1}$ for the non-inhibited sample. After the removal of light, the average rate of NADH production are −170.65±2.26 and −198.19±13.67 nmol min$^{-1}$ mg CMI$^{-1}$ for the inhibited and non-inhibited samples, respectively. Comparing the results between the samples during and post illumination, PSII is indisputably providing both the electrons and PMF required to drive $NAD^+$ reduction by CMI.

Figure 10:
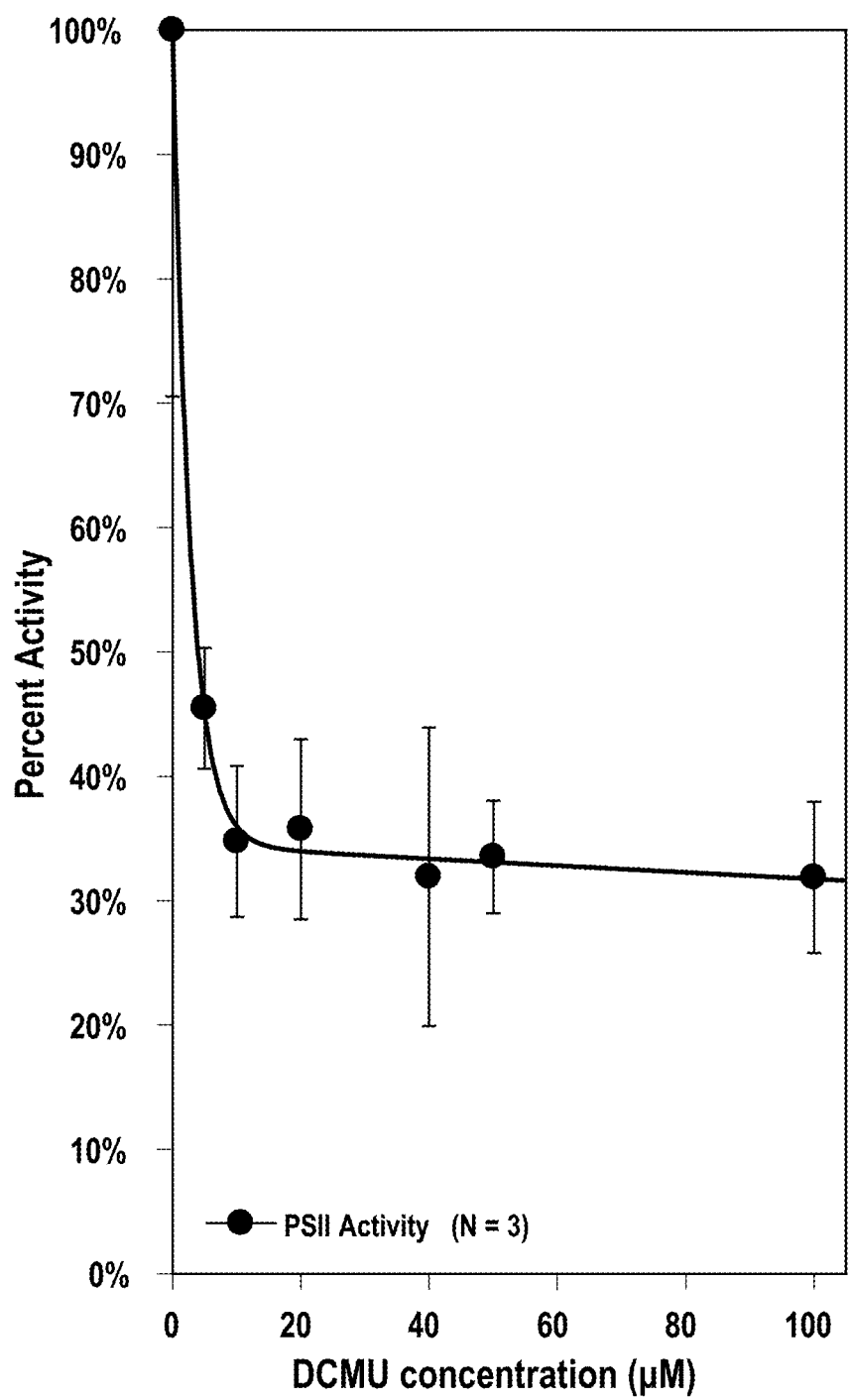
FIG. 10 shows the oxygen evolution activity vs. DCMU concentration for PCR-4 proteoliposomes. The error bars represent N biological replicates with one technical replicate.

Nonetheless, the similarity between the rates post illumination suggest that PSII is not completely inhibited, as experiments showed that isolated PSII was only 70% inhibited by 100 µM DCMU (FIG. 10). Without being bound by theory, the ACMA data is consistent with the interpretation that PSII is not fully inhibited, explaining the signal increase for the inhibited sample. However, the signal increase is only approximately 60% of that seen from the non-inhibited sample. Subtracting the post illumination from the illumination $NAD^+$ production rates, the rate of NADH production of the inhibited sample is 39.05%±7.64% of the non-inhibited sample, which is in good agreement with the interpretation that PSII is inhibited by 70%.

Example 5

Evaluation of Multiple Light Dark Cycles

Figure 11A:
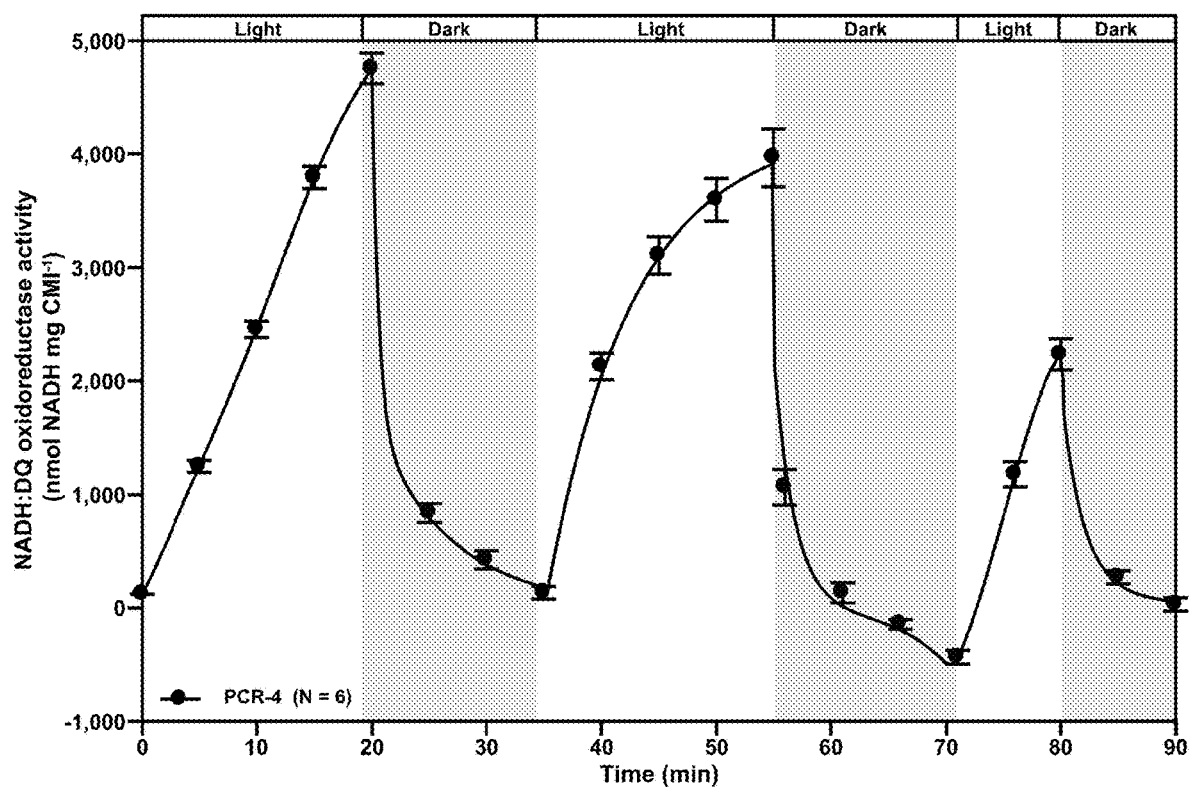
FIG. 11A-B show the photoreduction of $NAD^+$ by PCR-4 proteoliposomes through multiple light-dark cycles.
Figure 11B:
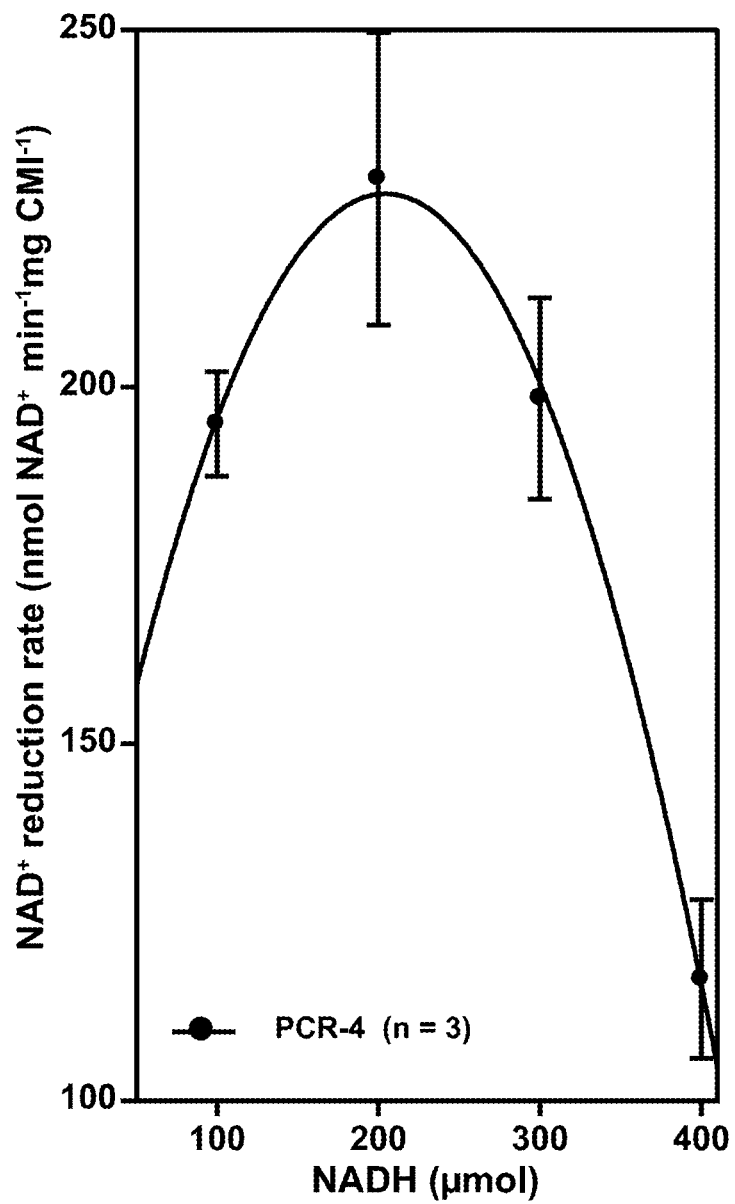

Results of $NAD^+$ photoreduction assays after exposure to light for greater than 10-20 minutes caused the rate of $NAD^+$ reduction to reduce significantly, similar to the plateau seen between 10-25 min for the non-inhibited sample in FIG. 9B. To determine if this phenomenon is due to disruption to the integrity of the system, light-dark cycle photoreduction experiments were performed (FIG. 11A) and FIG. 11C show NADH:DQ oxidoreductase activity; FIG. 11B shows ACMA signal). During the first two light-dark cycles of 20 mins the maximum rates of $NAD^+$ reduction increased from 185.34±59.06 to 319.53±22.33 nmol $min^{-1}$ mg $CMI^{-1}$. This suggests the function of the construct remains, meaning NADH must have an inhibitory effect on the RET for CMI.

To strengthen this conclusion, a NADH titration experiment was performed (FIG. 12, Table 6) to support this conclusion. Little has been published on RET for E. coli CMI, however it is reported for the ATP-driven, succinate-supported RET in SMPs [46]. Without being bound by theory, given the highly conservative nature of CMI between species, it would be logical that NADH could have an inhibitory effect on RET in this system.

TABLE 6

Results from NADH Titration Experiment

| NADH (µM) Injected | Max Rate $NAD^+$ Photoreduction (nmol $min^{-1}$ mg $CMI^{-1}$) | Max Production of NADH (µM) | NADH (µM) remaining prior to photoreduction | Sum NADH (µM) |
| --- | --- | --- | --- | --- |
| 100 | 132.30 | 8.04 | 2.05 | 10.08 |
| 200 | 213.32 | 9.10 | 4.10 | 13.20 |
| 300 | 178.71 | 6.48 | 8.19 | 14.67 |
| 400 | 57.45 | 1.53 | 13.41 | 14.94 |

Conclusions Based on Examples

The results described herein demonstrate an engineered system which successively couples the activity of two multi-subunit membrane protein complexes that do not directly interact naturally for reduction of $NAD^+$. This system only consumes light and water, presenting a step forward in the development of a highly-versatile system that could be readily adapted for any isolated enzyme system requiring NADH recycling. This technology offers significant advantages over current techniques for NADH regeneration that utilize enzymes by eliminating the need for designing a rational reaction route in tandem with developing an efficient separation technology for removal of by-product [2]. This technology will enable the adoption of isolated enzyme systems for sequestration of $CO_2$ as no $CO_2$ is produced from this platform in contrast to many enzyme-based NADH regeneration methods [2-3, 5].

Based on the results herein and the fact that the function of PSII and CMI are conserved across species and between kingdoms, it can be soundly predicted that PSII and CMI from any species can be used in other embodiments to perform the same function as the tested PSII from Cyanobacterium synechocystis 6803 (Synechocystis sp. PCC6803) and CMI from E. coli. Based on the fact that variants of CMI have been engineered to have increased affinity for $NADP^+$/NADH, $NADP^+$ can be regenerated in other similar embodiments. Based on the fact that many analogues of ubiquinone are known in addition to the tested decylubiquinone, other analogues of ubiquinone or decylubiquinone can be used as the electron carrier in other embodiments. Based on the fact that water and light are the only input reactants, while oxygen is the only byproduct, some embodiments described herein can be used in any primary reaction system requiring regeneration of NADH or NADPH, because the water and oxygen are unlikely to interfere with the primary reaction system. Based on the fact that biomimetic membranes, for example based on triblock copolymers, are known to be able to stabilize and permit functioning of membrane proteins, other biomimetic membranes can be used in other embodiments, and embodiments described herein are not limited to the use of a lipid bilayer membrane. While valinomycin was used in the tested embodiments, a proton gradient is still established without the presence of valinomycin, and accordingly valinomycin can be omitted in some embodiments, or alternatively any suitable ionophore can be used in place of valinomycin.

Example 6

Purification of NADH:Ubiquinone Oxidoreductase (Complex I)

Purification of E. coli CMI was performed as described above.

Purification of Bacteriorhodopsin

Bacteriorhodopsin from H. salinarum was purified using tangential flow filtration, followed by solubilization with 5% (w/w) Trion X-100 at 1 mg $ml^{-1}$ for 24 hours. Solubilized bR was captured and detergent was exchanged using anion exchange chromatography.

Liposome preparation, enzyme reconstitution, $NAD^+$ photoreduction, and proton pumping assays were performed as described above.

Example 7

In this study, an engineered artificial organelle capable of photoreduction of $NAD^+$ was created by vectorially integrating bR from H. salinarum and CMI from E. coli into proteoliposomes. The power source for this system is light which activates the proton translocation by bR. As a result, accumulation of $H^+$ within the lumen creates a proton motive force (PMF). The PMF is requisite to diminish the thermodynamic gap of the standard redox potentials between $NADH/NAD^+$ and $QH_2/Q$. Reducing the thermodynamic barrier enables CMI to perform reverse electron transfer (RET) from $QH_2$ to $NAD^+$ [10, 46]. Combing the associated actives of these two enzymes demonstrates the foundation of a platform for NADH recycling for cell free metabolic systems.

The experiments were initially conducted to determine whether the (+)CMI-(+)bR proteoliposomes could reduce $NAD^+$ and find suitable assay conditions.

Other publications suggest RET by CMI has a higher dependence on the $\Delta pH$ then the $\Delta \psi$ electrical component of the PMF for RET [42]. To generate a higher $\Delta pH$, valinomycin was included in the assay. Valinomycin is a potassium ionophore and in turn, eliminates the electrical component of the PMF allowing bR to generate higher pH gradients [47]. However, it has reported that high concentrations of valinomycin can have an inhibitory effect on bR [48]. Two concentrations of valinomycin were tested: 0.1 µM and 0.2 µM. There is significant and moderately strong correlation (r>0.44) and between valinomycin concentrations and $NAD^+$ reductase rate only when Piericidin A is present. In proton pumping assays 0.2 µM valinomycin quenched the ACMA more than 0.1 µM. The results of the experiments agree with other reports that RET by CMI has a higher dependence on $\Delta pH$ then $\Delta \psi$; 0.2 µM valinomycin was used in additional experiments.

Reactive oxygen species (ROS) generation by mammalian CMI during RET is well documented [49]. Published information is limited for RET by E. coli CMI but, given the conservative nature of CMI between species, it is logical that bacterial CMI would also produce ROS during RET. To mitigate the possible detrimental effects that ROS would have on the system, dithiothreitol (DTT) was tested to determine whether it would have a positive effect of $NAD^+$ reduction. When 1.0 mM DTT was present that there is a significant (p-value<0.01) and adverse effect on the reduction of $NAD^+$ whereas 0.2 mM and 0.4 mM had no significant effect. These results were unexpected, and the cause for these findings are outside the scope of this work but may be caused by the electron transfer reactions between the FMN containing active site of CMI with DTT [50].

Figure 12:
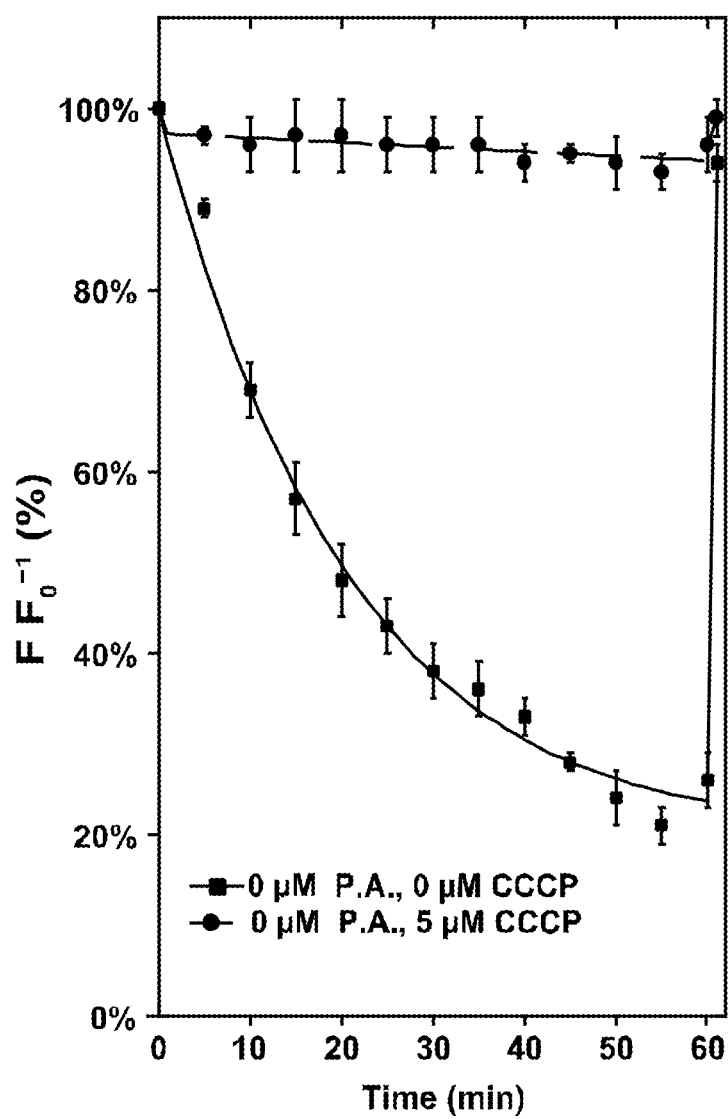
FIG. 12 shows proton pumping by bacteriorhodopsin from *H. salinarum* (bR). Typical results from (−)CMI-(+)bR proteoliposomes. Samples were incubated for 5 min. to allow the ACMA signal to stabilize before starting the experiments. After 60 min, 5 µM CCCP was added to abolish the proton gradient. The results are the representation of three technical repeats of 5 biological replicates.
Figure 13A:
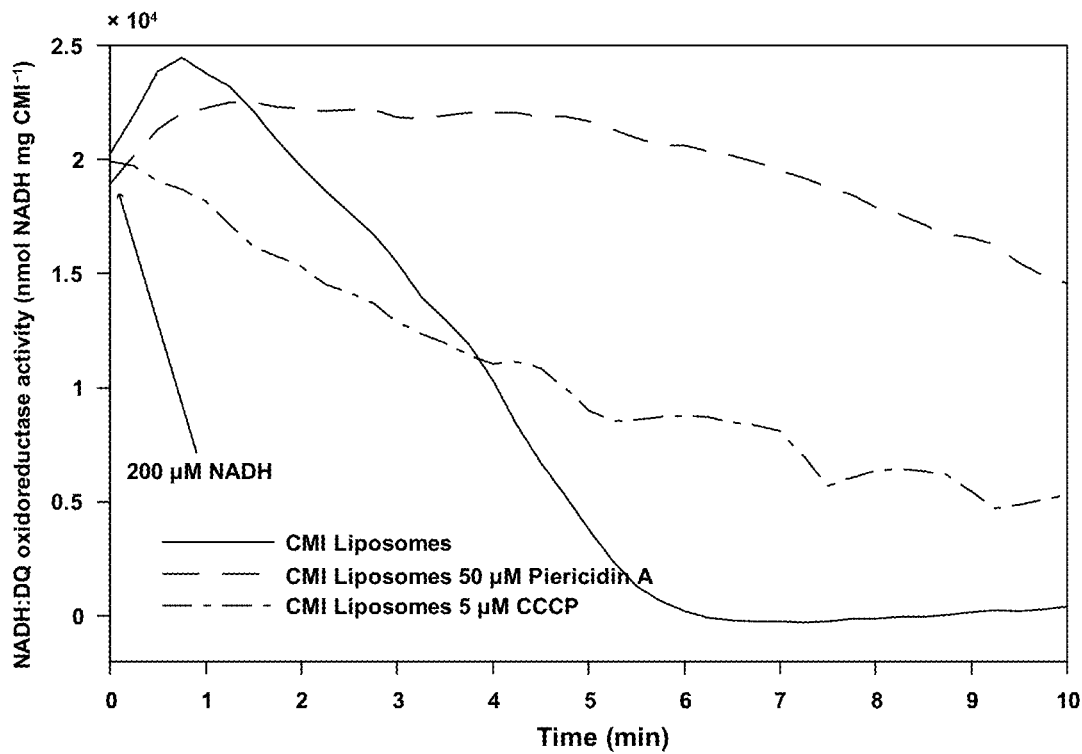
FIG. 13A-C shows proton pumping and inhibition of NADH oxidation in (+)CMI-(−)bR proteoliposomes.
Figure 13B:
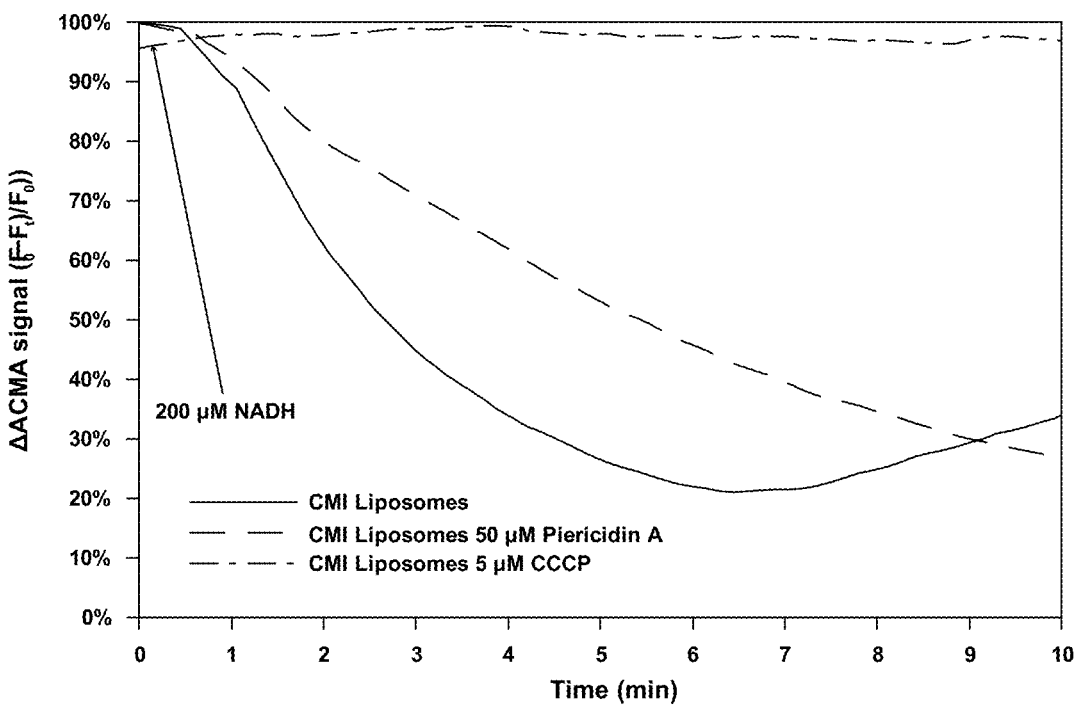
Figure 13C:
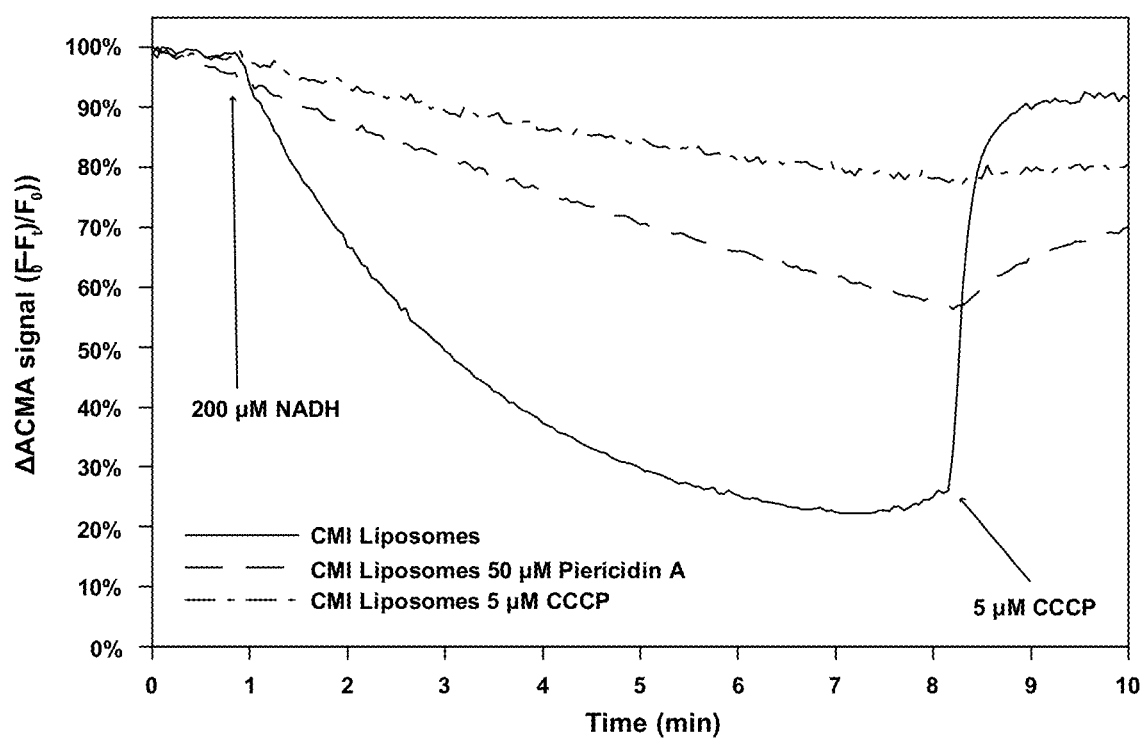

One of the most significant findings in this work was the effect of Piericidin A on the reduction of $NAD^+$. Piericidin A is a well-known and potent inhibitor of the oxidation of NADH by CMI [51]. When 50 µM Piericidin A was included, NADH oxidation was inhibited >95% however, the $NAD^+$ reductase rates were significantly increased with a strong positive correlation coefficient (r>0.92) (FIG. 12-13). This finding was most prominent in the in experiments that contained 0.0 and 1.0 mM DTT (data not shown), resulting in rates nearly 3 and 4 times that of samples which contain no Piericidin A. Kotlyar et al. reported similar findings for the inhibitor rotenone in CMI from *Paracoccus denitrificans* [16]. The two-quinone binding sites may explain the inability for Piericidin A to inhibit RET [52-53].

To confirm that NADH is produced, control experiments were performed at multiple points along the mechanism of the system. Proteoliposomes that did not contain bR were tested for confirmation that bR was providing a $\Delta pH$ to activate RET by CMI. When incorporating bR into the proteoliposomes with CMI, there was a significant difference with strong positive correlation coefficients for all conditions tested indicating that bR is responsible for creating a $\Delta pH$. Samples incubated under light and dark conditions were tested. When the samples were incubated in the dark, they produced little or no NADH. Light was responsible for the NADH production through the activation of bR (r>0.96). Additionally, the experiments showed no significant difference between the (-)bR samples and the (-)Light samples and similar slopes in the response found in (±)bR.

Moreover, to determine if the $\Delta pH$ generated by bR was necessary for NADH production, 5 µM CCCP, a protonophore was included (not shown). With CCCP present, a $\Delta pH$ is unable to establish and results in negative and significant response (p-value<0.001 and <0.0001, r<-0.95 for 0.0 and 1.0 mM DTT respectively).

Figure 14:
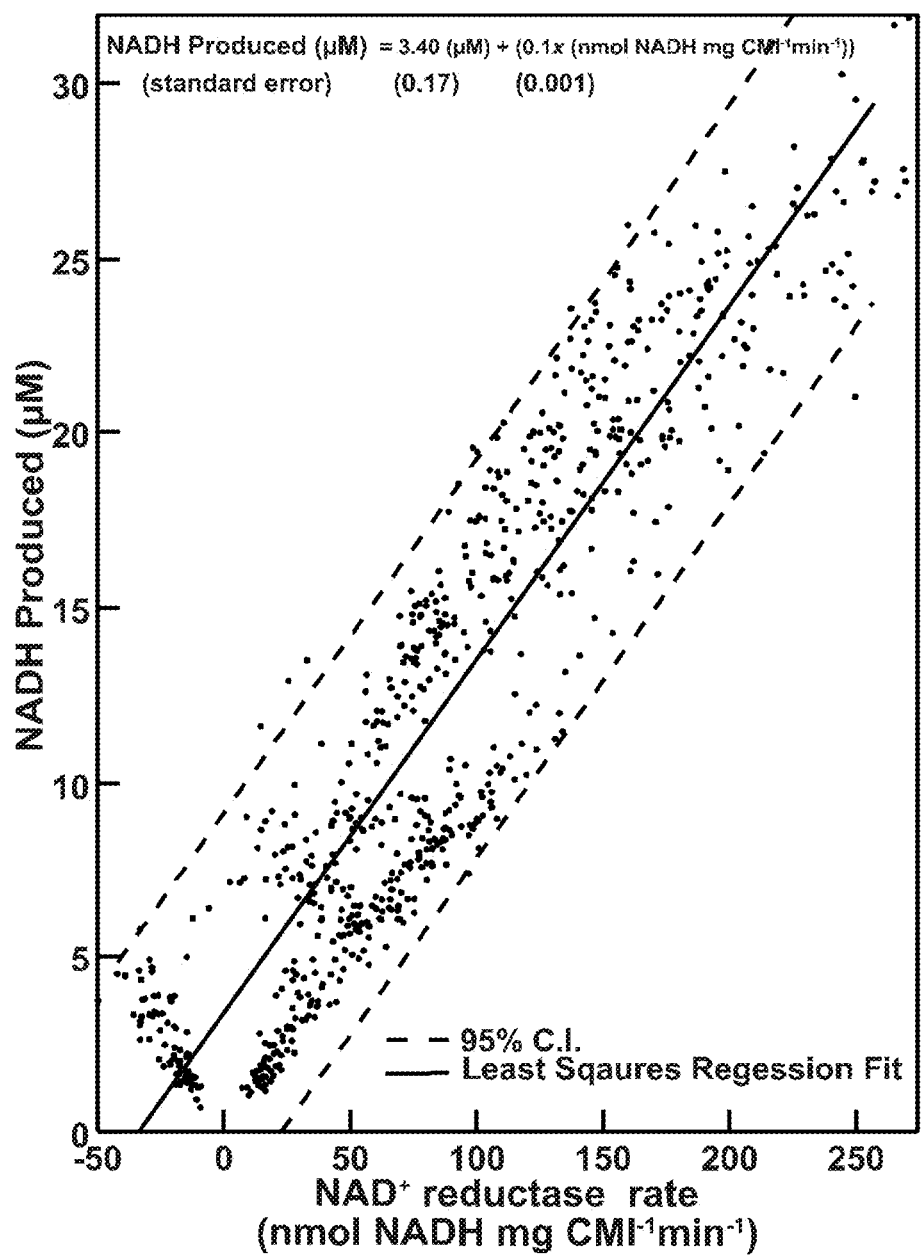
FIG. 14. The relationship between $NAD^+$ reductase rate (nmol NADH mg $CMI^{-1}$ $min^{-1}$) and NADH produced (μM). The formula for the linear less squares fit is shown in the figure legend (p-value>0.0001, $R^2$>0.85). The fit was generated using all observations (N=732) from all conditions tested.

To determine if the rate of $NAD^+$ reductase had a relationship to the total NADH produced (µM) a linear least squares regression was performed on 734 observations (N=762) of (+)CMI-(+)bR proteoliposomes, under all conditions tested (FIG. 14). The estimated gradient 0.1±0.002 (mg CMI $min^{-1}$ nmol $NADH^{-1}$), predicts an increase in $NAD^+$ reductase rate of 10 (NADH mg $CMI^{-1}$ $min^{-1}$) with increase the NADH produced by 1 µM. The effect is small and statistically significant and the coefficient of correlation (r>0.92) indicates a strong positive linear relationship. Although several data points are negative slopes with a net production in NADH, the rates are the absolute maximum steady state values while the NADH produced represents a localized maximum.

The pH-sensitive fluorophore 9-amino-6-chloro-2-methoxyacridine (ACMA) was used to conduct proton pumping assays. The rates of ACMA quenching were measured for CMI bR independently. Because of the non-linear relationship between ACMA quenching and $\Delta pH$ [54-55], the rate of ACMA quenching and de-quenching were calculated using the linear region of the ACMA signal, between 40-70% of the baseline. Light-induced activation of bR causes the ACMA signal to decrease at a rate of $-1.51\pm0.62$ ACMA % $min^{-1}$. During photoreduction of samples with no Piericidin A. present (data not shown), the signal increased by 1.63±0.15 and 1.34±0.37 ACMA % $min^{-1}$ for 0.0 and 1.0 mM DTT, respectively. When 50 µM Piericidin A was present the rate the signal increased nearly doubled to 3.96±0.64 and 3.15±0.94 ACMA % $min^{-1}$ for 0.0 and 1.0 mM DTT, respectively. These results are in good agreement with measured rates of $NAD^+$ reduction for two reasons. Since ACMA reports the signal for the entire population of proteoliposomes and Piericidin A only inhibits the oxidation of NADH by CMI, proteoliposomes may be oxidizing NADH and simultaneously reduced by another population. Furthermore, when Piericidin A is present the rate of NADH produced reduces by 95% after 35 minutes while with no Piericidin A the rate reduced by 72% (data not shown). There is effectively no $\Delta pH$ remaining for CMI to reduce $NAD^+$ after 35 min when Piericidin A is present in comparison to when Piericidin A not present, a $\Delta pH$ is present for the all but the last 5 min of the 60-min assay.

Another interesting finding from the proton pumping assays occurring during the initial 5 mins of illumination. When Piericidin A is not present there is an initial decrease of ACMA quenching before dequenching and starting NADH production which is not evident when Piericidin A is present or in dark incubated samples (data not shown). The ACMA data is difficult to precisely decouple the actions of each of the two enzymes but, the initial decrease in ACMA signal can be attributed to a charging of the system by bR. This observation indicates that RET through CMI may require a specific magnitude of $\Delta pH$ before switching on and continuing.

These results demonstrate the assembly and testing of an artificial organelle comprising bacteriorhodopsin from *Halobacterium salinarum* and *E. coli* CMI that enables reduction of $NAD^+$. The significances of findings reported here are that the reversible machine CMI can utilize a $\Delta pH$ to transfer electrons from $QH_2$ to $NAD^+$ while the addition of Piericidin A enhances $NAD^+$ reduction by inhibiting the oxidation of NADH by CMI. This, in turn, allows NADH to be readily available for other synthetic biochemical reaction pathways.

This research provides the foundation for further development of systems for power generation in in vitro metabolic systems. Additionally, this technology reduces the constraints on designing metabolic pathways found in other methods for maintaining redox balance, enabling development of more diverse and complex cell free metabolic systems. Coupling this system, with ATP-producing artificial organelles, will permit the creation biological energy power systems for various applications.

What is claimed is:

1. An artificial cell free organelle system comprising:
a membrane having two sides comprising an inner surface in contact with an inner aqueous medium and an outer surface in contact with an outer aqueous medium;
one or more photosynthetic proteins and one or more oxidoreductase proteins are vectorially embedded within and traversing the membrane;
one or more first redox active cofactors;
one or more second redox active cofactors;
water, and
a photon energy source;
wherein:
when one or more photons are directed on the one or more photosynthetic proteins, the photosynthetic proteins harvest the photon energy and catalyze the oxidation of at least one water molecule in the inner aqueous medium, generating 0.5 equivalents of oxygen gas and yielding up to two protons and two electrons per two photons that are transferred to an oxidized form of the first redox active cofactor, generating a reduced form of the first redox active cofactor;
the accumulation of protons in the inner aqueous medium generates a proton concentration gradient between the inner aqueous medium and the outer aqueous medium; and
the one or more oxidoreductase proteins pumps protons from the inner aqueous medium through the membrane to the outer aqueous medium to reduce the proton concentration gradient and simultaneously catalyzes the transfer of electrons from the reduced first redox cofactor to an oxidized form of the second redox active cofactor, generating a reduced form of the second redox active cofactor and an oxidized form of the first redox active cofactor.

2. The system of claim 1, wherein the membrane comprises a biomimetic bilayer, a biomimetic three-dimensional bilayer, a unilamellar liposome, a planar membrane, or a membraneous polymer construct.

3. The system of claim 2, wherein the membraneous polymer construct comprises a triblock co-polymer membrane comprising varying lengths of poly(dimethylsiloxane) (PDMS) as the hydrophobic membrane-forming block and poly(2-methyloxazoline) (PMOXA) as the hydrophilic membrane-forming block.

4. The system of claim 1, wherein the membrane comprises a closed unilamellar liposome comprising a phospholipid bilayer.

5. The system of claim 1, wherein one or more photosynthetic proteins and one or more oxidoreductase proteins are vectorially embedded in the membrane using a detergent.

6. The system of claim 5, wherein the detergent comprises one or more of CHAPS (3-[(3-cholamidopropyl)dimethylammonio]-1-propanesulfonate), DDM (n-dodecyl-β-D-maltoside), OG (octyl-β-D-glucopyranoside), or Triton X-100.

7. The system of claim 1, wherein the one or more photosynthetic proteins comprises the photosystem II complex of proteins or bacteriorhodopsin.

8. The system of claim 7, wherein the photosystem II complex of proteins comprises the photosystem II complexes from *Cyanobacterium synechocystis*, *Synechocystis* sp., *Synechococcus elongates*, *Thermosynechococcus elongatus*, *Thermosynechococcus vulcans*, *Pisum sativum*, *Chlamydomonas reinhardtii*, *Spinacia oleracea*, or *Arabidopsis thaliana*; and
the bacteriorhodopsin comprises the bacteriorhodopsin from *Halobacterium salinarum*.

9. The system of claim 7, wherein the photosystem II complex of proteins or bacteriorhodopsin are purified or recombinant.

10. The system of claim 1, wherein the one or more photosynthetic proteins comprise the photosystem II complex of proteins from *Synechocystis* sp. PCC6803.

11. The system of claim 1, wherein the one or more oxidoreductase enzymes comprises the Respiratory Complex I complex of proteins.

12. The system of claim 11, wherein the Respiratory Complex I complex of proteins comprises the Respiratory Complex I of *Eschericia coli*, *Thermus thermophilus*, *Vibrio cholerae*, *Yarrowia lipolytica*, *Ovis aries*, *Bos taurus*, *Mus musculus*, or *Homo sapiens*.

13. The system of claim 11, wherein the Respiratory Complex I complex of proteins are purified or recombinant.

14. The system of claim 1, wherein the one or more oxidoreductase enzymes comprises the Respiratory Complex I complex of proteins from *E. coli*.

15. The system of claim 1, wherein the one or more oxidoreductase enzymes comprises a Respiratory Complex I that has been engineered to preferentially reduce NADPH.

16. The system of claim 1, wherein the one or more oxidoreductase enzymes are vectorially incorporated into the membrane in an orientation opposite to the orientation of the oxidoreductase enzyme in vivo.

17. The system of claim 1, wherein the first redox active cofactor comprises ubiquinone or a ubiquinone analogue.

18. The system of claim 17, wherein the ubiquinone analogue has the structure:

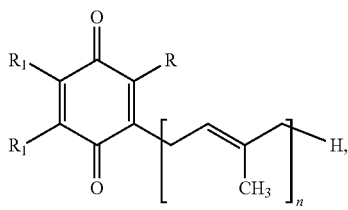

wherein R is methyl, hydroxyl, or hydrogen and $R_1$ is independently methoxy, methyl, hydroxyl or hydrogen, and n is an integer between 0 to 20, 6 to 12, or 7 to 10, including all integers within the specified ranges.

19. The system of claim 1, wherein the second redox active cofactor comprises $NAD^+$, $NADP^+$, an $NAD^+$ analogue, or an $NADP^+$ analogue.

20. The system of claim 19, wherein the $NAD^+$ or $NADP^+$ analogue has the structure:

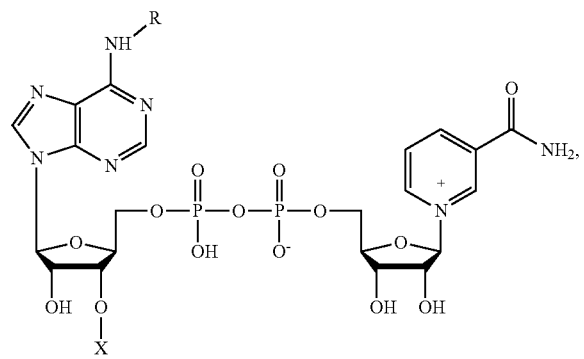

where R is a polyethylene glycol of 100 to 10,000 MW, a carbohydrate moiety or a polypeptide, and X is phosphate or hydrogen.

21. The system of claim 1, wherein the reduced form of the first redox active cofactor comprises ubiquinol, decylubiquinol, or a ubiquinol analogue.

22. The system of claim 21, wherein the ubiquinol analogue has the structure:

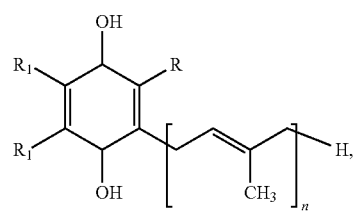

wherein R is methyl, hydroxyl, or hydrogen and $R_1$ is independently methoxy, methyl, hydroxyl or hydrogen, and n is an integer between 0 to 20, 6 to 12, or 7 to 10, including all integers within the specified ranges.

23. The system of claim 1, wherein the reduced form of the second redox active cofactor comprises NADH, NADPH, an NADH analogue, or an NADPH analogue.

24. The system of claim 23, wherein the NADH or NADPH analogue has the structure:

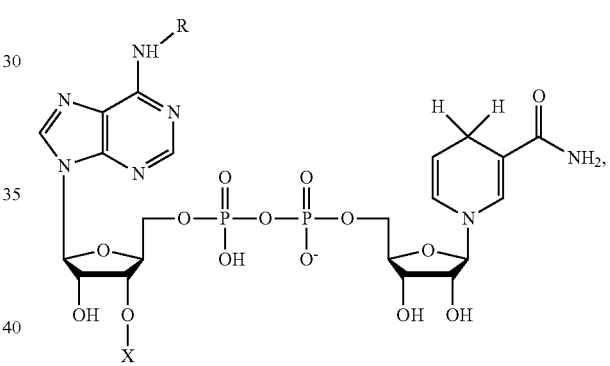

where R is a polyethylene glycol of 100 to 10,000 MW, a carbohydrate moiety, or a polypeptide, and X is phosphate or hydrogen.

25. The system of claim 1, further comprising an ionophore comprising one or more of valinomycin, salinomycin, lasalocid, ionomycin, nonactin, beauvericin, or calcimycin.

26. The system of claim 1, further comprising an ionophore comprising a potassium ionophore, and wherein the potassium ionophore comprises valinomycin or salinomycin.

* * * * *